US011897950B2

(12) United States Patent
Liu et al.

(10) Patent No.: US 11,897,950 B2
(45) Date of Patent: Feb. 13, 2024

(54) OSTEOPONTIN MONOCLONAL ANTIBODIES

(71) Applicants: Augusta University Research Institute, Inc., Augusta, GA (US); Department of Veterans Affairs, Washington, DC (US)

(72) Inventors: Kebin Liu, Augusta, GA (US); John Klement, Augusta, GA (US); Priscilla S. Redd, Augusta, GA (US)

(73) Assignees: Augusta University Research Institute, Inc., Augusta, GA (US); Department of Veterans Affairs, Washington, DC (US)

(*) Notice: Subject to any disclaimer, the term of this patent is extended or adjusted under 35 U.S.C. 154(b) by 455 days.

(21) Appl. No.: 17/112,098

(22) Filed: Dec. 4, 2020

(65) Prior Publication Data
US 2021/0188959 A1  Jun. 24, 2021

Related U.S. Application Data

(60) Provisional application No. 62/944,777, filed on Dec. 6, 2019.

(51) Int. Cl.
C07K 16/24 (2006.01)
A61K 39/00 (2006.01)
A61K 45/06 (2006.01)

(52) U.S. Cl.
CPC ............ *C07K 16/24* (2013.01); *A61K 45/06* (2013.01); *A61K 2039/505* (2013.01); *C07K 2317/565* (2013.01); *C07K 2319/30* (2013.01)

(58) Field of Classification Search
CPC ................... C07K 16/24; A61K 2039/505
See application file for complete search history.

(56) References Cited

U.S. PATENT DOCUMENTS

| | | |
|---|---|---|
| 4,444,887 A | 4/1984 | Hoffmann |
| 4,716,111 A | 12/1987 | Osband et al. |
| 4,816,397 A | 3/1989 | Boss et al. |
| 4,816,567 A | 3/1989 | Cabilly et al. |
| 5,225,539 A | 7/1993 | Winter |
| 5,413,923 A | 5/1995 | Kucherlapati et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,766,886 A | 6/1998 | Studnicka et al. |
| 5,814,318 A | 9/1998 | Lonberg et al. |
| 5,916,771 A | 6/1999 | Hori et al. |
| 5,939,598 A | 8/1999 | Kucherlapati et al. |
| 6,005,079 A | 12/1999 | Casterman et al. |
| 6,180,370 B1 | 1/2001 | Queen et al. |
| 6,331,415 B1 | 12/2001 | Cabilly et al. |
| 6,350,861 B1 | 2/2002 | Co et al. |
| 6,407,213 B1 | 6/2002 | Carter et al. |
| 7,052,694 B2 | 5/2006 | Pease et al. |
| 7,332,582 B2 | 2/2008 | Hardy et al. |
| 7,390,888 B2 | 6/2008 | Pease et al. |
| 7,411,051 B2 | 8/2008 | Rosen et al. |
| 7,488,802 B2 | 2/2009 | Collins et al. |
| 7,521,051 B2 | 4/2009 | Collins et al. |
| 7,524,498 B2 | 4/2009 | Hardy et al. |
| 7,563,869 B2 | 7/2009 | Honjo et al. |
| 7,981,416 B2 | 7/2011 | Hardy et al. |
| 8,088,905 B2 | 1/2012 | Collins et al. |
| 8,114,845 B2 | 2/2012 | Langermann et al. |
| 8,188,238 B2 | 5/2012 | Pease et al. |
| 8,287,856 B2 | 10/2012 | Li et al. |
| 8,383,796 B2 | 2/2013 | Korman et al. |
| 8,580,247 B2 | 11/2013 | Li et al. |
| 8,609,089 B2 | 12/2013 | Langermann et al. |
| 8,709,416 B2 | 4/2014 | Langermann et al. |
| 8,728,474 B2 | 5/2014 | Honjo et al. |
| 8,779,105 B2 | 7/2014 | Korman et al. |
| 9,067,999 B1 | 6/2015 | Honjo et al. |
| 9,073,994 B2 | 7/2015 | Ionjo et al. |

(Continued)

FOREIGN PATENT DOCUMENTS

| | | |
|---|---|---|
| EP | 0592106 A1 | 4/1994 |
| EP | 0239400 B1 | 8/1994 |

(Continued)

OTHER PUBLICATIONS

Lloyd et al., Protein Engineering, Design & Selection, 22:159-168, 2009 (Year: 2009).*

Most et al., "Cyclophosphamide Chemotherapy Sensitizes Tumor Cells to TRAIL-Dependent CD8 T Cell-Mediated Immune Attack Resulting in Suppression of Tumor Growth," PLoS ONE, (2009), 4(9), e6982.

Most et al., Tumor eradication after cyclophosphamide depends on concurrent depletion of regulatory T cells: a role for cycling TNFR2-expressing effector-suppressor T cells in limiting effective chemotherapy, Cancer Immunol. Immunother., 58:1219-1228 (2009).

Mueller et al., "Humanized porcine VCAM-specific monoclonal antibodies with chimeric IgG2/G4 constant regions block human leukocyte binding to porcine endothelial cells," Mol. Immun., 34(6):441-452 (1997).

(Continued)

*Primary Examiner* — Elly-Gerald Stoica
(74) *Attorney, Agent, or Firm* — Smith, Gambrell & Russell; Judy Jarecki-Black

(57) ABSTRACT

Antibodies and antigen binding fragments thereof that immunospecifically bind OPN (OPN) and inhibit OPN activity are provided herein. The disclosed antibodies and antigen binding fragments are useful for modulating signal transduction through OPN proteins. The antibodies and antigen-binding fragments are useful for the treatment or prevention of cancer, osteoporosis, or other immune diseases.

8 Claims, 23 Drawing Sheets

Specification includes a Sequence Listing.

(56) References Cited

U.S. PATENT DOCUMENTS

| | | | |
|---|---|---|---|
| 9,084,776 | B2 | 7/2015 | Korman et al. |
| 9,102,725 | B2 | 8/2015 | Korman et al. |
| 9,205,148 | B2 | 12/2015 | Langermann et al. |
| 9,255,147 | B2 | 2/2016 | Pease et al. |
| 9,273,135 | B2 | 3/2016 | Korman et al. |
| 9,358,289 | B2 | 6/2016 | Korman et al. |
| 9,387,247 | B2 | 7/2016 | Korman et al. |
| 9,393,301 | B2 | 7/2016 | Honjo et al. |
| 9,492,539 | B2 | 11/2016 | Korman et al. |
| 9,492,540 | B2 | 11/2016 | Korman et al. |
| 9,580,507 | B2 | 2/2017 | Korman et al. |
| 2003/0229208 | A1 | 12/2003 | Queen et al. |
| 2004/0049014 | A1 | 3/2004 | Queen et al. |
| 2005/0037000 | A1 | 2/2005 | Stavenhagen et al. |
| 2005/0064514 | A1 | 3/2005 | Stavenhagen et al. |
| 2007/0202077 | A1 | 8/2007 | Brodsky et al. |

FOREIGN PATENT DOCUMENTS

| | | |
|---|---|---|
| EP | 0519596 B1 | 2/2005 |
| GB | 2188638 A | 10/1987 |
| GB | 2209757 A | 5/1989 |
| WO | 91/09967 A1 | 7/1991 |
| WO | 91/10741 A1 | 7/1991 |
| WO | 93/17105 A1 | 9/1993 |
| WO | 94/04678 A1 | 3/1994 |
| WO | 94/25591 A1 | 11/1994 |
| WO | 96/33735 A1 | 10/1996 |
| WO | 96/34096 A1 | 10/1996 |
| WO | 98/16654 A1 | 4/1998 |
| WO | 98/24893 A2 | 6/1998 |
| WO | 98/46645 A2 | 10/1998 |
| WO | 98/50433 A2 | 11/1998 |
| WO | 2007/056539 A2 | 5/2007 |

OTHER PUBLICATIONS

Muyldermans et al., "Recognition of antigens by single-domain antibody fragments: the superfluous luxury of paired domains," Trends Biochem. Sci., 26(4):230-235 (2001).

Nuttall et al., "Immunoglobulin VH Domains and Beyond Design and Selection of Single-Domain Binding and Targeting Reagents," Curr. Pharm. Biotech., 1(3):253 (2000).

Padlan, "A possible procedure for reducing the immunogenicity of antibody variable domains while preserving their ligand-binding properties," Molecular Immunology, 28(4/5):489-498 (1991).

Pedersen et al., "Comparison of Surface Accessible Residues in Human and Murine Immunoglobulin Fv Domains: Implication for Humanization of Murine Antibodies," J. Mol. Biol. 235:959-973 (1994).

Pluckthun in The Pharmacology of Monoclonal Antibodies, vol. 113, Rosenburg and Moore eds. Springer-Verlag, New York, pp. 269-315 (1994).

Pluckthun, "Chapter 11 Antibodies from *Escherichia coli*," The Pharmacology of Monoclonal Antibodies, (1994), pp. 269-270.

Presta, "Antibody engineering," Curr. Op. Struct. Biol., 3:394-398 (1992).

Presta, "Molecular engineering and design of therapeutic antibodies," Curr. Opin. Immun., 20:460-470 (2008).

Reichmann et al., "Single domain antibodies: comparison of camel VH and camelised human VH domains," J. Immunol. Meth., 231:25-38 (1999).

Ribas, "Adaptive Immune Resistance: How Cancer Protects from Immune Attack," Cancer Discov., 5(9):915-919 (2015).

Riechmann et al., "Reshaping human antibodies for therapy," Nature, 332(6162):323-329 (1988).

Rittling et al., "Mice lacking osteopontin show normal development and bone structure but display altered osteoclast formation in vitro," J. Bone Miner Res., 13(7):1101-1111 (1998).

Rittling et al., "Osteopontin Function in Pathology: Lessons from Osteopontin-Deficient Mice," Exp Nephrol., 7:103-113 (1999).

Roguska et al., "A comparison of two murine monoclonal antibodies humanized by CDR-grafting and variable domain resurfacing," Protein Eng., 9:895-904 (1996).

Roguska et al., "Humanization of murine monoclonal antibodies through variable domain resurfacing," Proc. Natl. Acad. Sci. USA, 91:969-973 (1994).

Sammartino et al., "Anti-GBM disease following CTLA4 blockade in a patient with metastatic melanoma," Clinical Kidney Journal, 3(2):135-137 (2010).

Sandhu, "A rapid procedure for the humanization of monoclonal antibodies," Gene 150:409-10 (1994).

Studnicka et al., "Human-engineered monoclonal antibodies retain full specific binding activity by preserving non-CDR complementarity-modulating residues," Protein Engineering, 7:805-814 (1994).

Sun et al., "Interferon Regulator Factor 8 (IRF8) Limits Ocular Pathology during HSV-1 Infection by Restraining the Activation and Expansion of CD8+ T Cells," PLoS One, 11(5):e0155420 (2016).

Swann et al., "Considerations for the development of therapeutic monoclonal antibodies," Cur. Opin. Immun., 20:493-499 (2008).

Taieb et al., "Chemoimmunotherapy of tumors: cyclophosphamide synergizes with exosome based vaccines," J. J. Immunol., 176:2722-2729 (2006).

Tamura et al., "Identification of target genes and a unique cis element regulated by IRF-8 in developing macrophages," Blood, 106(6):1938-1947 (2005).

Tan et al., "'Superhumanized' antibodies: reduction of immunogenic potential by complementarity-determining region grafting with human germline sequences: application to an anti-CD28," J. Immunol., 169:1119-1125 (2002).

Tang et al., "PD-L1 on host cells is essential for PD-L1 blockade-mediated tumor regression," J. Clin. Invest., 128(2):580-588 (2018).

Taylor et al., "Glycogen Synthase Kinase 3 Inactivation Drives T-bet-Mediated Downregulation of Co-receptor PD-1 to Enhance CD8(+) Cytolytic T Cell Responses," Immunity, 44(2):274-286 (2016).

Wang et al., "A reporter mouse reveals lineage-specific and heterogeneous expression of IRF8 during lymphoid and myeloid cell differentiation," J. Immunol., 193(4):1766-1777 (2014).

Wherry, "T cell exhaustion," Nat. Immunol., 12(6):492-499 (2011).

Ariyan et al., Robust Antitumor Responses Result from Local Chemotherapy and CTLA-4 Blockade, Cancer Immunol. Res., 6(2):189-200 (2018).

Baaten et al., CD44 regulates survival and memory development in Th1 cells, Immunity, 32(1):104-115 (2010).

Baca et al., Antibody humanization using monovalent phage display, J. Biol. Chem., 272(16):10678 10684 (1997).

Bass et al., Immunopotentiation with low-dose cyclophosphamide in the active specific immunotherapy of cancer, Cancer Immunol. Immunother., 47:1-12 (1998).

Berger et al., Phase I safety and pharmacokinetic study of CT-011, a humanized antibody interacting with PD-1, in patients with advanced hematologic malignancies, Clin. Cancer Res., 14(10):3044-3051 (2008).

Boussiotis, Molecular and Biochemical Aspects of the PD-1 Checkpoint Pathway, N. Engl. J. Med., 375(18):1767-1778 (2016).

Brahmer et al., Safety and activity of anti-PD-L1 antibody in patients with advanced cancer, N. Engl. J. Med., 366(26):2455-2465 (2012).

Butte et al., Programmed death-1 ligand 1 interacts specifically with the B7-1 costimulatory molecule to inhibit T cell responses, Immunity, vol. 27, pp. 111-122, (2007).

Caldas et al., Design and synthesis of germline-based hemi-humanized single-chain Fv against the CD18 surface antigen, Protein Eng., 13:353-360 (2000).

Chothia et al., "Structural Determinants in the Sequences of Immunoglobulin Variable Domain," J. Mol. Biol., 278:457-479 (1998).

Chothia et al., Canonical structures for the hypervariable regions of immunoglobulins, J. Mol. Biol., 196:901-917 (1987).

Couto et al., Anti-BA46 monoclonal antibody Mc3: humanization using a novel positional consensus and in vivo and in vitro characterization, Cancer Res., 55:1717 22 (1995).

(56) References Cited

OTHER PUBLICATIONS

Couto et al., Designing human consensus antibodies with minimal positional templates, Cancer Res., 55(23 Supp):5973s 5977s (1995).
Cubillos-Ruiz et al., Polyethylenimine-based siRNA nanocomplexes reprogram tumor-associated dendritic cells via TLR5 to elicit therapeutic antitumor immunity, J. Clin. Invest., 119(8): 2231-2244 (2009).
Curtsinger et al., CD8+ memory T cells (CD44high, Ly-6C+) are more sensitive than naive cells to (CD44low, Ly-6C-) to TCR/CD8 signaling in response to antigen, J. Immunol., 160(7):3236-3243 (1998).
Erbe et al., Small molecule ligands define a binding site on the immune regulatory protein B7.1, J. Biol. Chem., 277:7363-7368 (2002).
Freeman, Structures of PD-1 with its ligands: sideways and dancing cheek to cheek, Proc. Natl. Acad. Sci. U. S. A, 105:10275-10276 (2008).
Gillies et al., "High-level expression of chimeric antibodies using adapted cDNA variable region cassettes," J. Immunol. Methods, 125:191-202 (1989).
Golstein et al., "An early history of T cell-mediated cytotoxicity," Nat. Rev. Immunol., 18(8):527-535 (2018).
Greenspan et al., "Idiotypes: Structure and Immunogenicity," FASEB J., 7:437-444 (1989).
Hanson et al., Eradication of established tumors by CD8+ T cell adoptive immunotherapy, Immunity, 13(2):265-276 (2000).
Harper et al., "CD8 T-cell recognition of acquired alloantigen promotes acute allograft rejection," Proc. Natl. Acad. Sci. U.S.A., 112(41):12788-12793 (2015).
Hengst et al., "Cooperation between Cyclophosphamide Tumoricidal Activity and Host Antitumor Immunity in the Cure of Mice Bearing Large MOPC-315 Tumors," Cancer Res., 41:2163-2167 (1981).
Hengst et al., Importance of timing in cyclophosphamide therapy of MOPC-315 tumor-bearing mice, Cancer Res., 40:2135-2141 (1980).
Hirano et al., Blockade of B7-H1 and PD-1 by monoclonal antibodies potentiates cancer therapeutic immunity, Cancer Res., 65(3):1089-1096 (2005).
Holtschke et al., "Immunodeficiency and chronic myelogenous leukemia-like syndrome in mice with a targeted mutation of the ICSBP gene," Cell, 87(2):307-317 (1996).
Hui et al., "T cell costimulatory receptor CD28 is a primary target for PD-1-mediated inhibition," Science, 355(6332):1428-1433 (2017).
Ishijima et al., "Osteopontin is associated with nuclear factor kappaB gene expression during tail-suspension-induced bone loss," Exp Cell Res., 312:3075-3083 (2006).
Jones et al., "Replacing the complementarity-determining regions in a human antibody with those from a mouse," Nature 321:522-525 (1986).
Juneja et al., "PD-L1 on tumor cells is sufficient for immune evasion in immunogenic tumors and inhibits CD8 T cell cytotoxicity," J. Exp. Med., 214(4):895-904 (2017).
Kamphorst et al., "Rescue of exhausted CD8 T cells by PD-1-targeted therapies is CD28-dependent," Science, 355(6332):1423-1427 (2017).
Keir et al., "PD-1 and its ligands in tolerance and immunity," Annu. Rev. Immunol., 26:677-704 (2008).
Kim et al., "Defining and Understanding Adaptive Resistance in Cancer Immunotherapy," Trends Immunol., 39(8):624-631 (2018).
Krueger et al., "Two Strings in One Bow: PD-1 Negatively Regulates via Co-receptor CD28 on T Cells, Immunity," 46(4):529-531 (2017).
Leach et al., "Enhancement of antitumor immunity by CTLA-4 blockade," Science, 271(5256):1734-1736 (1996).
Lesley et al., "Requirements for hyaluronic acid binding by CD44: a role for the cytoplasmic domain and activation by antibody," J. Exp. Med., 175(1):257-266 (1992).
Li et al., "Vascular endothelial growth factor blockade reduces intratumoral regulatory T cells and enhances the efficacy of a GM-CSF-secreting cancer immunotherapy," Clin. Cancer Res., (2006) 12(22):6808-16.
Liang et al., "Design of new oxazaphosphorine anticancer drugs," Curr. Pharm. Des., 13(9):963-78, Review (2007).
Lin et al., "Host expression of PD-L1 determines efficacy of PD-L1 pathway blockade-mediated tumor regression," J. Clin. Invest., 128(2):805-815 (2018).
Lin et al., "The osteopontin-CD44 survival signal involves activation of the phosphatidylinositol 3-kinase/Akt signaling pathway," J. Biol. Chem., 276(49):46024-46030 (2001).
Longberg et al., "Human Antibodies from Transgenic Mice," Int. Rev. Immunol., 13:65-93 (1995).
Machiels et al., "Cyclophosphamide, doxorubicin, and paclitaxel enhance the antitumor immune response of granulocyte/macrophage-colony stimulating factor-secreting whole-cell vaccines in HER-2/neu tolerized mice," Cancer Res., 61:3689-3697 (2001).
Marisa et al., "The Balance Between Cytotoxic T-cell Lymphocytes and Immune Checkpoint Expression in the Prognosis of Colon Tumors," J. Natl. Cancer Inst., 110(1):68-77 (2018).
Mathiowitz et al., "Polyanhydride Mocrospheres as Drug Carriers II," J. Appl. Polymer Sci., 35:755-774 (1988).
Mathiowitz et al., "Novel Microcapsules for Delivery Systems," Reactive Polymers, 6:275-283 (1987).
Mathiowitz et al., "Polyanhydride microspheres as drug carrier. I. Hot-melt microencapsulation," J. Controlled Release, 5:13-22 (1987).
McGough et al., "DNA methylation represses IFN-gamma-induced and signal transducer and activator of transcription 1-mediated IFN regulatory factor 8 activation in colon carcinoma cells," Mol. Cancer Res., 6(12):1841-1851 (2008).
Molnar et al., Crystal structure of the complex between programmed death-1 (PD-1) and its ligand PD-L2, PNAS, 105:10483-10488 (2008).
Morea et al., "Tramontano A. Antibody modeling: implications for engineering and design," Methods, 20(3):267-79 (2000).
Morrison, "Transfectomas provide novel chimeric antibodies," Science, 229:1202 (1985).

\* cited by examiner

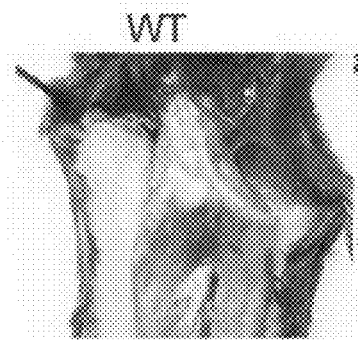
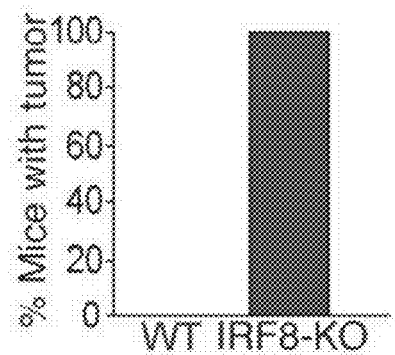
FIG. 1A  FIG. 1B  FIG. 1C
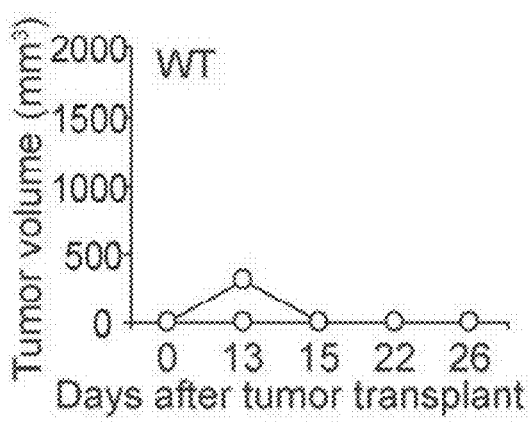
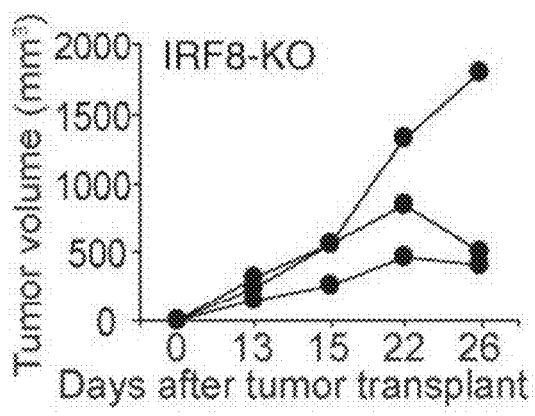
FIG. 1D  FIG. 1E
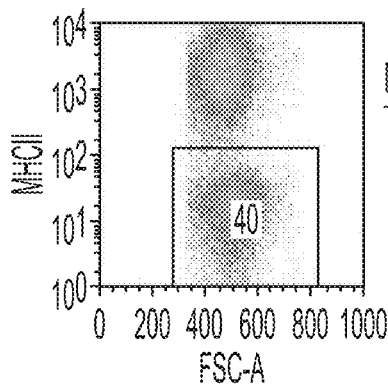
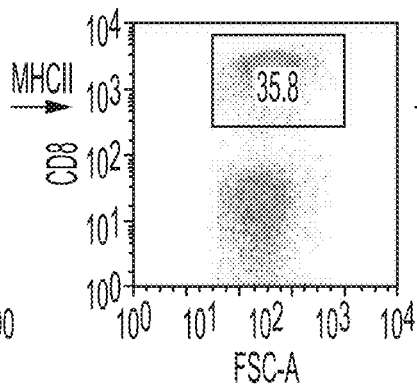
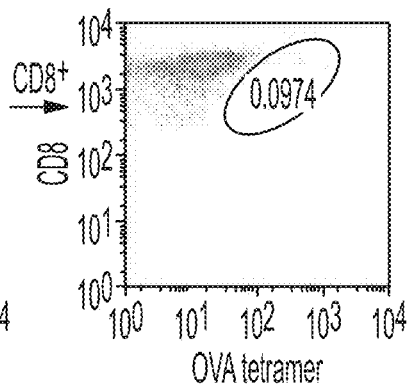
FIG. 1F  FIG. 1G  FIG. 1H

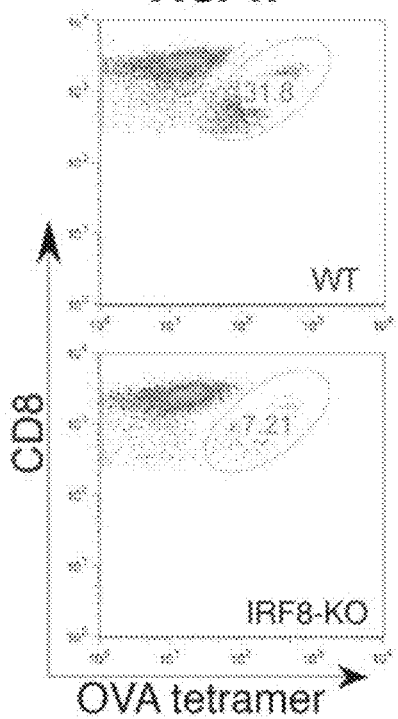
FIG. 1I
FIG. 1J
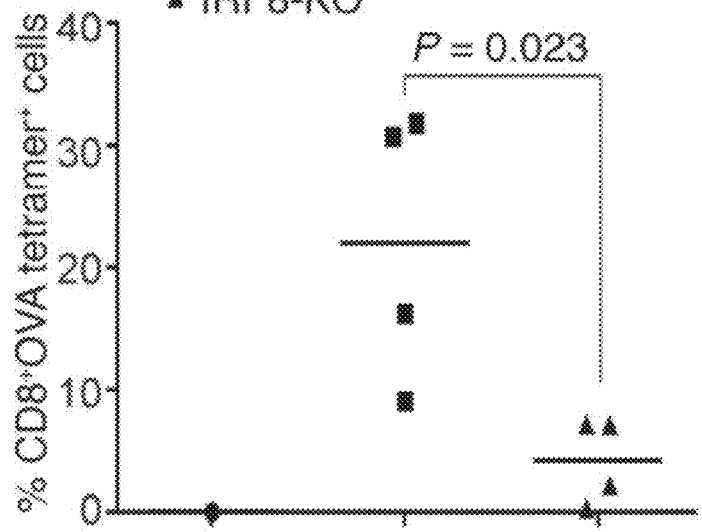
FIG. 1K
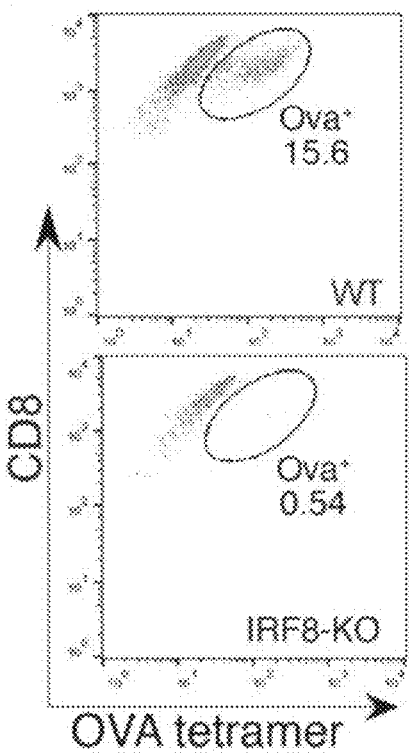
FIG. 1L
FIG. 1M
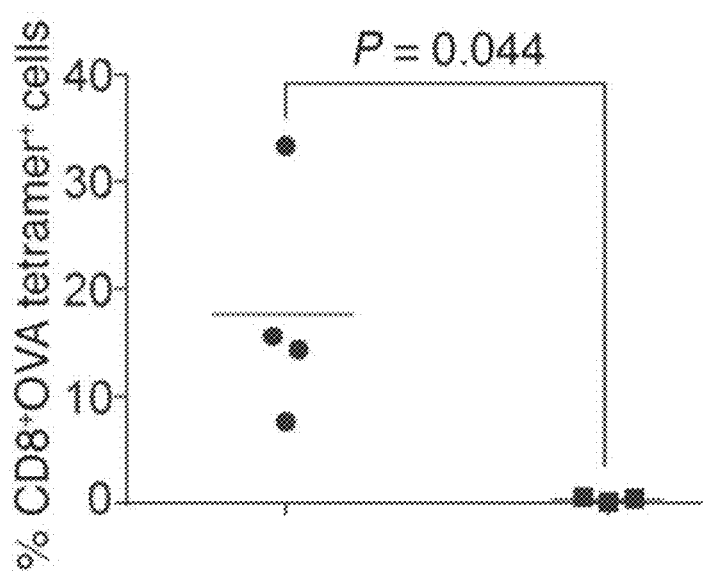
FIG. 1N

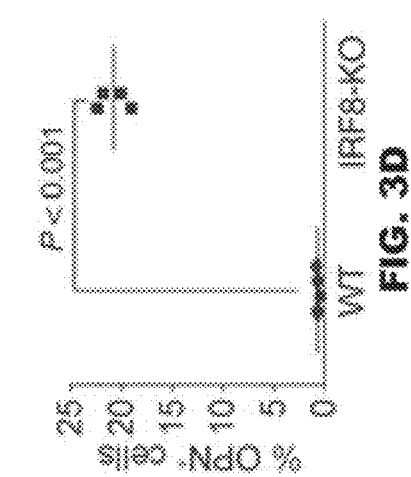
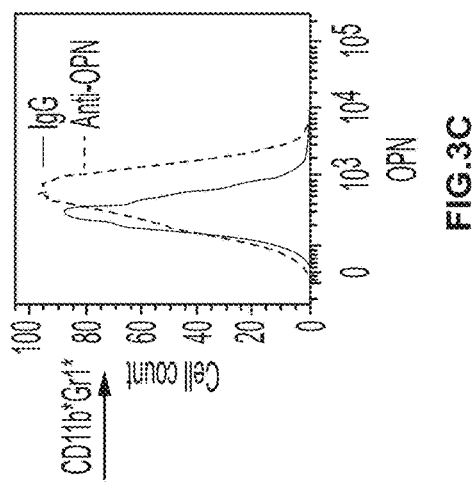
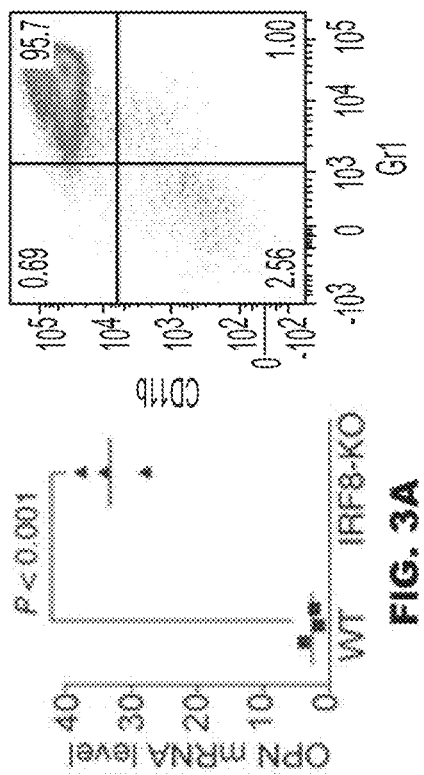
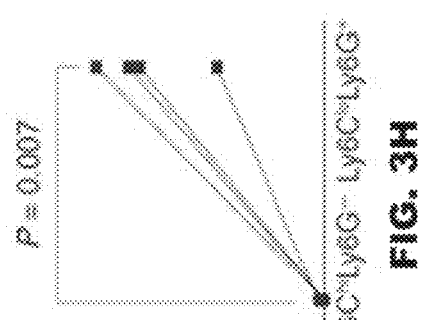
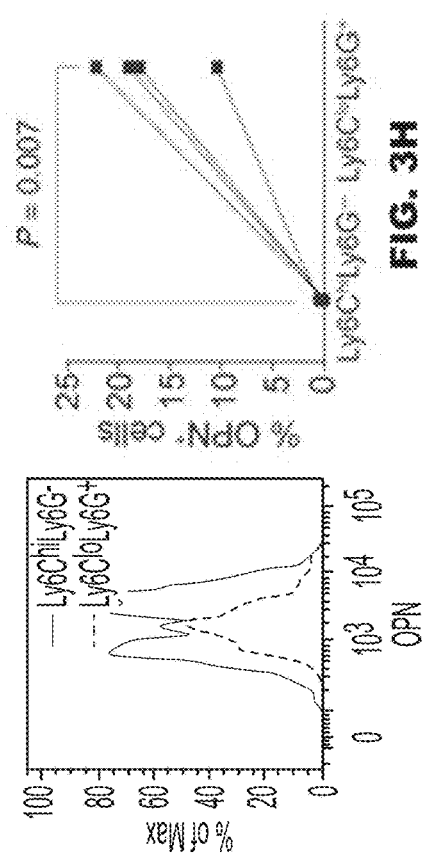
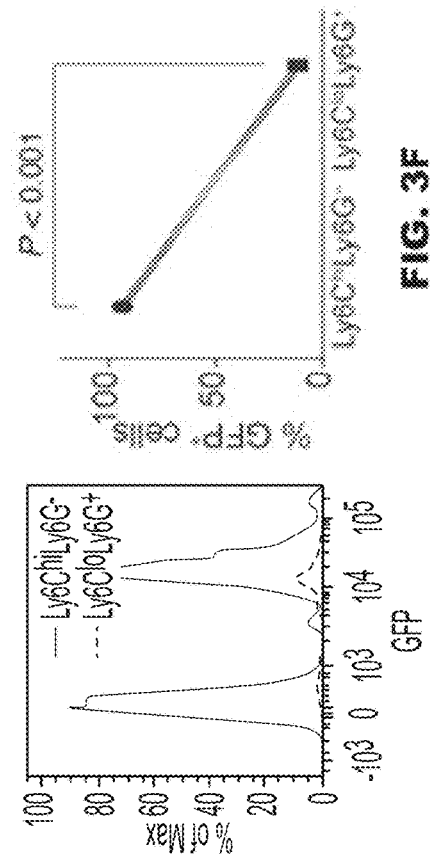

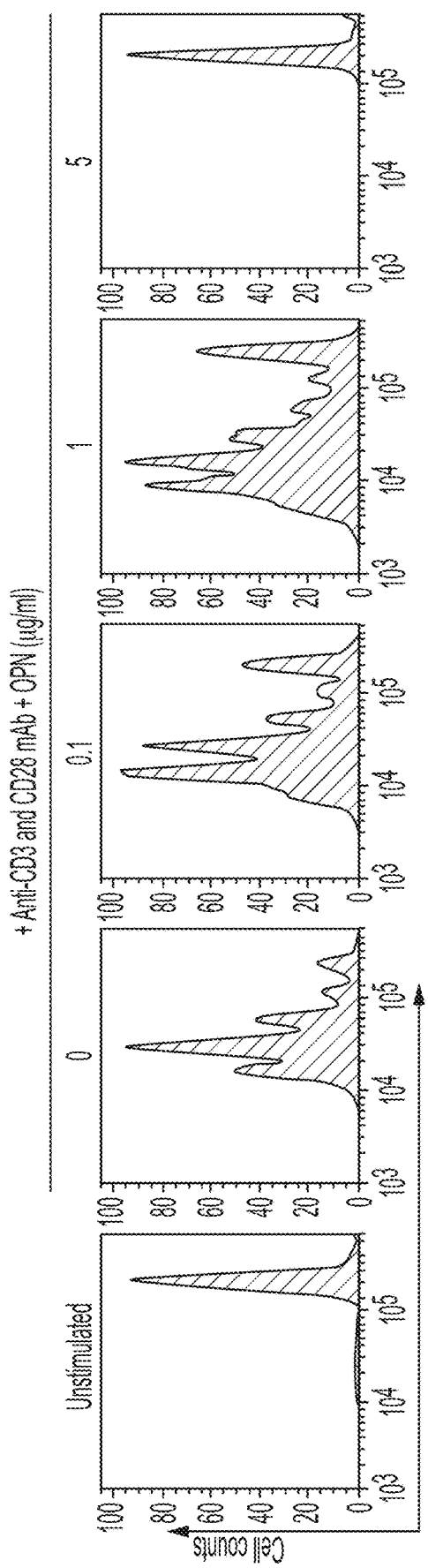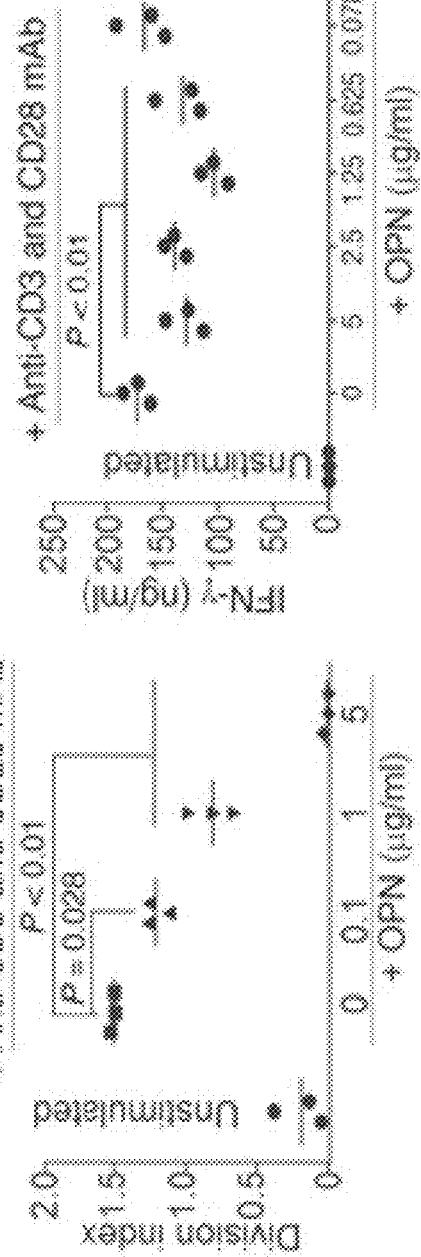

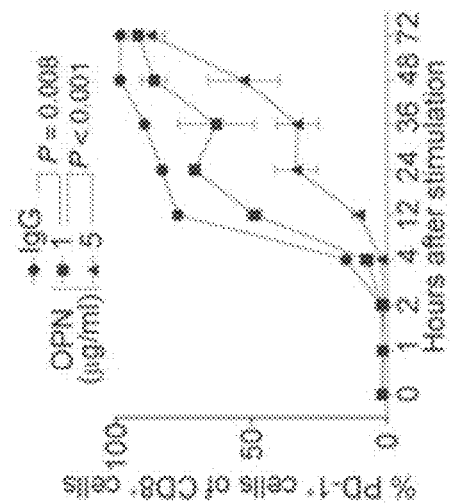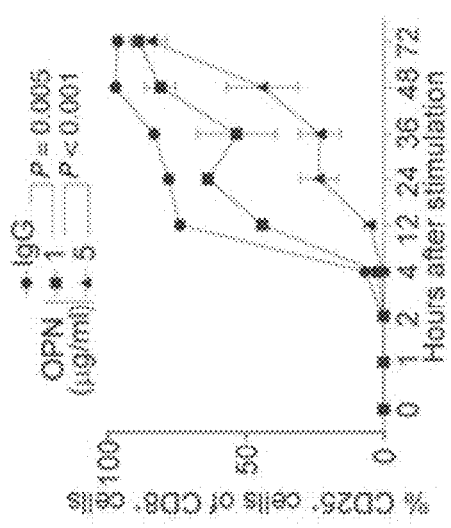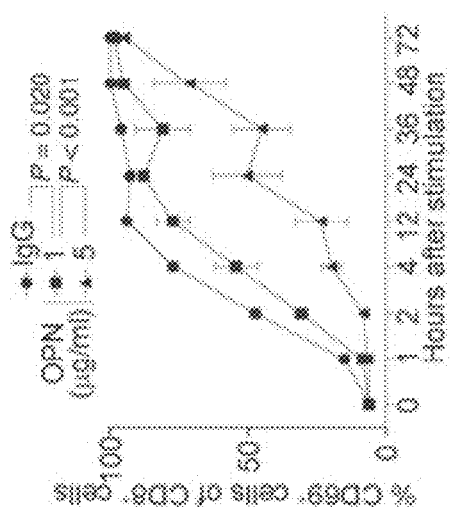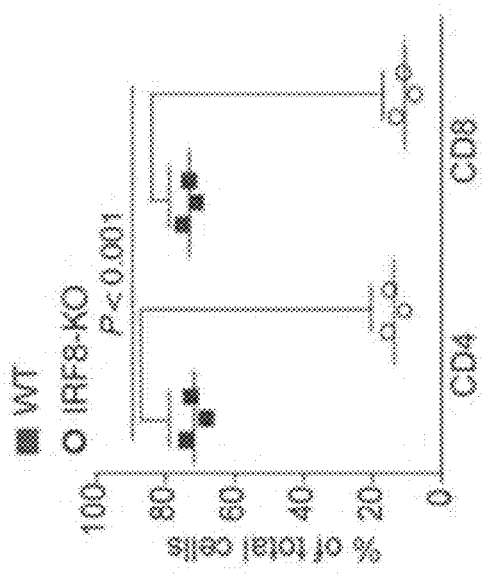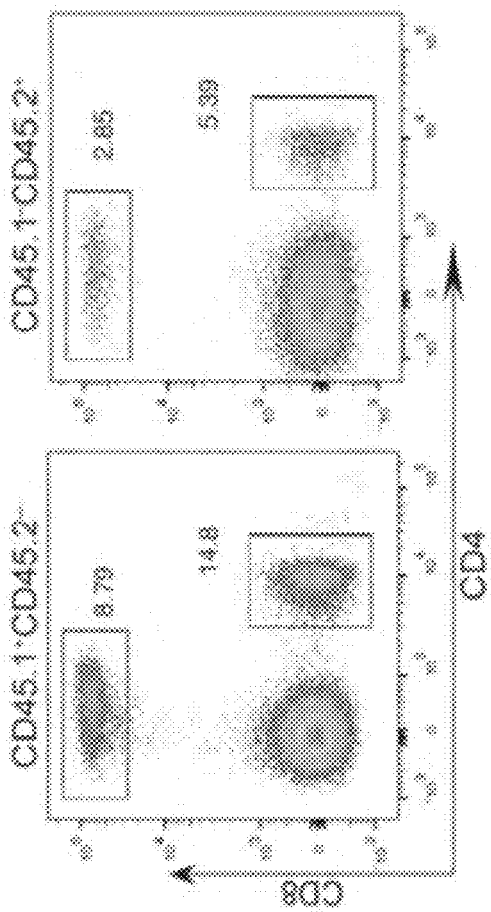

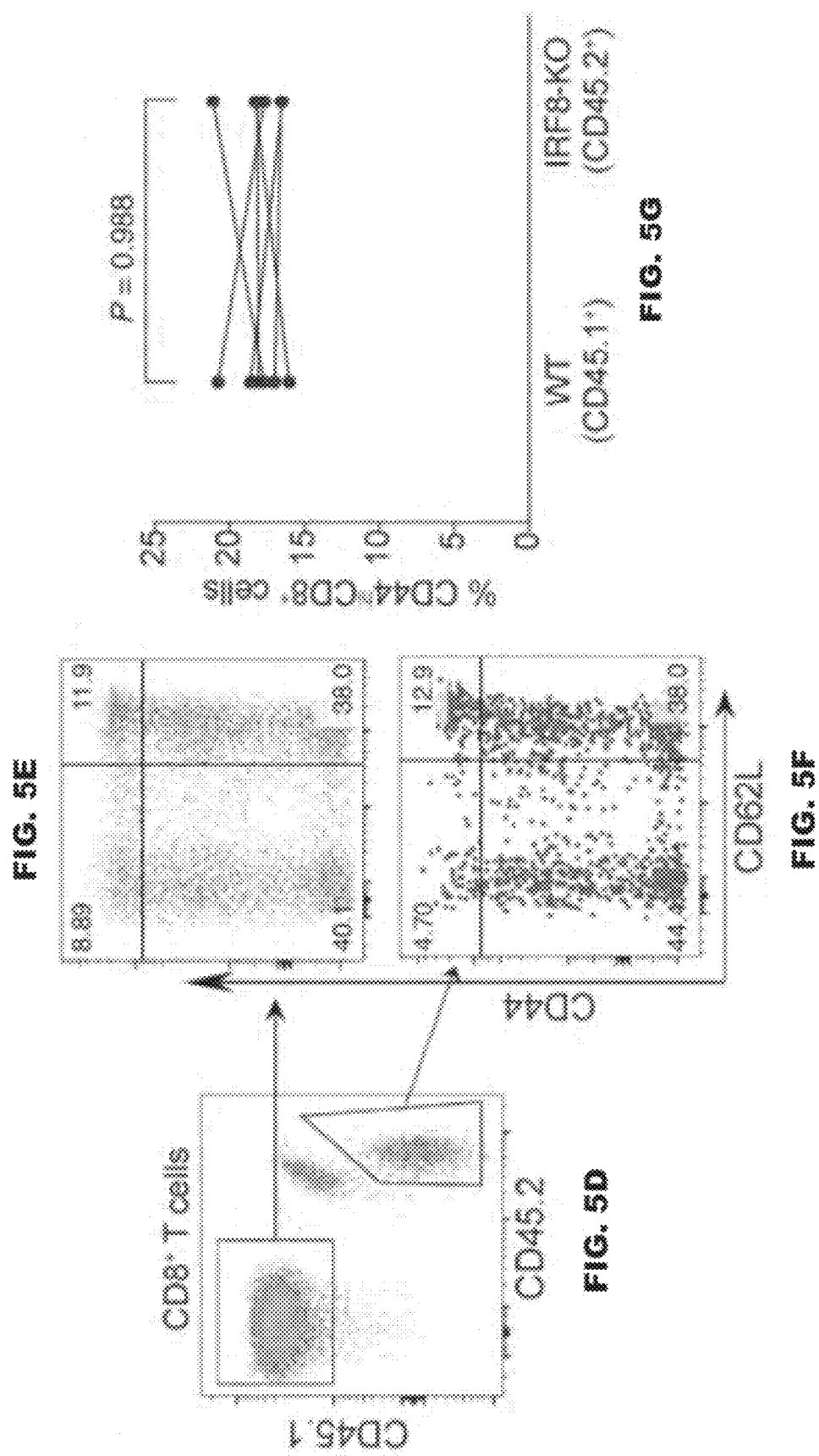

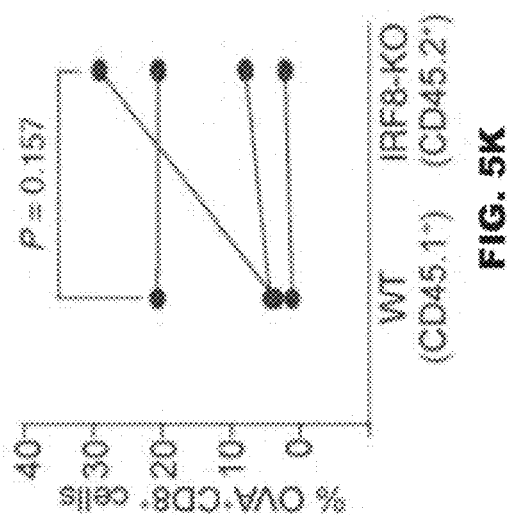
FIG. 5K
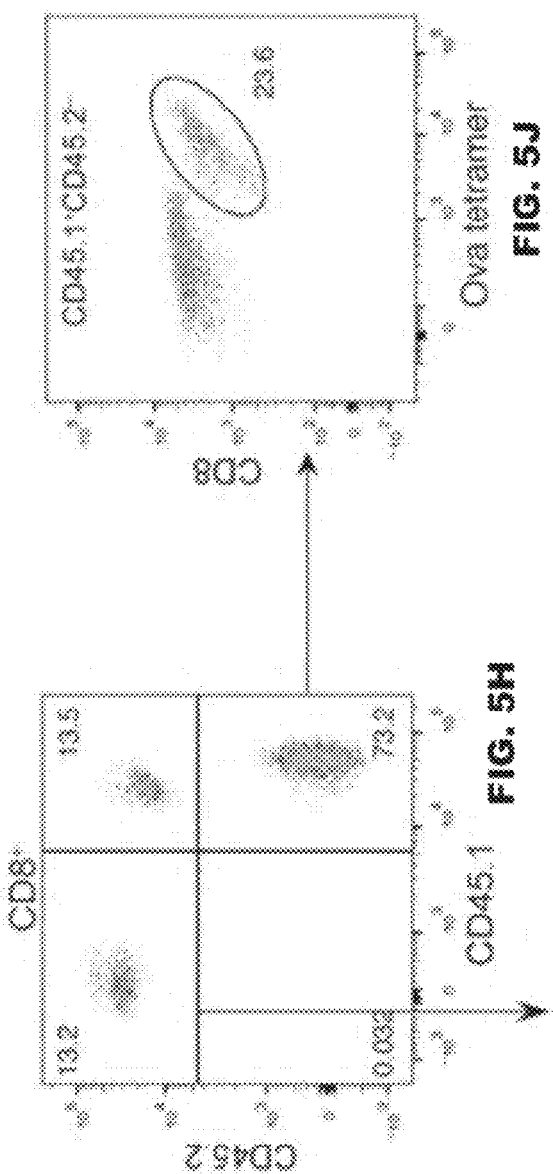
FIG. 5J
FIG. 5H
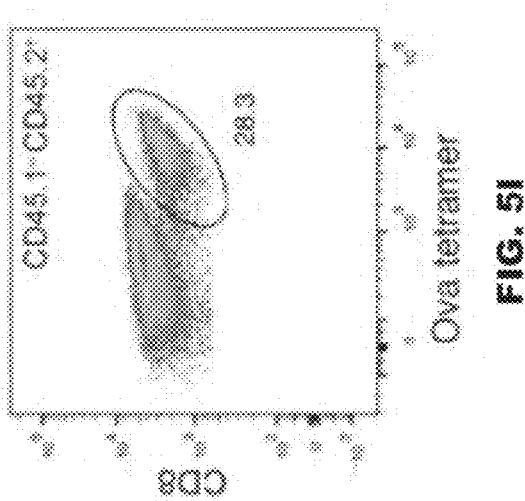
FIG. 5I

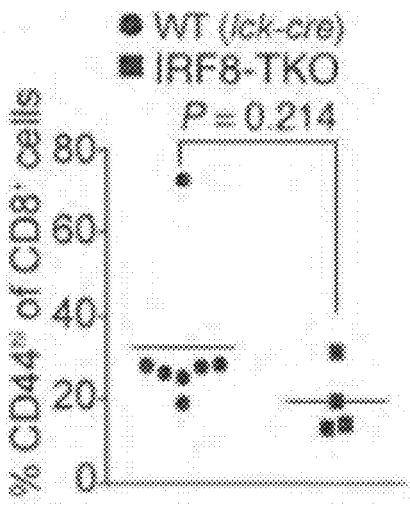 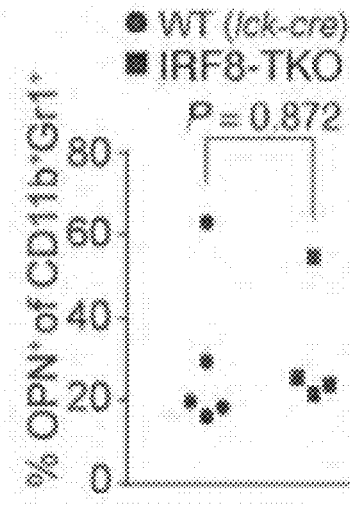 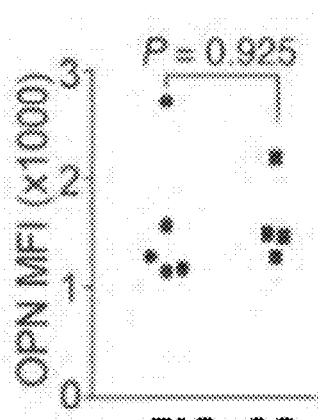
FIG. 6A  FIG. 6B  FIG. 6C
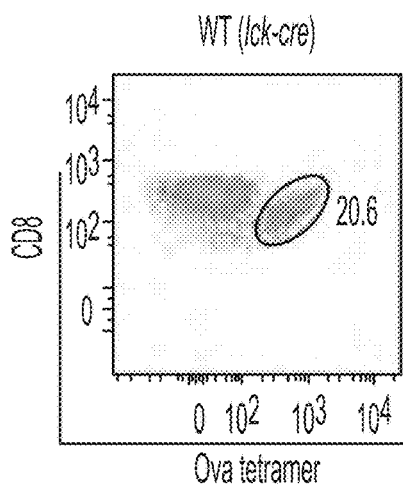 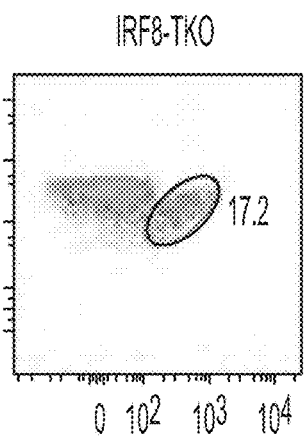 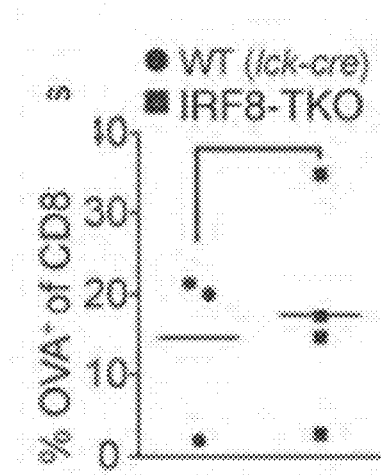
FIG.6D  FIG.6E  FIG. 6F
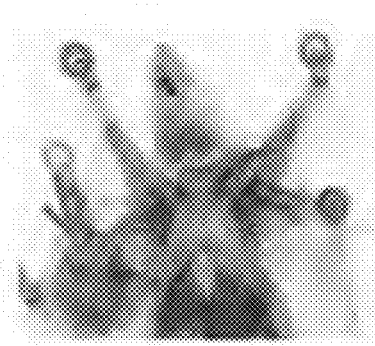 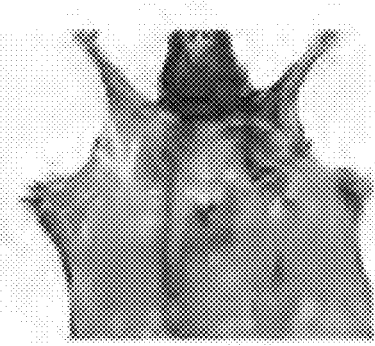 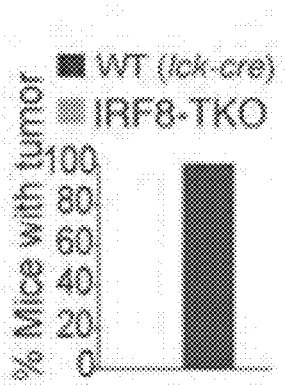
FIG. 6G  FIG. 6H  FIG. 6I

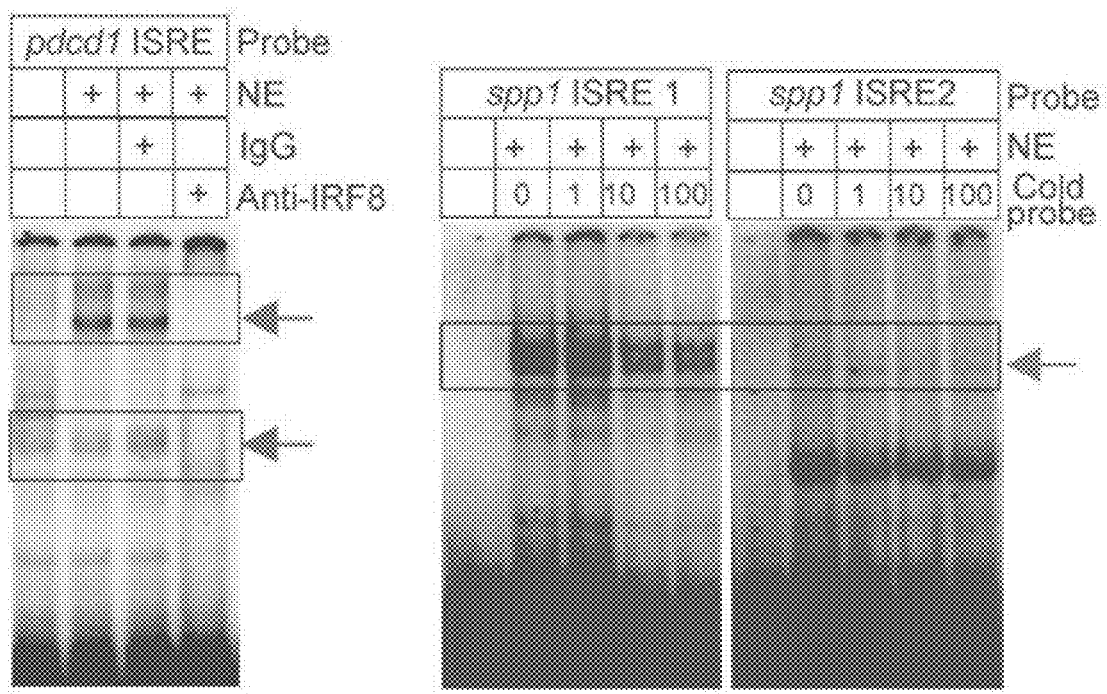
FIG. 7I    FIG. 7J    FIG. 7K
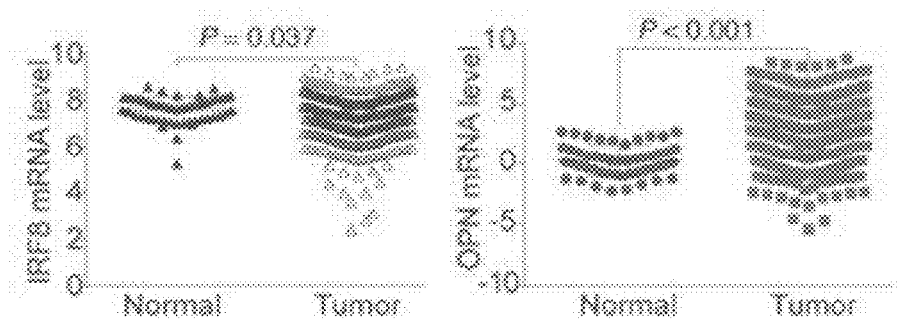
FIG. 8A    FIG. 8B
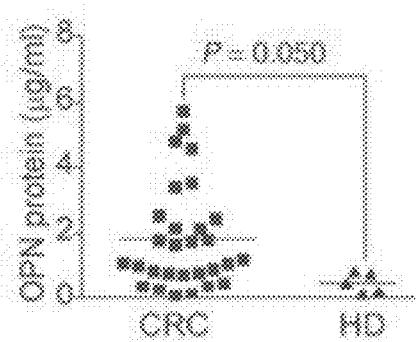
FIG. 8C

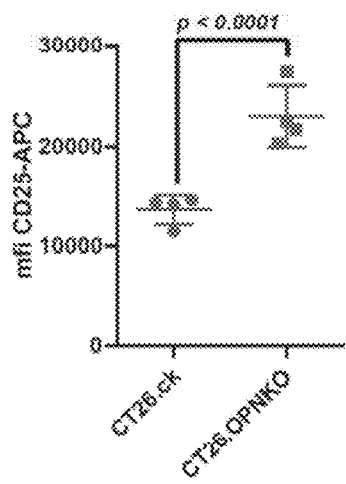
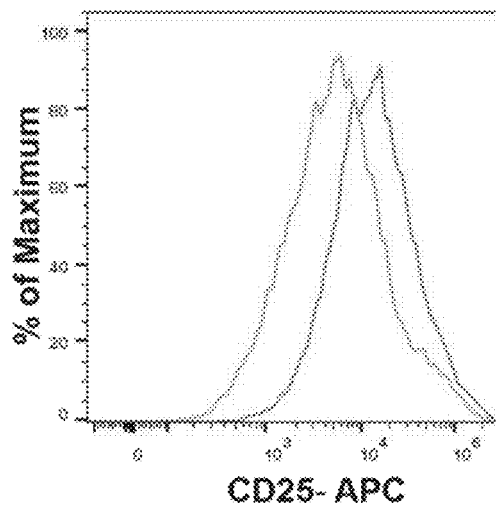
FIG. 11C  FIG. 11D
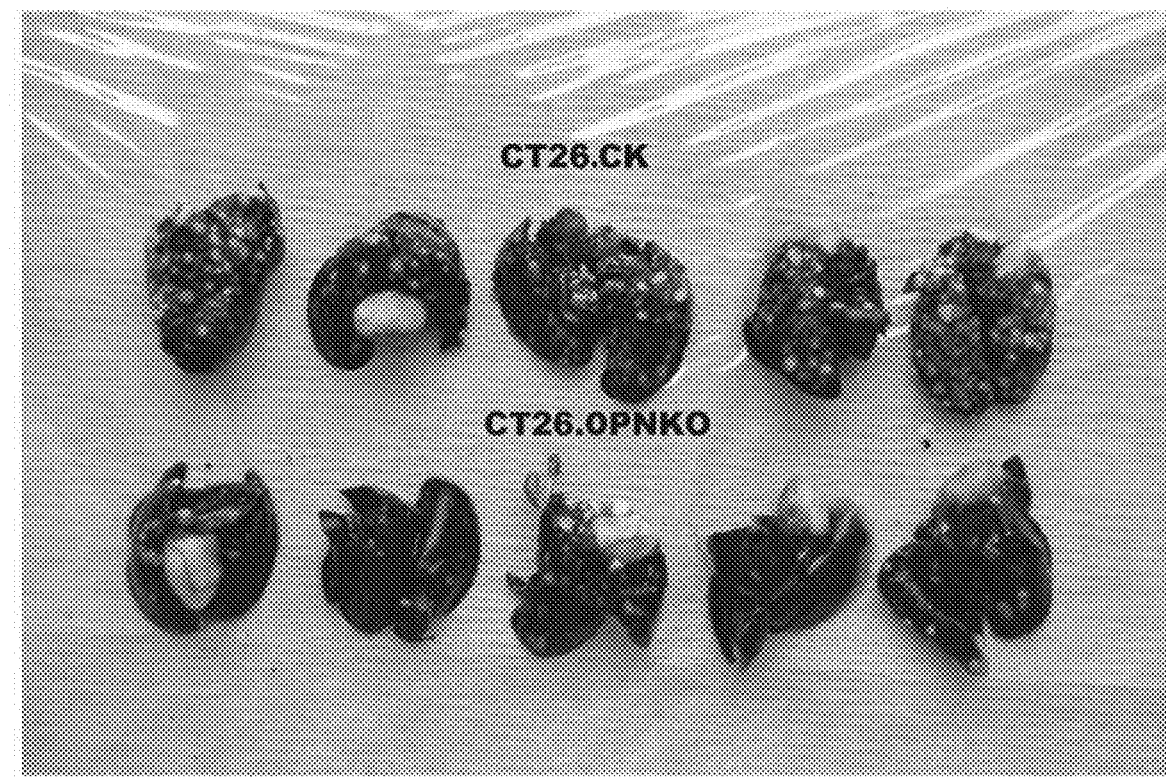
FIG. 11E

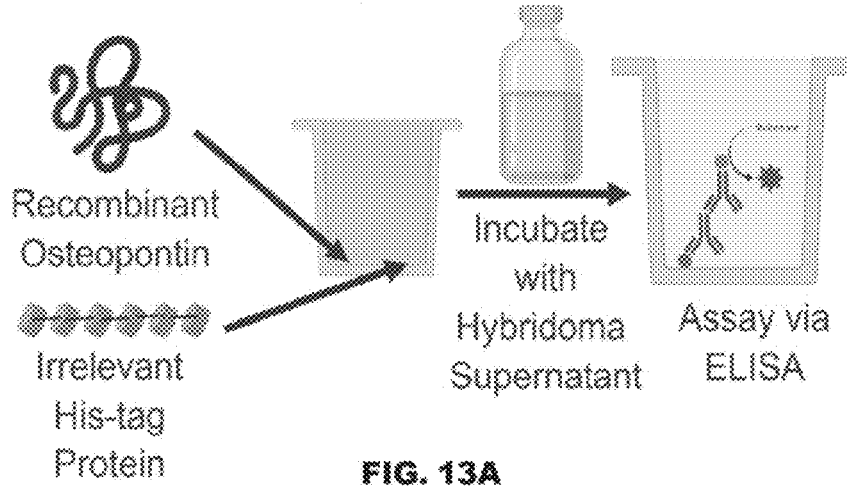
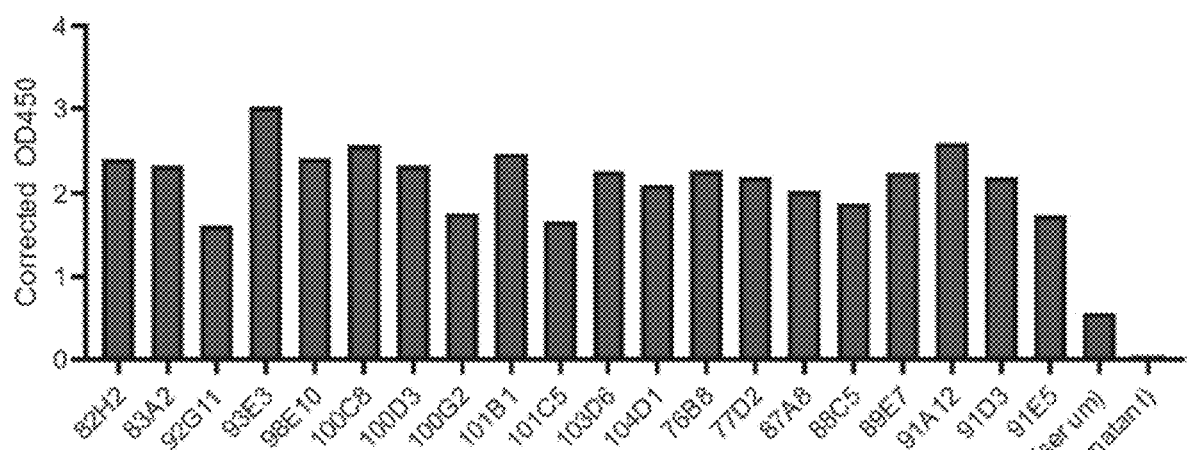
FIG. 13A
FIG. 13B

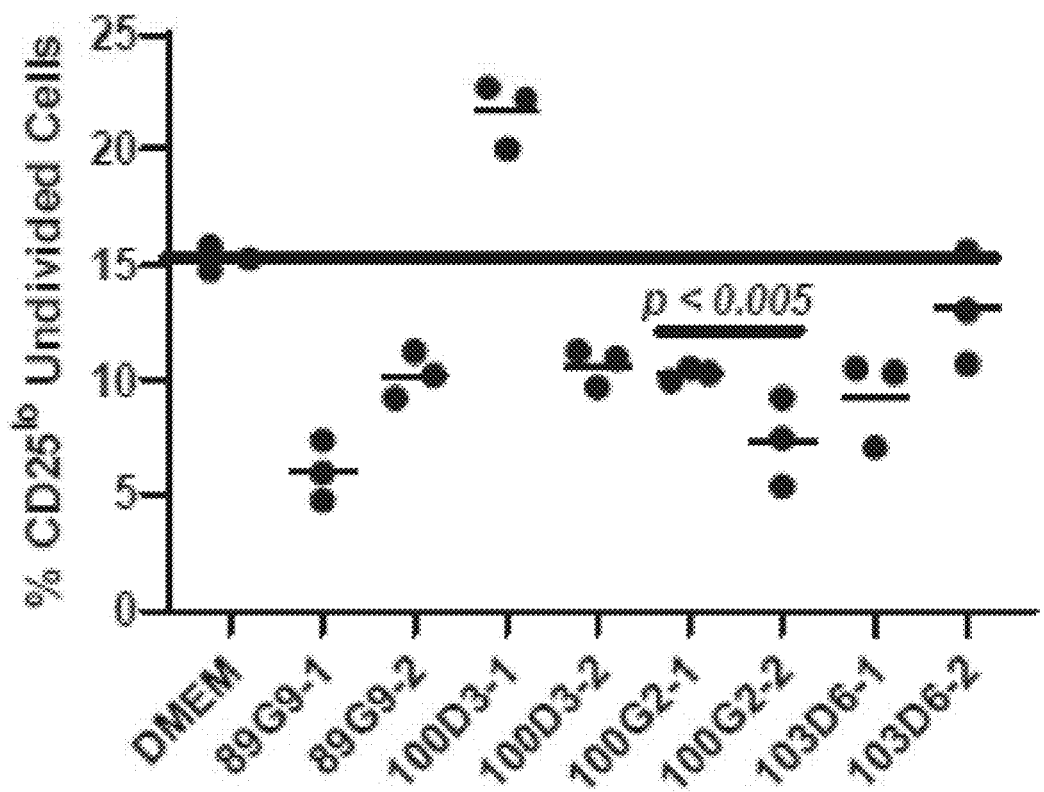
FIG. 14A
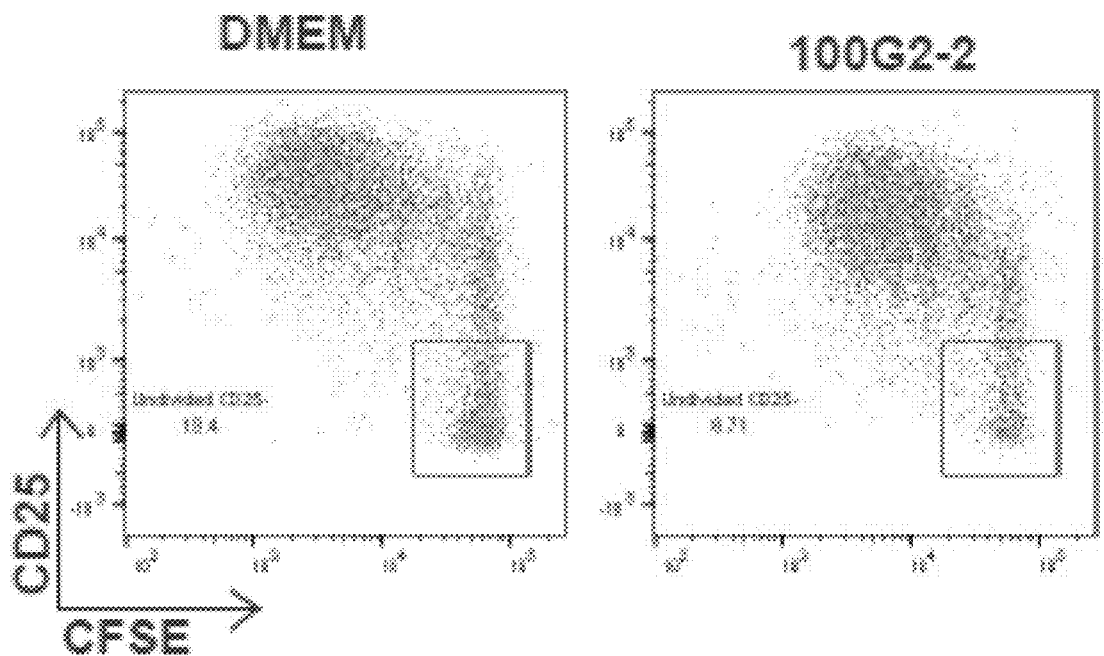
FIG. 14B      FIG. 14C

SEQUENCE LISTING

```
<160> NUMBER OF SEQ ID NOS: 50

<210> SEQ ID NO 1
<211> LENGTH: 314
<212> TYPE: PRT
<213> ORGANISM: Homo sapiens

<400> SEQUENCE: 1

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
```

```
                180                 185                 190
Met Glu Ser Glu Glu Leu Asn Gly Ala Tyr Lys Ala Ile Pro Val Ala
            195                 200                 205
Gln Asp Leu Asn Ala Pro Ser Asp Trp Asp Ser Arg Gly Lys Asp Ser
        210                 215                 220
Tyr Glu Thr Ser Gln Leu Asp Asp Gln Ser Ala Glu Thr His Ser His
225                 230                 235                 240
Lys Gln Ser Arg Leu Tyr Lys Arg Lys Ala Asn Asp Glu Ser Asn Glu
                245                 250                 255
His Ser Asp Val Ile Asp Ser Gln Glu Leu Ser Lys Val Ser Arg Glu
            260                 265                 270
Phe His Ser His Glu Phe His Ser His Glu Asp Met Leu Val Val Asp
        275                 280                 285
Pro Lys Ser Lys Glu Glu Asp Lys His Leu Lys Phe Arg Ile Ser His
        290                 295                 300
Glu Leu Asp Ser Ala Ser Ser Glu Val Asn
305                 310

<210> SEQ ID NO 2
<211> LENGTH: 300
<212> TYPE: PRT
<213> ORGANISM: Homo sapiens

<400> SEQUENCE: 2

Met Arg Ile Ala Val Ile Cys Phe Cys Leu Leu Gly Ile Thr Cys Ala
1               5                   10                  15
Ile Pro Val Lys Gln Ala Asp Ser Gly Ser Ser Glu Glu Lys Gln Leu
            20                  25                  30
Tyr Asn Lys Tyr Pro Asp Ala Val Ala Thr Trp Leu Asn Pro Asp Pro
        35                  40                  45
Ser Gln Lys Gln Asn Leu Leu Ala Pro Glu Thr Leu Pro Ser Lys Ser
    50                  55                  60
Asn Glu Ser His Asp His Met Asp Asp Met Asp Asp Glu Asp Asp Asp
65                  70                  75                  80
Asp His Val Asp Ser Gln Asp Ser Ile Asp Ser Asn Asp Ser Asp Asp
                85                  90                  95
Val Asp Asp Thr Asp Asp Ser His Gln Ser Asp Glu Ser His His Ser
            100                 105                 110
Asp Glu Ser Asp Glu Leu Val Thr Asp Phe Pro Thr Asp Leu Pro Ala
        115                 120                 125
Thr Glu Val Phe Thr Pro Val Val Pro Thr Val Asp Thr Tyr Asp Gly
    130                 135                 140
Arg Gly Asp Ser Val Val Tyr Gly Leu Arg Ser Lys Ser Lys Lys Phe
145                 150                 155                 160
Arg Arg Pro Asp Ile Gln Tyr Pro Asp Ala Thr Asp Glu Asp Ile Thr
                165                 170                 175
Ser His Met Glu Ser Glu Glu Leu Asn Gly Ala Tyr Lys Ala Ile Pro
            180                 185                 190
Val Ala Gln Asp Leu Asn Ala Pro Ser Asp Trp Asp Ser Arg Gly Lys
        195                 200                 205
Asp Ser Tyr Glu Thr Ser Gln Leu Asp Asp Gln Ser Ala Glu Thr His
    210                 215                 220
Ser His Lys Gln Ser Arg Leu Tyr Lys Arg Lys Ala Asn Asp Glu Ser
225                 230                 235                 240
```

```
Asn Glu His Ser Asp Val Ile Asp Ser Gln Glu Leu Ser Lys Val Ser
                245                 250                 255

Arg Glu Phe His Ser His Glu Phe His Ser His Glu Asp Met Leu Val
                260                 265                 270

Val Asp Pro Lys Ser Lys Glu Glu Asp Lys His Leu Lys Phe Arg Ile
                275                 280                 285

Ser His Glu Leu Asp Ser Ala Ser Ser Glu Val Asn
                290                 295                 300

<210> SEQ ID NO 3
<211> LENGTH: 287
<212> TYPE: PRT
<213> ORGANISM: Homo sapiens

<400> SEQUENCE: 3

Met Arg Ile Ala Val Ile Cys Phe Cys Leu Leu Gly Ile Thr Cys Ala
  1               5                  10                  15

Ile Pro Val Lys Gln Ala Asp Ser Gly Ser Ser Glu Glu Lys Gln Asn
                 20                  25                  30

Ala Val Ser Ser Glu Glu Thr Asn Asp Phe Lys Gln Glu Thr Leu Pro
                 35                  40                  45

Ser Lys Ser Asn Glu Ser His Asp His Met Asp Asp Met Asp Asp Glu
 50                  55                  60

Asp Asp Asp Asp His Val Asp Ser Gln Asp Ser Ile Asp Ser Asn Asp
 65                  70                  75                  80

Ser Asp Asp Val Asp Asp Thr Asp Asp Ser His Gln Ser Asp Glu Ser
                 85                  90                  95

His His Ser Asp Glu Ser Asp Glu Leu Val Thr Asp Phe Pro Thr Asp
                100                 105                 110

Leu Pro Ala Thr Glu Val Phe Thr Pro Val Val Pro Thr Val Asp Thr
                115                 120                 125

Tyr Asp Gly Arg Gly Asp Ser Val Val Tyr Gly Leu Arg Ser Lys Ser
                130                 135                 140

Lys Lys Phe Arg Arg Pro Asp Ile Gln Tyr Pro Asp Ala Thr Asp Glu
145                 150                 155                 160

Asp Ile Thr Ser His Met Glu Ser Glu Glu Leu Asn Gly Ala Tyr Lys
                165                 170                 175

Ala Ile Pro Val Ala Gln Asp Leu Asn Ala Pro Ser Asp Trp Asp Ser
                180                 185                 190

Arg Gly Lys Asp Ser Tyr Glu Thr Ser Gln Leu Asp Asp Gln Ser Ala
                195                 200                 205

Glu Thr His Ser His Lys Gln Ser Arg Leu Tyr Lys Arg Lys Ala Asn
                210                 215                 220

Asp Glu Ser Asn Glu His Ser Asp Val Ile Asp Ser Gln Glu Leu Ser
225                 230                 235                 240

Lys Val Ser Arg Glu Phe His Ser His Glu Phe His Ser His Glu Asp
                245                 250                 255

Met Leu Val Val Asp Pro Lys Ser Lys Glu Glu Asp Lys His Leu Lys
                260                 265                 270

Phe Arg Ile Ser His Glu Leu Asp Ser Ala Ser Ser Glu Val Asn
                275                 280                 285

<210> SEQ ID NO 4
<211> LENGTH: 292
<212> TYPE: PRT
<213> ORGANISM: Homo sapiens
```

```
<400> SEQUENCE: 4

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Glu Asp Asp Asp Ser His
                85                  90                  95

Gln Ser Asp Glu Ser His His Ser Asp Glu Ser Asp Glu Leu Val Thr
                100                 105                 110

Asp Phe Pro Thr Asp Leu Pro Ala Thr Glu Val Phe Thr Pro Val Val
            115                 120                 125

Pro Thr Val Asp Thr Tyr Asp Gly Arg Gly Asp Ser Val Val Tyr Gly
130                 135                 140

Leu Arg Ser Lys Ser Lys Lys Phe Arg Arg Pro Asp Ile Gln Tyr Pro
145                 150                 155                 160

Asp Ala Thr Asp Glu Asp Ile Thr Ser His Met Glu Ser Glu Glu Leu
                165                 170                 175

Asn Gly Ala Tyr Lys Ala Ile Pro Val Ala Gln Asp Leu Asn Ala Pro
            180                 185                 190

Ser Asp Trp Asp Ser Arg Gly Lys Asp Ser Tyr Glu Thr Ser Gln Leu
        195                 200                 205

Asp Asp Gln Ser Ala Glu Thr His Ser His Lys Gln Ser Arg Leu Tyr
    210                 215                 220

Lys Arg Lys Ala Asn Asp Glu Ser Asn Glu His Ser Asp Val Ile Asp
225                 230                 235                 240

Ser Gln Glu Leu Ser Lys Val Ser Arg Glu Phe His Ser His Glu Phe
                245                 250                 255

His Ser His Glu Asp Met Leu Val Val Asp Pro Lys Ser Lys Glu Glu
            260                 265                 270

Asp Lys His Leu Lys Phe Arg Ile Ser His Glu Leu Asp Ser Ala Ser
        275                 280                 285

Ser Glu Val Asn
    290

<210> SEQ ID NO 5
<211> LENGTH: 300
<212> TYPE: PRT
<213> ORGANISM: Homo sapiens

<400> SEQUENCE: 5

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Thr Leu Pro Ser Lys Ser
    50                  55                  60
```

Asn Glu Ser His Asp His Met Asp Asp Met Asp Glu Asp Asp
65                  70                  75                  80

Asp His Val Asp Ser Gln Asp Ser Ile Asp Ser Asn Asp Ser Asp Asp
                85                  90                  95

Val Asp Asp Thr Asp Asp Ser His Gln Ser Asp Glu Ser His His Ser
            100                 105                 110

Asp Glu Ser Asp Glu Leu Val Thr Asp Phe Pro Thr Asp Leu Pro Ala
        115                 120                 125

Thr Glu Val Phe Thr Pro Val Pro Thr Val Asp Thr Tyr Asp Gly
    130                 135                 140

Arg Gly Asp Ser Val Val Tyr Gly Leu Arg Ser Lys Ser Lys Lys Phe
145                 150                 155                 160

Arg Arg Pro Asp Ile Gln Tyr Pro Asp Ala Thr Asp Glu Asp Ile Thr
                165                 170                 175

Ser His Met Glu Ser Glu Glu Leu Asn Gly Ala Tyr Lys Ala Ile Pro
            180                 185                 190

Val Ala Gln Asp Leu Asn Ala Pro Ser Asp Trp Asp Ser Arg Gly Lys
        195                 200                 205

Asp Ser Tyr Glu Thr Ser Gln Leu Asp Asp Gln Ser Ala Glu Thr His
    210                 215                 220

Ser His Lys Gln Ser Arg Leu Tyr Lys Arg Lys Ala Asn Asp Glu Ser
225                 230                 235                 240

Asn Glu His Ser Asp Val Ile Asp Ser Gln Glu Leu Ser Lys Val Ser
                245                 250                 255

Arg Glu Phe His Ser His Glu Phe Ser His Glu Asp Met Leu Val
            260                 265                 270

Val Asp Pro Lys Ser Lys Glu Glu Asp Lys His Leu Lys Phe Arg Ile
        275                 280                 285

Ser His Glu Leu Asp Ser Ala Ser Ser Glu Val Asn
    290                 295                 300

<210> SEQ ID NO 6
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Lys Leu Pro Val Arg Leu Leu Val Leu Met Phe Trp Ile Pro Ala
1               5                   10                  15

Ser Asn Ser Asp Val Val Met Thr Gln Thr Pro Leu Ser Leu Pro Val
            20                  25                  30

Arg Leu Gly Asp Gln Ala Ser Ile Ser Cys Arg Pro Ser Gln Ser Ile
        35                  40                  45

Val His Gly Asn Arg Lys Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Arg Ser Gly Thr Asp Phe Thr
                85                  90                  95

Leu Lys Ile Ser Arg Val Glu Ala Ala Asp Leu Gly Val Tyr Tyr Cys
            100                 105                 110

Phe Gln Gly Ser His Val Pro Trp Thr Phe Gly Gly Gly Thr Lys Leu

Glu Ile Lys
    130

<210> SEQ ID NO 7
<211> LENGTH: 141
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 7

Met Glu Trp Ser Trp Val Phe Leu Phe Leu Leu Ser Val Ile Ala Gly
1               5                   10                  15

Val Gln Ser Gln Val His Leu Gln Gln Ser Gly Ala Asp Leu Val Arg
            20                  25                  30

Pro Gly Ala Ser Val Thr Leu Ser Cys Lys Ala Ser Gly Tyr Thr Phe
        35                  40                  45

Thr Asp Phe Glu Met His Trp Val Lys Gln Thr Pro Val His Gly Leu
    50                  55                  60

Asp Trp Ile Gly Ala Ile Asp Pro Glu Thr Gly Ser Thr Gly Tyr Asn
65                  70                  75                  80

Gln Lys Phe Lys Asp Lys Ala Ile Leu Thr Ala Asp Arg Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Ala Tyr Tyr Asn Asn Tyr Arg Asp Tyr Ala Met
        115                 120                 125

Asp Tyr Trp Gly Gln Gly Thr Ser Val Ala Val Ser Ser
    130                 135                 140

<210> SEQ ID NO 8
<211> LENGTH: 131
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 8

Met Ser Pro Ala Gln Phe Leu Ile Leu Leu Val Leu Trp Ile Arg Glu
1               5                   10                  15

Thr Asn Gly Asp Val Val Met Thr Gln Thr Pro Leu Thr Leu Ser Val
            20                  25                  30

Thr Ile Gly Arg Pro Ala Ser Ile Ser Cys Lys Ser Ser Gln Ser Leu
        35                  40                  45

Leu Glu Ser Asp Gly Lys Thr Tyr Leu Asn Trp Leu Leu Gln Arg Pro
    50                  55                  60

Gly Gln Ser Pro Lys Arg Leu Ile Tyr Leu Val Ser Lys Leu Asp Ser
65                  70                  75                  80

Gly Val Pro Asp Arg Phe Thr Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Trp Gln Gly Thr His Phe Pro Arg Thr Phe Gly Gly Gly Thr Lys Leu
        115                 120                 125

Glu Ile Lys

<210> SEQ ID NO 9
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Gly Trp Ser Cys Ile Met Leu Phe Leu Ala Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Arg Gly Leu
    50                  55                  60

Glu Trp Ile Gly Arg Ile Val Pro Lys Ser Gly Asp Thr Lys Tyr Asn
65                  70                  75                  80

Glu Lys Phe Lys Ser Lys Ala Thr Leu Thr Val Asp Lys Pro Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Glu Ser Gly Tyr Trp Gly Gln Gly Thr Thr Leu
        115                 120                 125

Thr Val Ser Ser
    130
```

<210> SEQ ID NO 10
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Arg Phe Ser Ala Gln Leu Leu Gly Leu Leu Val Leu Trp Ile Pro
1               5                   10                  15

Gly Ser Thr Ala Glu Ile Val Met Thr Gln Ala Ala Phe Ser Lys Pro
            20                  25                  30

Val Thr Leu Gly Thr Ser Ala Ser Ile Ser Cys Arg Ser Ser Lys Ser
        35                  40                  45

Leu Leu Gln Arg Asn Gly Ile Thr Tyr Leu Cys Trp Phe Leu Gln Arg
    50                  55                  60

Pro Gly Gln Ser Pro Gln Leu Leu Ile Tyr Gln Met Ser Asn Leu Ala
65                  70                  75                  80

Ser Gly Val Pro Asp Arg Phe Ser Cys Ser Gly Ser Gly Thr Glu Phe
                85                  90                  95

Thr Leu Arg Ile Ser Arg Val Glu Ala Glu Asp Val Gly Val Tyr Tyr
            100                 105                 110

Cys Ala Gln Asp Leu Glu Leu Pro Pro Thr Phe Gly Gly Gly Thr Lys
        115                 120                 125

Leu Glu Ile Arg
    130
```

```
<210> SEQ ID NO 11
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asp Ser Arg Leu Asn Leu Val Phe Leu Val Leu Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Gly Met His Phe Val Arg Gln Ala Pro Glu Arg Gly Leu
    50                  55                  60

Glu Trp Val Ala Tyr Ile Asn Ser Arg Ser Asp Thr Ile Tyr Tyr Val
65                  70                  75                  80

Asp Thr Val Lys Gly Arg Phe Thr Ile Ser Arg Asp Asn Ala Lys Asn
                85                  90                  95

Thr Leu Phe Leu Gln Met Thr Ser Leu Arg Ser Glu Asp Thr Ala Ile
            100                 105                 110

Tyr Tyr Cys Ala Arg Glu Tyr Tyr Gly Met Asp Tyr Trp Gly Gln Gly
        115                 120                 125

Thr Ser Val Thr Val Ser Ser
    130                 135

<210> SEQ ID NO 12
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Arg Phe Ser Ala Gln Leu Leu Gly Leu Leu Val Leu Trp Ile Pro
1               5                   10                  15

Gly Ser Thr Ala Asp Ile Val Met Thr Gln Ala Ala Phe Ser Asn Pro
            20                  25                  30

Val Thr Leu Gly Thr Ser Ala Ser Ile Ser Cys Arg Ser Ser Lys Ser
        35                  40                  45

Leu Leu His Thr Asn Gly Ile Thr Tyr Leu Tyr Trp Phe Leu Gln Lys
    50                  55                  60

Pro Gly Gln Ser Pro Gln Leu Leu Ile Tyr Gln Met Ser Asn Leu Ala
65                  70                  75                  80

Ser Gly Val Pro Asp Arg Phe Ser Ser Gly Ser Gly Thr Asp Phe
                85                  90                  95

Thr Leu Arg Ile Ser Arg Val Glu Ala Glu Asp Val Gly Val Tyr Tyr
            100                 105                 110

Cys Ala Gln Asn Leu Glu Leu Pro Pro Thr Phe Gly Gly Gly Thr Lys
        115                 120                 125

Leu Glu Ile Lys
    130

<210> SEQ ID NO 13
<211> LENGTH: 135
<212> TYPE: PRT
```

-continued

<213> ORGANISM: Artificial Sequence
<220> FEATURE:
<223> OTHER INFORMATION: Description of Artificial Sequence: Synthetic
      polypeptide

<400> SEQUENCE: 13

Met Asp Ser Arg Leu Asn Leu Val Phe Leu Val Leu Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Val Val Ser Gly Phe Thr Phe
        35                  40                  45

Asn Asn Tyr Glu Met His Trp Val Arg Leu Ala Pro Glu Lys Gly Leu
    50                  55                  60

Glu Trp Ile Ala Tyr Ile Asn Ser Gly Ser Arg Thr Ile Tyr Tyr Ala
65                  70                  75                  80

Asp Thr Val Lys Gly Arg Phe Thr Ile Ser Arg Asp Asn Ala Lys Asn
                85                  90                  95

Ile Leu Phe Leu Gln Met Thr Asn Leu Arg Ser Glu Asp Thr Ala Met
            100                 105                 110

Tyr Tyr Cys Thr Arg Tyr Tyr His Ala Met Asp Tyr Trp Gly Gln Gly
        115                 120                 125

Thr Ser Val Thr Val Ser Ser
        130                 135

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Pro Ser Gln Ser Ile Val His Gly Asn Arg Lys Thr Tyr Leu Glu
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Val Ser Asn Arg Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Gln Gly Ser His Val Pro Trp Thr
1               5

<210> SEQ ID NO 17
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Phe Glu Met His
1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ile Asp Pro Glu Thr Gly Ser Thr Gly Tyr Asn Gln Lys Phe Lys
1               5                   10                  15

Asp

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Tyr Tyr Asn Asn Tyr Arg Asp Tyr Ala Met Asp Tyr
1               5                   10

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Ser Ser Gln Ser Leu Leu Glu Ser Asp Gly Lys Thr Tyr Leu Asn
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Val Ser Lys Leu Asp Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22
```

```
Trp Gln Gly Thr His Phe Pro Arg Thr
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Tyr Trp Met His
1               5

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ile Val Pro Lys Ser Gly Asp Thr Lys Tyr Asn Glu Lys Phe Lys
1               5                   10                  15
Ser

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Ser Gly Tyr
1

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ser Ser Lys Ser Leu Leu Gln Arg Asn Gly Ile Thr Tyr Leu Cys
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Met Ser Asn Leu Ala Ser
1               5

<210> SEQ ID NO 28
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Gln Asp Leu Glu Leu Pro Pro Thr
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Tyr Gly Met His
1               5

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Ile Asn Ser Arg Ser Asp Thr Ile Tyr Tyr Val Asp Thr Val Lys
1               5                   10                  15

Gly

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Tyr Tyr Gly Met Asp Tyr
1               5

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ser Ser Lys Ser Leu Leu His Thr Asn Gly Ile Thr Tyr Leu Tyr
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

```
Gln Met Ser Asn Leu Ala Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Gln Asn Leu Glu Leu Pro Pro Thr
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asn Tyr Glu Met His
1               5

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Ile Asn Ser Gly Ser Arg Thr Ile Tyr Tyr Ala Asp Thr Val Lys
1               5                   10                  15

Gly

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Tyr His Ala Met Asp Tyr
1               5

<210> SEQ ID NO 38
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
atgaagttgc ctgttaggct gttggtgctg atgttctgga ttcctgcttc caacagtgat      60
gttgtgatga cccaaactcc actctcccctg cctgtccgtc ttggagatca ggcctccatc     120
tcttgcagac ctagtcagag cattgtacat ggtaatagaa aaacctatttt agaatggtat     180
```

```
ctgcagaaac caggccagtc cccaaagctc ctgatctaca aagtttccaa ccgatttcct    240 gggtcccag acaggttcag tggcagtaga tcagggacag atttcacact caagatcagc    300
agagtggagg ctgcggatct gggagtttat tactgctttc aaggttcaca tgttccgtgg    360
acgttcggtg gaggcaccaa gctggaaatc aaa                                  393
```

<210> SEQ ID NO 39
<211> LENGTH: 423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
atggaatgga gctgggtctt tctcttcctc ctgtcagtaa ttgcaggtgt ccaatcccag     60
gttcatctgc agcagtctgg ggctgatctg gtgaggcctg ggcttcagt gacgctgtcc    120 tgcaaggctt cgggctacac atttactgac tttgaaatgc actgggtgaa gcagacacct    180
gtgcatggcc tggattggat tggagctatt gatcctgaaa ctggtagtac tggctacaat    240
cagaagttca aggacaaggc catactcact gcagacagat cctccagcac agcctacatg    300
gagctccgca gcctgacatc tgaggactct gccgtctatt actgtgcaag agcctactat    360
aataactaca gggactatgc tatggactac tggggtcaag aacctcagt cgccgtctcc    420 tca                                                                  423
```

<210> SEQ ID NO 40
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
atgagtcctg cccagttcct gattctgtta gtgctctgga ttcgggaaac caacggtgat     60
gttgtgatga cccagactcc actcactttg tcggttacca ttggacgacc agcctccatc    120
tcttgcaagt caagtcagag cctcttagaa agtgatgaa agacatattt gaattggttg    180
ttacagaggc caggccagtc tccaaagcgc ctaatctatc tggtgtctaa actggactct    240
ggagtccctg acaggttcac tggcagtgga tcagggacag atttcacact gaaaatcagc    300
agagtggagg ctgaggattt gggagtttat tattgctggc aaggtacaca ttttcctcgg    360
acgttcggtg gaggcaccaa gctggaaatc aaa                                  393
```

<210> SEQ ID NO 41
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
atgggatgga gctgtatcat gctcttcttg gcagcaacag ctacaggtgt ccactcccag     60
gtccaactgc agcagcctgg ggctgagctt gtgaagcctg ggcttcagt gaagctgtcc    120 tgcaaggctt ctggctacac cttcaccagc tactggatgc actgggtgaa gcagaggcct    180
ggacgaggcc ttgagtggat tggaaggatt gttcctaaga gtggtgatac taagtataat    240
```
gagaagttca agagcaaggc cacactgact gtagacaaac cctccagcac agcctacatg    300
cagctcagca gcctgacatc tgaggactct gcggtctatt attgtgctag agagagtggc    360
tactggggcc aaggcaccac tctcacagtc tcctcg                              396

<210> SEQ ID NO 42
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atgaggttct ctgctcagct tctggggctg cttgtgctct ggatccctgg atccactgca     60
gagattgtga tgacgcaggc tgcattctcc aaaccagtca ctcttggaac atcagcttcc    120
atttcctgca ggtccagtaa gagtctccta cagaggaatg catcacgta  tttgtgttgg    180 tttctgcaga ggccaggcca gtctcctcag ctcctgattt atcagatgtc caaccttgcc    240
tcaggagtcc cagacaggtt cagttgcagt gggtcaggaa ctgaattcac actgagaatc    300
agcagagtgg aggctgagga tgtgggtgtt tattactgtg ctcaagatct agagcttcct    360
ccgacgttcg gtggaggcac caagctggaa atcaga                              396

<210> SEQ ID NO 43
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atggactcca ggctcaattt agttttcctt gtccttattt taaaaggtgt ccagtgtgag     60
gtgcagttgg tggagtctgg gggaggctta gtgaagcctg gagggtccct gaaactctct    120
tgtgcagcct ctggattcac tttcagtgac tatggaatgc acttcgttcg tcaggctcca    180
gagaggggac tggagtgggt tgcatacatc aatagtcgca gcgataccat ctactatgta    240
gacacagtga agggccgatt caccatctcc agagacaatg ccaagaacac cctgttcctg    300
caaatgacca gtctgaggtc tgaggacacg gccatatatt actgtgcaag agagtattat    360
ggtatggact actggggtca aggaacctca gtcaccgtct cctca                    405

<210> SEQ ID NO 44
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atgaggttct ctgctcagct tctggggctg cttgtgctct ggatccctgg atccactgca     60
gatattgtga tgacgcaggc tgcattctcc aatccagtca ctcttggaac atcagcttcc    120
atctcctgca ggtctagtaa gagtctccta catactaatg catcaccta  tttgtattgg    180 tttctgcaga agccaggcca gtctcctcag ctcctgattt atcagatgtc caaccttgcc    240
tcaggagtcc ctgacaggtt cagtagcagt gggtcaggaa ctgatttcac actgagaatc    300
agcagagtgg aggctgagga tgtgggtgtt tattactgtg ctcaaaatct agaacttcct    360
ccgacgttcg gtggaggcac caagctggaa atcaaa 396

```
<210> SEQ ID NO 45
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
```
atggactcca ggctcaattt agttttcctt gtccttattt taaaaggtgt ccagtgtgag 60
gtgcagctgg tggagtctgg gggaggcctg gtgaagcctg gagggtccct gaaactctcc 120
tgtgtagtct ctggattcac tttcaataac tatgaaatgc actgggttcg cctggctcca 180
gagaagggac tggagtggat tgcatacatt aacagcggca gtaggaccat ctactatgca 240
gatacagtga agggccgatt caccatttcc agagacaatg ccaaaaacat cctattcctg 300
caaatgacca atctgaggtc tgaggacacg gccatgtatt attgtacaag atattaccat 360
gctatggact attggggtca aggaacctca gtcaccgtct cctca 405

```
<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
```
aaggtgaaag tgactgattc 20

```
<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
```
ctcgtatctt ttcccacggc 20

```
<210> SEQ ID NO 48
<211> LENGTH: 8
<212> TYPE: PRT
<213> ORGANISM: Gallus sp.

<400> SEQUENCE: 48
```

Ser Ile Ile Asn Phe Glu Lys Leu
1               5

```
<210> SEQ ID NO 49
<211> LENGTH: 10
<212> TYPE: DNA
<213> ORGANISM: Unknown
<220> FEATURE:
<223> OTHER INFORMATION: Description of Unknown:
      ISRE-1 sequence

<400> SEQUENCE: 49
```
gaaagagaaa 10

```
<210> SEQ ID NO 50
```

```
<211> LENGTH: 10
<212> TYPE: DNA
<213> ORGANISM: Unknown
<220> FEATURE:
<223> OTHER INFORMATION: Description of Unknown:
      ISRE-2 sequence

<400> SEQUENCE: 50
tttccttttc                                                              10
```

OSTEOPONTIN MONOCLONAL ANTIBODIES

CROSS REFERENCE TO RELATED APPLICATIONS

This application claims priority to and benefit of U.S. Provisional Patent Application No. 62/944,777 filed on Dec. 6, 2019, and is incorporated by reference in its entirety.

STATEMENT REGARDING FEDERALLY SPONSORED RESEARCH

This invention was made with government support under CA133085 and CA236436 awarded by the National Institutes of Health and BX001962 awarded by Veteran's Affairs. The government has certain rights in this invention.

TECHNICAL FIELD OF THE INVENTION

This invention is generally related to antibodies for modulating OPN signaling and methods of using the same.

BACKGROUND OF THE INVENTION $CD8^+$ cytotoxic T lymphocytes are the central component of the host adaptive immune system. A typical $CD8^+$ T cell immune response starts from T cell receptor (TCR) recognition of cognate antigenic peptides presented by the MHC class I molecule. The interaction between the TCR and the antigenic peptides presented by the MHC class I complex, in coordination with costimulatory signals delivered by interactions between costimulatory ligands B7.1 (CD80) and/or B7.2 (CD86) on antigen presenting cells (APCs), induces $CD8^+$ T cell activation (Ishijima, M., et al., *Exp Cell Res*, 312:3075-3083 (2006); Rittling, S. R., et al., *J Bone Miner Res*, 13:1101-1111 (1998); Rittling, S. R., et al, *Exp Nephrol*, 7:103-113 (1999)). However, T cell-mediated cytotoxicity must spare the destruction of normal cells and maintain self-tolerance, which is accomplished by several co-repressive mechanisms and also through receptor-ligand interactions between $CD8^+$ T cells and APCs. The major co-repressive receptor, programmed cell death protein 1 (PD-1), interacts with a programmed cell death protein 1 ligand (PD-L1) and/or PD-L2 expressed by APCs (Boussiotis, Virginia, *N Engl J Med*, 375(18):1767-1778 (2016); Keir, et al., *Annu Rev Immunol*, 26:677-704 (2008); Taylor, et al., *Immunity*, 44(2):274-286 (2016)), resulting in dephosphorylation of both CD28 and TCR and repression of T cell activation (Boussiotis, V A., *N Engl J Med*, 375(18):1767-1778 (2016); Hui, et al., *Science*, 355(6332):1428-1433 (2017); Kamphorst, et al., *Science*, 355(6332):1423-1427 (2017); Krueger, et al., *Immunity*, 46(4):529-531 (2017)). In addition, CTLA-4, LAG-3 and TIM-3 also act as co-repressive receptors to keep chronologically activated effector T cells in check (Wherry, E J., *Nat Immunol*, 12(6):492-499 (2011)). These co-repressive receptors thus function as immune checkpoints to maintain the balance during $CD8^+$ T cell adaptive immune response.

CTLs are the primary immune cells that act to eradicate tumors (Hanson, et al., *Immunity*, 13(2):265-276 (2000); Golstein and Griffiths, *Nat Rev Immunol*, 18(8):527-535 (2018)). On one hand, CTLs recognize tumor cells through tumor-specific antigens to mount an antitumor immune response and suppress tumor progression. However, tumor cells often mount a counterattack by multiple mechanisms including loss of antigen expression, and both primary and acquired resistance mechanisms, which in turn shut down the tumor-reactive CTLs in the tumor microenvironment (Ribas, A., *Cancer Discov*, 5(9):915-919 (2015); Marisa, et al., *J natl Cancer Inst*, 110(1):68-77 (2018); Juneja, et al., *J Exp Med*, 214(4):895-904 (2017); Kim et al., *Trends Immunol*, 39(8):624-631 (2018)). Therefore, tumor cells hijack the co-repressive receptor-based immune checkpoint mechanism to suppress tumor-reactive CTLs to avoid immune rejection (Hirano, F., et al., *Cancer Res*, 65(3): 1089-1096 (2005); Leach, D. R., et al., *Science*, 271(5256): 1734-1736 (1996); Lin, H., et al., *J Clin Invest*, 128(2):805-815 (2018); Tang, H., et al., *J Clin Invest*, 128(2):580-588 (2018)). Based on this mechanism, antibody-based inhibitors to block CTLA-4 and PD-1/PD-L1 immune checkpoints have been developed and shown durable efficacy in some types of human cancers (Brahmer, J. R., et al., *N Engl J Med*, 366(26):2455-2465 (2012); Ariyan, C. E., et al., *Cancer Immunol Res*, 6(2):189-200 (2018); Zou, W., et al., *Sci Transl Med*, 8(328):328rv4 (2016)).

Despite breakthroughs in immune checkpoint inhibitor immunotherapy, not all human cancers respond to immune checkpoint inhibitor immunotherapy and a large fraction of patients with the responsive types of cancers do not respond to current immune checkpoint inhibitor immunotherapy. The factors underlying this differential responsiveness to immune checkpoint inhibitor therapy between patients remains unknown. However, this is thought to be, in part, due to the existence of as-yet-undiscovered immune checkpoints which continue to suppress the immune response when currently known checkpoints are blockaded. Therefore, there is a need for more efficient immune checkpoint inhibitors or the discovery of new immune checkpoints that can be targeted for the treatment of cancer.

Thus, it is an object of the invention to provide compositions that modulate osteopontin (OPN) mediated signal transduction to enhance or promote activating immunological responses.

SUMMARY OF THE INVENTION

Antibodies and antigen binding fragments thereof that immunospecifically bind osteopontin (OPN) and inhibit OPN activity are provided herein. The disclosed antibodies and antigen binding fragments are useful for modulating signal transduction through OPN proteins. The antibodies and antigen-binding fragments herein are useful for the treatment or inhibition of cancer, osteoporosis, or other immune diseases.

One embodiment provides a monoclonal antibody or antigen-binding fragment thereof that binds specifically to OPN, wherein the antibody has the three heavy chain CDRs (HCDR1, HCDR2, and HCDR3) contained within any one of the heavy chain variable region (HCVR) sequences selected from the group consisting of SEQ ID NOs: 7, 9, 11, or 13, and the three light chain CDRs (LCDR1, LCDR2, and LCDR3) contained within any one of the light chain variable region (LCVR) sequences selected from the group consisting of SEQ ID NO: 6, 8, 10, or 12. In one embodiment, the antibody has (a) an HCDR1 domain having an amino acid sequence selected from the group consisting of SEQ ID NOs:17, 23, 29, and 35; (b) an HCDR2 domain having an amino acid sequence selected from the group consisting of SEQ ID NO:18, 24, 30, or 36; (c) an HCDR3 domain having an amino acid sequence selected from the group consisting of SEQ ID NO:19, 25, 31, or 37; (d) an LCDR1 domain having an amino acid sequence selected from the group consisting of SEQ ID NOs: 14, 20, 26, or 32; (e) an LCDR2 domain having an amino acid sequence selected from the group consisting of SEQ ID NOs:15, 21, 27, or 33; and (f) an LCDR3 domain having an amino acid sequence selected from the group consisting of SEQ ID NO:16, 22, 28, or 34.

Also provided is a monoclonal antibody or antigen-binding fragment thereof that binds specifically to OPN, wherein the antibody includes the heavy chain variable region (HCVR) sequences of SEQ ID NO:7, and the light chain variable region (LCVR) of SEQ ID NO:6. In such an embodiment, the HCVR includes HCDR1 according to SEQ ID NO:17, HCDR2 according to SEQ ID NO:18, HCDR3 according to SEQ ID NO:19; and the LCVR includes LCDR1 according to SEQ ID NO:14, LCDR2 according to SEQ ID NO:15, and LCDR3 according to SEQ ID NO:16.

Another embodiment provides a monoclonal antibody or antigen-binding fragment thereof that binds specifically to OPN, wherein the antibody includes the heavy chain variable region (HCVR) sequences of SEQ ID NO:9; and the light chain variable region (LCVR) of SEQ ID NO:8. In such an embodiment, the HCVR includes HCDR1 according to SEQ ID NO:23, HCDR2 according to SEQ ID NO:24, HCDR3 according to SEQ ID NO:25, and the LCVR includes LCDR1 according to SEQ ID NO:20, LCDR2 according to SEQ ID NO:21, and LCDR3 according to SEQ ID NO:22

Yet another embodiment provides monoclonal antibody or antigen-binding fragment thereof that binds specifically to OPN, wherein the antibody includes the heavy chain variable region (HCVR) sequences of SEQ ID NO:11, and the light chain variable region (LCVR) of SEQ ID NO:10. In such an embodiment, the HCVR includes HCDR1 according to SEQ ID NO:29, HCDR2 according to SEQ ID NO:30, HCDR3 according to SEQ ID NO:31, and the LCVR includes LCDR1 according to SEQ ID NO:26, LCDR2 according to SEQ ID NO:27, and LCDR3 according to SEQ ID NO:28.

Still another embodiment provides a monoclonal antibody or antigen-binding fragment thereof that binds specifically to OPN, wherein the antibody includes the heavy chain variable region (HCVR) sequences of SEQ ID NO:13, and the light chain variable region (LCVR) of SEQ ID NO:12. The HCVR includes HCDR1 according to SEQ ID NO:35, HCDR2 according to SEQ ID NO:36, HCDR3 according to SEQ ID NO:37, and the LCVR includes LCDR1 according to SEQ ID NO:32, LCDR2 according to SEQ ID NO:33, and LCDR3 according to SEQ ID NO:34.

Also provided are pharmaceutical compositions including any of the disclosed antibodies in combination with an excipient.

Methods of using the antibodies are also disclosed. One embodiment provides a method for reducing tumor burden in a subject in need thereof, by administering to the subject a pharmaceutical composition including one of the disclosed anti-OPN antibodies in an amount effective to reduce OPN signaling induced immune suppression. The tumor can be in any tissue including, but not limited to, bladder, brain, breast, cervical, colorectal, esophageal, hematological, hepatic, nasopharyngeal, pancreatic, prostate, skin, stomach, renal, testicular, bone, or uterine tissue.

One embodiment provides a method of inducing an immune response in a subject in need thereof by administering to the subject a pharmaceutical composition including one of the disclosed anti-OPN antibodies in an amount effective to reduce OPN induced inhibition of T cell activation in the subject.

Another embodiment provides a method for treating osteoporosis in a subject in need thereof by administering to the subject a pharmaceutical composition including one of the disclosed anti-OPN antibodies in an amount effective to reduce OPN signaling and thereby treat or inhibit osteoporosis.

Also disclosed are OPN fusion proteins. One embodiment provides an OPN fusion protein including the amino acid sequence of any one of SEQ ID NO:1-5 or a functional variant thereof linked to an immunoglobulin domain, wherein the fusion protein inhibits, reduces, or blocks OPN mediated signal transduction. Another embodiment provides a method for reducing tumor burden in a subject in need thereof by administering to the subject a pharmaceutical composition including the disclosed fusion proteins in an amount effective to reduce OPN signaling induced immune suppression.

BRIEF DESCRIPTION OF THE DRAWINGS

FIGS. 1A-1E: BALB/c mouse-derived mammary carcinoma 4T1 cells ($1\times10^4$ cells/mouse) were injected into the mammary gland of WT (C57BL6/J, n=4) and IRF8-KO (C57BL/6, n=3) mice. Mice were sacrificed at day 26 and dissected for examination of tumor presence. FIGS. 1A-1B are representative photographs of WT (FIG. 1A) and IRF8-KO (FIG. 1B) mice injected with BALB/c mouse-derived mammary carcinoma cells. The arrows represent the presence of a tumor. FIG. 1C is a bar graph showing the percentage of WT and IRF8-KO mice with tumors. FIGS. 1D and 1E are line graphs showing tumor volume over time in WT (FIG. 1D) and IRF8-KO (FIG. 1E) mice. FIGS. 1F-1K: WT (n=4) and IRF8-KO (n=4) mice were vaccinated with OVA peptide, followed by a boost with the same peptide regime 14 days later. Peripheral blood was collected 7 days after boost and stained with MHCII-, CD8-, and OVA tetramer-specific antibodies. MHCII-CD8+ cells were gated for OVA tetramer+ cells. Naive C57BL/6 mice were used as negative and gating controls. The tetramer+ CD8+ T cells were quantified (FIGS. 1I-1H). FIGS. 1L-1N: WT C57BL/6 and IRF8-KO BM cells were adoptively transferred into lethally irradiated C57BL/6 recipient mice to recreate chimera mice with IRF8 deficiency only in the hematopoietic cells. The chimera WT (n=4) and IRF8-KO (n=3) mice were vaccinated as above and analyzed for OVA-specific CD8+ T cells. Shown are representative plots from one pair of mice. FIG. 1N shows quantification of OVA-specific CD8+ T cells in WT and IRF8-KO chimera mice.

FIGS. 2C-2F are flow cytometry scatter plots showing the CD8+ cells gated out as in FIG. 2B further analyzed for $CD44^{hi}$ cells with CD62L as reference. Shown are representative plots of 1 pair of the mice.

FIG. 3A is a graph showing OPN (OPN) mRNA expression in RNA prepared from total spleens of WT (n=3) and IRF8-KO (n=3) mice and analyzed by qPCR. FIG. 3B is a flow cytometry scatter plot showing the gating schematic of spleen cells of WT (n=3) and IRF8-KO (n=3) mice stained with CD19-, CD3-, CD11b-, and Gr1-specific mAbs, followed by intracellular staining of OPN. The OPN+ cells were gated to show the $CD11b^+Gr1^+$ myeloid cells from IRF8-KO mice. FIG. 3C is a graph showing OPN protein level in the $CD11b^+Gr1^+$ myeloid cells from FIG. 3B. FIG. 3D is a graph showing the percentage of OPN+ cells in total spleen cells of WT (n=3) and IRF8-KO (n=3) mice. FIG. 3E is a plot showing the expression of Ly6C$^{hi}$Ly6G$^+$ and Ly6C$^{lo}$Ly6G$^-$ cells spleen cells from IRF8-GFP mice. FIG. 3F is a graph showing the quantification of the plots from FIG. 3E. FIG. 3G is a plot showing the expression of Ly6C$^{hi}$Ly6G$^+$ and Ly6C$^{lo}$Ly6G$^-$ cells were gated and analyzed for OPN expression level. FIG. 3H is a graph showing the quantification of the OPN$^+$ cells in Ly6C$^{hi}$Ly6G$^+$ and Ly6C$^{lo}$Ly6G$^-$ cells.

FIGS. 4A-4E are plots showing the number of WT mouse spleen cells expressing CFSE. CD3$^+$ T cells from WT mouse spleen were labeled with CFSE and cultured in plates coated with anti-CD3 (0.8 µg/ml) and anti-CD28 (10 µg/ml) mAbs and OPN at the indicated concentrations for 3 days. Cells were then stained with CD8-specific mAb and CD8$^+$ T cells were analyzed for CFSE intensity. The CFSE labeled and unstimulated cells were used as control. Representative data of cells from 1 of the 3 mice are shown. FIG. 4F is a graph showing the CFSE intensity from FIGS. 4A-4E quantified as division index. FIG. 4G is a graph showing IFN-γ protein levels in CD3$^+$ T cells cultured in plates coated with anti-CD3 (0.8 µg/ml) and anti-CD28 (10 µg/ml) mAbs and OPN at the indicated concentrations in triplicate for 3 days. Data from FIGS. 4F and 4G were analyzed using a 1-way ANOVA, with Dunnett's test for multiple comparisons. FIGS. 4H-4J are plots showing percent CD69$^+$ cells of CD8$^+$ cells (FIG. 4H), percent of CD25$^+$ cells of CD8$^+$ cells (FIG. 4I), and percent PD-1$^+$ cells of CD8$^+$ cells (FIG. 4J) in CD3$^+$ T cells cultured in plates coated with anti-CD3 (0.8 µg/ml) and anti-CD28 (10 µg/ml) mAbs in the presence of IgG (5 µg/ml) or OPN (1 µg/ml and 5 µg/ml, respectively). Cells were collected at the indicated time points, stained with CD69-, CD25-, PD-1-, and CD8-specific mAbs, and analyzed by flow cytometry. Data are mean±SD. Significance was calculated using a 2-way ANOVA with Tukey's test.

FIGS. 5A-5B are flow cytometry plots showing phenotypes of WT (CD45.1) and IRF8-KO (CD45.2) CD4$^+$ and CD8$^+$ T cells in the mixed BM chimeras. FIG. 5C is a graph showing quantification of the CD4$^+$ and CD8$^+$ cells from WT (CD45.1) and IRF8-KO (CD45.2) as shown in FIGS. 5A-5B. FIG. 5D shows the gating strategy to gate CD45.1$^+$ and CD45.2$^+$ CD8$^+$ cells from blood cells from WT and IRF8-KO mixed BM chimera mice stained with CD45.1-, CD45.2-, CD8, CD44-, and CD62L-specific mAbs. FIGS. 5E and 5F show CD44 and CD62L expression in WT and IRF8-KO CD8+ cells. Representative plots of 1 of 3 mice are shown. FIG. 5G is a plot showing the percentage of CD44$^{hi}$ cells of the WT CD8$^+$ and IRF8-KO CD8$^+$ T cells. FIG. 5H is a flow cytometry plot showing the gating strategy to gate CD45.1+ and CD45.2$^+$ CD8$^+$ cells from blood cells from IRF8-KO (CD45.2) mixed BM chimera mice vaccinated with OVA peptide, followed by a boost with OVA peptide 14 days later. FIGS. 5I-5J are flow cytometry plots showing OVA-specific WT and IRF8-KO CD8$^+$ T cells. FIG. 5K is a graph showing quantification of the WT and IRF8-KO CD8$^+$ OVA-specific T cells.

FIG. 6A is a graph showing percent CD44 of CD8$^+$ cells in blood cells collected from WT (Lck-cre+/−Irf8+/+, n=7) and IRF8-TKO (n=4) mice. FIGS. 6B and 6C are graphs showing percent OPN (OPN) positive cells of CD11b$^+$Gr1$^+$ spleen cells collected from WT (Lck-cre+/−Irf8+/+, n=7) and IRF8-TKO (n=4) stained with CD11b$^-$ and Gr1$^-$ specific mAbs, followed by intracellular staining with OPN-specific mAb. The CD11b$^+$Gr1$^+$ cells were gated and analyzed for percentage of OPN$^+$ cells (FIG. 6B) and OPN MFI (FIG. 6C). FIGS. 6D-6E are flow cytometry plots showing OVA-specific CD8$^+$ T cells in WT (FIG. 6D) and IRF8-TKO (FIG. 6E) mice vaccinated with OVA peptide, followed by a boost with OVA peptide 14 days later. FIG. 6F is a graph showing quantification of WT and IRF8-KO CD8$^+$ OVA-specific T cells as shown in FIGS. 6D-6E. FIGS. 6G-6H are representative images of 4T1 tumor-bearing BALB/c and 4T1 tumor-challenged IRF8-TKO mice. The red arrow indicates location of the 4T1 tumor or lack of tumor in injected area. FIG. 6I is a bar graphs showing the percentage of mice with tumors.

FIG. 7I is a representative autoradiograph of EMSA analysis of CD3+ T cells stimulated on anti-CD3- and anti-CD28-coated plates for 3 days. Nuclear extracts were prepared and analyzed for IRF8 binding by using EMSA with the Pdcd1 promoter ISRE consensus sequence DNA probe. Anti-IRF8 antibody was used to identify the IRF8-DNA complexes. IgG was used as a negative control. Arrows point to the IRF8-Pdcd1 ISRE DNA complexes. FIGS. 7J-7K are representative autoradiographs of EMSA analysis of normal mouse colon tissues incubated with the 2 ISRE DNA probes. The unlabeled Pdcd1 ISRE DNA probe (cold probe) was used at the indicated amount (fold over the labeled Spp1 ISRE probes) to compete the Spp1 IRRE probes. Arrow points IRF8-DNA complex.

FIGS. 8A and 8B are graphs showing IRF8 (FIG. 8A) and OPN (FIG. 8B) mRNA expression data sets in normal colon and colon carcinoma tissues extracted from TCGA database and compared as indicated. FIG. 8C is a graph showing OPN protein levels in serum collected from healthy donors and patients with colon cancer. Each dot represents serum OPN protein level from 1 donor or patient.

FIG. 11C is a graph showing the mean fluorescence intensity of CD25-APC cells in samples with CT26.ck cells or CT26.OPNKO cells. FIG. 11D is a graph showing fluorescence intensity of CD25-APC cells in samples with CT26.ck cells or CT26.OPNKO cells. FIG. 11E is a photograph showing lung metastases in mice injected with CT26CK or CT26.OPNKO cells.

FIG. 13A is a schematic illustration showing the ELISA hybridoma validation scheme. FIG. 13B is a graph showing hybridoma ELISA screening results.

FIG. 14A is a graph showing the percent of divided CD25$^{lo}$ cells per total cells in cells treated with the indicated anti-OPN mAbs. FIGS. 14B-14C are flow cytometry plots showing CD25 and CFSE staining in cells treated with DMEM or mAb 100G2-2. FIGS. 141-14J are flow cytometry histograms showing CFSE staining in cells treated with DMEM or mAb 100G2-2.

DETAILED DESCRIPTION OF THE INVENTION

I. Definitions

Figure 2A:
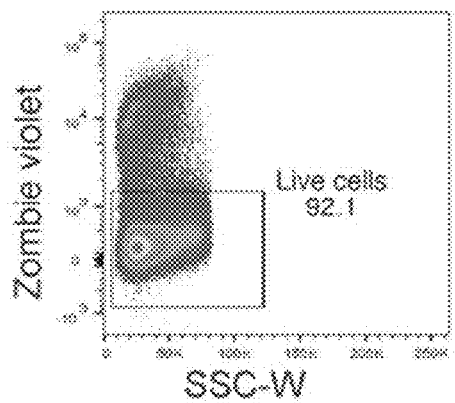
FIGS. 2A-2B are flow cytometry plots of peripheral blood cells stained with Zombie violet to exclude dead cells and the live cells were analyzed for CD4+ and CD8+ T cells. LN and spleen cells were collected from WT (n=3) and IRF8-KO (n=3) mice.
Figure 2B:
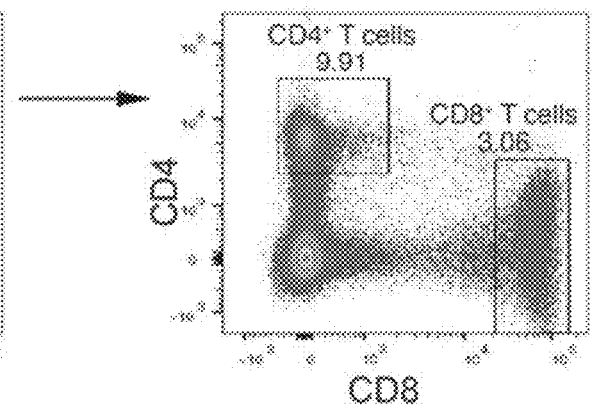
Figure 2E:
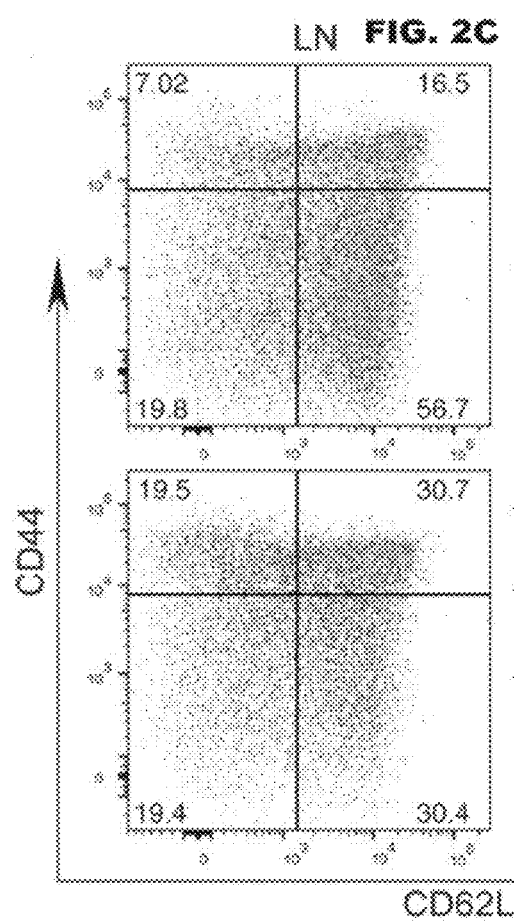
Figure 2F:
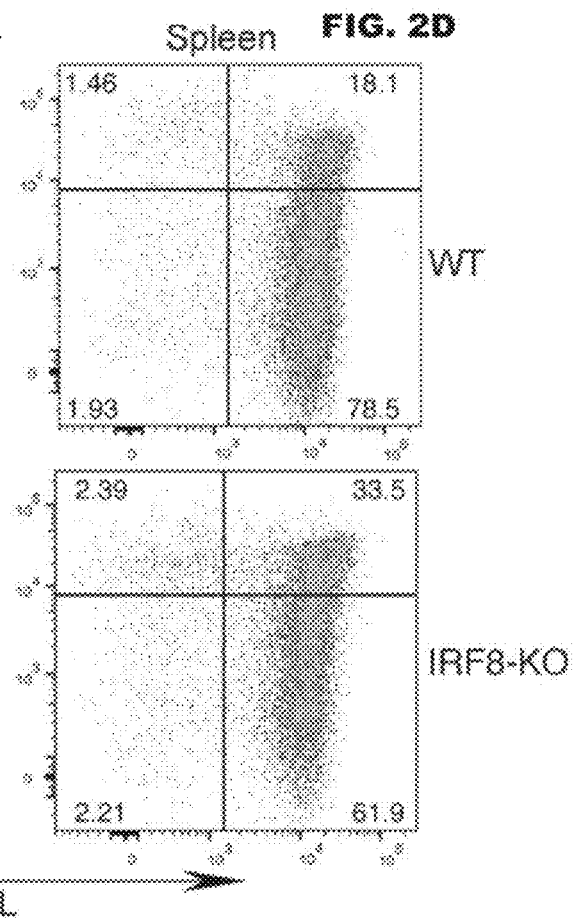

As used herein, a molecule is said to be able to "immunospecifically bind" a second molecule if such binding exhibits the specificity and affinity of an antibody to its cognate antigen. Antibodies are said to be capable of immunospecifically binding to a target region or conformation ("epitope") of an antigen if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. In some embodiments, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

As used herein, a molecule is said to "physiospecifically bind" a second molecule if such binding exhibits the specificity and affinity of a receptor to its cognate binding ligand. A molecule can be capable of physiospecifically binding to more than one other molecule.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Maryland (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', F(ab')$_2$, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.).

As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

As used herein the term "modulate" relates to a capacity to alter an effect, result, or activity (e.g., signal transduction). Such modulation can be agonistic or antagonistic. Antagonistic modulation can be partial (i.e., attenuating, but not abolishing) or it can completely abolish such activity (e.g., neutralizing). Modulation can include internalization of a receptor following binding of an antibody or a reduction in expression of a receptor on the target cell. Agonistic modulation can enhance or otherwise increase or enhance an activity (e.g., signal transduction). In a still further embodiment, such modulation can alter the nature of the interaction between a ligand and its cognate receptor so as to alter the nature of the elicited signal transduction. For example, the molecules can, by binding to the ligand or receptor, alter the ability of such molecules to bind to other ligands or receptors and thereby alter their overall activity. In some embodiments, such modulation will provide at least a 10% change in a measurable immune system activity, at least a 50% change in such activity, or at least a 2-fold, 5-fold, 10-fold, or at least a 100-fold change in such activity.

The term "substantially," as used in the context of binding or exhibited effect, is intended to denote that the observed effect is physiologically or therapeutically relevant. Thus, for example, a molecule is able to substantially block an activity of a ligand or receptor if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, the "activating" or "stimulatory" signals encompass signals that result in enhancing an activity or enhancing signal transduction.

As used herein, "suppressive" signals refer to signals that suppress immune activity.

The term "endogenous concentration" refers to the level at which a molecule is natively expressed (i.e., in the absence of expression vectors or recombinant promoters) by a cell (which cell can be a normal cell, a cancer cell or an infected cell).

As used herein, the terms "treat," "treating," "treatment" and "therapeutic use" refer to the elimination, reduction or amelioration of one or more symptoms of a disease or disorder. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the term "cancer" refers to a neoplasm or tumor resulting from abnormal uncontrolled growth of cells. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or web-like matrices in a three-dimensional basement membrane or extracellular matrix preparation. Non-cancer cells do not form colonies in soft agar and form distinct sphere-like structures in three-dimensional basement membrane or extracellular matrix preparations.

As used herein, an "immune cell" refers to any cell from the hemopoietic origin including, but not limited to, T cells, B cells, monocytes, dendritic cells, and macrophages.

As used herein, "inflammatory molecules" refer to molecules that result in inflammatory responses including, but not limited to, cytokines and metalloproteases such as including, but not limited to, IL-1β, TNF-α, TGF-beta, IFN-γ, IL-18, IL-17, IL-6, IL-23, IL-22, IL-21, and MMPs.

As used herein, the terms "immunologic," "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MEW molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays (CD4$^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

As used herein, the terms "individual," "host," "subject," and "patient" are used interchangeably herein, and refer to a mammal, including, but not limited to, humans, rodents, such as mice and rats, and other laboratory animals.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

II. Compositions for Modulating Osteopontin Signaling

Antibodies and antigen binding fragment thereof that immunospecifically bind osteopontin (OPN) and inhibit OPN activity are provided herein. The disclosed antibodies and antigen binding fragments are useful for modulating signal transduction through OPN proteins. It was discovered that interferon regulatory factor 8 (IRF8) functions as a repressor of OPN expression and loss of IRF8 expression in tumor cells leads to elevated expression of OPN which acts as a potent T cell suppressor. Therefore, reducing or blocking OPN signaling in tumor cells or the tumor microenvironment with OPN binding moieties is useful for treating cancer.

A. Osteopontin

OPN is a secreted phosphorylated glycoprotein that mediates diverse biological functions. OPN is also known as secreted phosphoprotein 1 (SPP1) 44 kDa bone phosphoprotein, sialoprotein 1, 2ar, uroprotein, and early T-lymphocyte activation-1 (Eta-1). OPN was originally discovered as a bone sialoprotein involved in osteoclast attachment to mineralized bone. However, it is now known to play roles in various other physiological and pathological systems. OPN is involved in normal physiological processes and is implicated in the pathogenesis of a variety of disease states, including atherosclerosis, glomerulonephritis, cancer, and several chronic inflammatory diseases. OPN is expressed in various cell types and tissues including but not limited to pre-osteoblasts, osteoblasts, osteocytes, chondrocytes, fibroblasts, dendritic cells, macrophages, T-cells, hepatocytes, smooth muscle cells, skeletal muscle cells, endothelial cells, brain, placenta, mammary glands, and kidney.

Extracellular OPN functions through interactions with cell surface receptors. Exemplary receptors that OPN interacts with include but are not limited to integrins such as αvβ1, αvβ3, αvβ5, α4β1, α5β1, α8β1, and α9β1, and the hyaluronic acid receptor CD44. Through its interactions with integrins, OPN mediates cell migration, adhesion, and survival in many cell types. OPN also functions as a Th1 cytokine, promotes cell-mediated immune responses, and plays a role in chronic inflammatory and autoimmune diseases. Besides its function in inflammation, OPN is also a regulator of biomineralization and a potent inhibitor of vascular calcification.

OPN is a member of the SIBLING (small integrin-binding ligand, N-linked glycoprotein) family of proteins. It is synthesized as an approximately 32 kDa protein, but due to post-translational modifications its apparent molecular mass ranges from 45 to 75 kDa.

Sequences for OPN are known in the art. For example, the amino acid sequence for human OPN isoform A is as follows:

```
        10         20         30
MRIAVICFCL LGITCAIPVK QADSGSSBEK 40         50         60
QLYNKYPDAV ATWLNPDPSQ KQNLLAPQNA 70         80         90
VSSEETNDFK QETLPSKSNE SHDHMDDMDD 100        110        120
EDDDDHVDSQ DSIDSNDSDD VDDTDDSHQS 130        140        150
DESHHSDESD ELVTDFPTDL PATEVFTPVV 160        170        180
PTVDTYDGRG DSVVYGLRSK SKKFRRPDIQ 190        200        210
YPDATDEDIT SHMESEELNG AYKAIPVAQD 220        230        240
LNAPSDWDSR GKDSYETSQL DDQSAETHSH 250        260        270
KQSRLYKRKA NDESNBHSDV IDSQELSKVS 280        290        300
REFHSHEFHS HEDMLVVDPK SKEEDKHLKF

310
RISHELDSAS SEVN (SEQ ID NO: 1) known as UniProtKE5-P10451
(OSTP HUMAN) which is incorporated
by reference in its entirety.
```

Amino acids 1-16 of SEQ ID NO:1 represent the signal peptide.

Human OPN isoform B (OPN-b, OP1A) is missing amino acids 58-71 of SEQ ID NO:1 and has the following amino acid sequence:

```
        10         20         30         40
MRIAVICFCL LGITCAIPVK QADSGSSEEK QLYNKYPDAV 50         60         70         80
ATWLNPDPSQ KQNLLAPETL PSKSNESHDH MDDMDDEDDD 90        100        110        120
DHVDSQDSID SNDSDDVDDT DDSHQSDESH HSDESDELVT 130        140        150        160
DFPTDLPATE VFTPVVPTVD TYDGRGDSVV YGLRSKSKKF 170        180        190        200
RRPDIQYPDA TDEDITSHME SEELNGAYEA IPVAQDLNAP 210        220        230        240
SDWDSRGKDS YBTSQLDDQS AETHSHKQSR LYKRKAMDES 250        260        270        280
NEHSDVIDSQ ELSKVSRSFH SHBFHSKEDM LVVDPKSKEE 290        300
DKHLKFRISH ELDSASSEVN (SEQ ID NO: 2) known UniProtKB-P10451-2,
which is incorporated by reference
in its entirety.
```

Human OPN isoform C (OPN-c) is missing amino acids 31-57 of SEQ ID NO:1 and has the following amino acid sequence:

```
            10         20         30         40
   MRIAVICFCL LGITCAIPVE QADSGSSEEK QRAVSSEETN
            50         60         70         80
   DFKQETLPSK SNESHDHMDD MDDEDDDDHV DSQDSIDSND
            90        100        110        120
   SDDVDDTDDS HQSDESHHSD ESDELVIDEP TDLPATEVFT
           130        140        150        160
   PVVPTVDTYD GRGDSVVYGL RSKSKKFRRP DIQYPDATDE
           170        180        190        200
   DITSHMESEE LNGAYKAIPV AQDLNAPSDW DSRGKDSYET
           210        220        230        240
   SQLDDQSAET HSHKQSRLYK RKANDESNEH SDVIDSQELS
           250        260        270        280
   KVSREFHSHE FHSEDMLVV DPKSKEEDKH LKFRISHELD

SASSEVN (SEQ ID NO: 3) know as UniProtKB
   accession-P10451-3 which is incorporated
   by reference in its entirety).
```

Human OPN isoform D is missing amino acids 95-116 of SEQ ID NO:1 and has the following amino acid sequence:

```
            10         20         30         40
   MRIAVICFCL LGITCAIPVK QADSGSSEEK QLYNKYPDAV
            50         60         70         80
   ATWLNPDPSQ KQNLLAPQNA VSSEETNDFK QETLPSKSNE
            90        100        110        120
   SHDHMDDMDD EDDDSHQSDE SHHSDESDEL VTDFPTDLPA
           130        140        150        160
   TEVFTPVVPT VDTYDGRGDS VVYGLRSKSK KFRRPDIQYP
           170        180        190        200
   DATDEDITSH MESEELNGAY KAIPVAQDLN APSDWDSRGK
           210        220        230        240
   DSYSTSQLDD QSAETHSHKQ SRLYKRKAND ESNEHSDVID
           250        260        270        280
   SQELSKVSRE FHSKEFHSHE DMLVVDPKSK EEDKHLKFRI
           290
   SHELDSASSE VN (SEQ ID NO: 4) known as UniProtKB
   accession P10451-4 which is incorporated
   by reference in its entirety.
```

Human OPN isoform 5 is missing amino acids 59-72 of SEQ ID NO:1 and has the following amino acid sequence:

```
            10         20         30         40
   MRIAVICFCL LGITCAIPVK QADSGSSEEK QLYNKYPDAV
            50         60         70         80
   ATWLNPDPSQ KQNLLAPQTL PSKSNESHDH MDDMDDEDDD
            90        100        110        120
   DHVDSQDSID SNDSDDVDDT DDSHQSDESH HSDESDELVT
           130        140        150        160
   DFPTDLPATE VFTPVVPTVD TYDGRGDSVV YGLREKSKEF
           170        180        190        200
   RRPDIQYPDA TDEDITSHME SEELNGAYKA IPVAQDLNAP
           210        220        230        240
   SDWDSRGKDS YETSQLDDQS AETHSHKQSR LYKRNANDES
           250        260        270        280
   NEHSDVIDSQ ELSKVSREFH SHEFHSHEDM LVVDPKSKEE
           290        300
   DKHLKFRISH ELDSASSEVN (SEQ ID NO: 5) known as UniProtKE accession
   910451-5 which is incorporated
   by reference in its entirety.
```

The disclosed antibodies may be specific for any isoform of OPN.

B. Osteopontin Binding Molecules

OPN-binding molecules, such as antibodies and antigen binding fragments thereof, fusion proteins, and other polypeptides that bind to OPN are provided. The sequences of the heavy and light chain variable regions, and CDRs thereof, from mouse anti-OPN antibodies are provided below. Antibodies, antigen binding fragments and other polypeptides including one or more of the sequences below, and variants thereof are provided. For example, antibodies, antigen binding fragments, and polypeptides including one, two, or three CDRs of an anti-OPN antibody light chain variable region and/or one, two, or three CDRs of an anti-OPN antibody heavy chain variable region that bind to OPN are provided. In some embodiments, the antibodies, antigen binding fragments, and polypeptides include the light chain variable region of an anti-OPN antibody, the heavy chain variable region of an anti-OPN, or a combination thereof, and can bind to OPN.

1. Antibody Sequences

As described in the Examples below, mice were immunized with recombinant OPN to generate a panel of antibodies. The sequences of light and heavy chain variable regions for monoclonal antibodies produced by four hybridomas, referred to herein as 100G2-2, 100D3-2, 103D6-1, and 89G9-1, are provided below. The signal sequence is underlined and CDRs are bolded in the context of the light and heavy chain sequences.

a. Clone 100G2-2
i. Light Chain
100G2-2 light chain variable region amino acid sequence is:

(SEQ ID NO: 6)

MKLPVRLLVLMFWIPASNSDVVMTQTPLSLPVRLGDQASISCRPSQSIVHGNRKTYLE

WYLQKPGQSPKWYKVSNRFSGVPDRFSGSRSGTDFTLKISRVEAADLGVYYCFQGSH

VPWTFGGGTKLEIK with

-continued

Light chain 100G2-2 CDR1:
(SEQ ID NO: 14)
RPSQSIVHGNRKTYLE

Light chain 100G2-2 CDR2:
(SEQ ID NO: 15)
KVSNRFS

Light chain 100G2-2 CDR3:
(SEQ ID NO: 16)
FQGSHVPWT

A nucleic acid sequence encoding the 100G2-2 light chain variable region is
(SEQ ID NO: 38)
ATGAAGTTGCCTGTTAGGCTGTTGGTGCTGATGTTCTGGATTCCTGCTTCCAACAGTG

ATGTTGTGATGACCCAAACTCCACTCTCCCTGCCTGTCCGTCTTGGAGATCAGGCCT

CCATCTCTTGCAGACCTAGTCAGAGCATTGTACATGGTAATAGAAAAACCTATTTAG

AATGGTATCTGCAGAAACCAGGCCAGTCCCCAAAGCTCCTGATCTACAAAGTTTCCA

ACCGATTTTCTGGGGTCCCAGACAGGTTCAGTGGCAGTAGATCAGGGACAGATTTCA

CACTCAAGATCAGCAGAGTGGAGGCTGCGGATCTGGGAGTTTATTACTGCTTTCAAG

GTTCACATGTTCCGTGGACGTTCGGTGGAGGCACCAAGCTGGAAATCAAA ii. Heavy Chain
100G2-2 heavy chain variable region amino acid seqinece is:
(SEQ ID NO: 7)
<u>MEWSWVFLFLLSVIAGVQS</u>QVHLQQSGADLVRPGASVTLSCKASGYTFTDFEMHWVK

QTPVHGLDWIGAIDPETGSTGYNQKFKDKAILTADRSSSTAYMELRSLTSEDSAVYY

CARAYYNNYRDYAMDYWGQGTSVAVSS
with

100G2-2 Heavy chain CDR1:
(SEQ ID NO: 17)
DFEMEI

100G2-2 Heavy chain CDR2:
(SEQ ID NO: 18)
AIDPETGSTGYNQKFKD

100G2-2 Heavy chain CDR3:
(SEQ ID NO: 19)
AYYNNYRDYAMDY

A nucleic acid sequence encoding the 100G2-2 heavy chain variable region is
(SEQ ID NO: 39)
ATGGAATGGAGCTGGGTCTTTCTCTTCCTCCTGTCAGTAATTGCAGGTGTCCAATCCC

AGGTTCATCTGCAGCAGTCTGGGGCTGATCTGGTGAGGCCTGGGGCTTCAGTGACGC

TGTCCTGCAAGGCTTCGGGCTACACATTTACTGACTTTGAAATGCACTGGGTGAAGC

AGACACCTGTGCATGGCCTGGATTGGATTGGAGCTATTGATCCTGAAACTGGTAGTA

CTGGCTACAATCAGAAGTTCAAGGACAAGGCCATACTCACTGCAGACAGATCCTCC

AGCACAGCCTACATGGAGCTCCGCAGCCTGACATCTGAGGACTCTGCCGTCTATTAC

TGTGCAAGAGCCTACTATAATAACTACAGGGACTATGCTATGGACTACTGGGGTCAA

GGAACCTCAGTCGCCGTCTCCTCA b. Clone 100D3-2
i. Light chain
100D3-2 light chain variable region amino acid sequence is:
(SEQ ID NO: 8)
<u>MSPAQFLILLVLWIRETNG</u>DVVMTQTPLTLSVTIGRPASISCKSSQSLLESDGKTYLNWL

LQRPGQSPKRLIYLVSKLDSGVPDRFTGSGSGTDFTLKISRVEAEDLGVYYCWQGTHFP

RTFGGGTKLEIK
with

100D3-2 light chain CDR1:
(SEQ ID NO: 20)
KSSQSLLESDGKTYLN

100D3-2 light chain CDR2:
(SEQ ID NO: 21)
LVSKLDS

100D3-2 light chain CDR3:
(SEQ ID NO: 22)
WQGTHFPRT

A nucleic acid sequence encoding the 100D3-2 light chain variable region is
(SEQ ID NO: 40)
ATGAGTCCTGCCCAGTTCCTGATTCTGTTAGTGCTCTGGATTCGGGAAACCAACGGT

GATGTTGTGATGACCCAGACTCCACTCACTTTGTCGGTTACCATTGGACGACCAGCC

TCCATCTCTTGCAAGTCAAGTCAGAGCCTCTTAGAAAGTGATGGAAAGACATATTTG

AATTGGTTGTTACAGAGGCCAGGCCAGTCTCCAAAGCGCCTAATCTATCTGGTGTCT

AAACTGGACTCTGGAGTCCCTGACAGGTTCACTGGCAGTGGATCAGGGACAGATTTC

ACACTGAAAATCAGCAGAGTGGAGGCTGAGGATTTGGGAGTTTATTATTGCTGGCA

AGGTACACATTTTCCTCGGACGTTCGGTGGAGGCACCAAGCTGGAAATCAAA ii. Heavy Chain
100D3-2 heavy chain variable region amino acid sequence is:
(SEQ ID NO: 9)
MGWSCIMLFLAATATGVHSQVQLQQPGAELVKPGASVKLSCKASGYTFTSYWMHWV

KQRPGRGLEWIGRIVPKSGDTKYNEKFKSKATLTVDKPSSTAYMQLSSLTSEDSAV

YYCARESGYWGQGTTLTVSS
with

100D3-2 Heavy chain CDR1:
(SEQ ID NO: 23)
SYWMH

100D3-2 Heavy chain CDR2:
(SEQ ID NO: 24)
RIVPKSGDTKYNEKFKS

100D3-2 Heavy chain CDR3:
(SEQ ID NO: 25)
ESGY

A nucleic acid sequence encoding the 100D3-2 heavy chain variable region is
(SEQ ID NO: 41)
ATGGGATGGAGCTGTATCATGCTCTTCTTGGCAGCAACAGCTACAGGTGTCCACTCC

CAGGTCCAACTGCAGCAGCCTGGGGCTGAGCTTGTGAAGCCTGGGGCTTCAGTGAA

GCTGTCCTGCAAGGCTTCTGGCTACACCTTCACCAGCTACTGGATGCACTGGGTGAA

GCAGAGGCCTGGACGAGGCCTTGAGTGGATTGGAAGGATTGTTCCTAAGAGTGGTG

ATACTAAGTATAATGAGAAGTTCAAGAGCAAGGCCACACTGACTGTAGACAAACCC

TCCAGCACAGCCTACATGCAGCTCAGCAGCCTGACATCTGAGGACTCTGCGGTCTAT

TATTGTGCTAGAGAGAGTGGCTACTGGGGCCAAGGCACCACTCTCACAGTCTCCTCG c. Clone 103D6-1
ii. Light chain
103D6-1 light chain variable region amino acid sequence is:
(SEQ ID NO: 10)
MRFSAQLLGLLVLWIPGSTAEIVMTQAAFSKPVTLGTSASISCRSSKSLLQRNGITYLC

WFLQRPGQSPQLLIYQMSNLASGVPDRFSCSGSGTEFTLRISRVEAEDVGVYYCAQDLE

LPPTFGGGTKLEIR
with

103D6-1 light chain CDR1:
(SEQ ID NO: 26)
RSSKSLLQRNGITYLC

103D6-1 light chain CDR2:
(SEQ ID NO: 27)
QMSNLAS

103D6-1 light chain CDR3:
(SEQ ID NO: 28)
AQDLELPPT

A nucleic acid sequence encoding the 103D6-1 light chain variable region is
(SEQ ID NO: 42)
ATGAGGTTCTCTGCTCAGCTTCTGGGGCTGCTTGTGCTCTGGATCCCTGGATCCACTG

CAGAGATTGTGATGACGCAGGCTGCATTCTCCAAACCAGTCACTCTTGGAACATCAG

CTTCCATTTCCTGCAGGTCCAGTAAGAGTCTCCTACAGAGGAATGGCATCACGTATT

TGTGTTGGTTTCTGCAGAGGCCAGGCCAGTCTCCTCAGCTCCTGATTTATCAGATGTC

CAACCTTGCCTCAGGAGTCCCAGACAGGTTCAGTTGCAGTGGGTCAGGAACTGAATT

CACACTGAGAATCAGCAGAGTGGAGGCTGAGGATGTGGGTGTTTATTACTGTGCTCA

AGATCTAGAGCTTCCTCCGACGTTCGGTGGAGGCACCAAGCTGGAAATCAGA ii. Heavy Chain
103D6-1 heavy chain variable region amino acid sequence is:
(SEQ ID NO: 11)
MDSRLNLVFLVLILKGVQCEVQLVESGGGLVKPGGSLKLSCAASGFTFSDYGMHFVRQ

APERGLEWVAYINSRSDTIYYVDTVKGRFTISRDNAKNTLFLQMTSLRSEDTAIYYCAR

EYYGMDYWGQGTSVTVSS
with

103D6-1 Heavy chain CDR1:
(SEQ ID NO: 29)
DYGMEI

103D6-1 Heavy chain CDR2:
(SEQ ID NO: 30)
YINSRSDTIYYVDTVKG

103D6-1 Heavy chain CDR3:
(SEQ ID NO: 31)
EYYGMDY

A nucleic acid sequence encoding the 103D6-1 heavy chain variable region is
(SEQ ID NO: 43)
ATGGACTCCAGGCTCAATTTAGTTTTCCTTGTCCTTATTTTAAAAGGTGTCCAGTGTG

AGGTGCAGTTGGTGGAGTCTGGGGGAGGCTTAGTGAAGCCTGGAGGGTCCCTGAAA

CTCTCTTGTGCAGCCTCTGGATTCACTTTCAGTGACTATGGAATGCACTTCGTTCGTC

AGGCTCCAGAGAGGGGACTGGAGTGGGTTGCATACATCAATAGTCGCAGCGATACC

ATCTACTATGTAGACACAGTGAAGGGCCGATTCACCATCTCCAGAGACAATGCCAA

GAACACCCTGTTCCTGCAAATGACCAGTCTGAGGTCTGAGGACACGGCCATATATTA

CTGTGCAAGAGAGTATTATGGTATGGACTACTGGGGTCAAGGAACCTCAGTCACCGT

CTCCTCA d. Clone 89G9-1
i. Light chain
89G9-1 light chain variable region amino acid sequence is:
(SEQ ID NO: 12)
MRFSAQLLGLLVLWIPGSTADIVMTQAAFSNPVTLGTSASISCRSSKSLLHTNGITYLY

WFLQKPGQSPQLLIYQMSNLASGVPDRFSSSGSGTDFTLRISRVEAEDVGVYYCAQNLE

LPPTFGGGTKLEIK
with

89G9-1 light chain CDR1:
(SEQ ID NO: 32)
RSSKSLLHTNGITYLY

89G9-1 light chain CDR2:
(SEQ ID NO: 33)
QMSNLAS

89G9-1 light chain CDR3:
(SEQ ID NO: 34)
AQNLELPPT

A nucleic acid sequence encoding the 89G9-1 light chain variable region is
(SEQ ID NO: 44)
ATGAGGTTCTCTGCTCAGCTTCTGGGGCTGCTTGTGCTCTGGATCCCTGGATCCACTG

CAGATATTGTGATGACGCAGGCTGCATTCTCCAATCCAGTCACTCTTGGAACATCAG

CTTCCATCTCCTGCAGGTCTAGTAAGAGTCTCCTACATACTAATGGCATCACCTATTT

GTATTGGTTTCTGCAGAAGCCAGGCCAGTCTCCTCAGCTCCTGATTTATCAGATGTCC

AACCTTGCCTCAGGAGTCCCTGACAGGTTCAGTAGCAGTGGGTCAGGAACTGATTTC

ACACTGAGAATCAGCAGAGTGGAGGCTGAGGATGTGGGTGTTTATTACTGTGCTCA

AAATCTAGAACTTCCTCCGACGTTCGGTGGAGGCACCAAGCTGGAAATCAAA ii. Heavy Chain
89G9-1 heavy chain variable region amino acid sequence is:
(SEQ ID NO: 13)
<u>MDSRLNLVFLVLILKGVQC</u>EVQLVESGGGLVKPGGSLKLSCVVSGFTFNNYEMHWVRL

APEKGLEWIAYINSGSRTIYYADTVKGRFTISRDNAKNILFLQMTNLRSEDTAMYYCTR

YYHAMDYWGQGTSVTVSS
with

89G9-1 Heavy chain CDR1:
(SEQ ID NO: 35)
NYEMH

89G9-1 Heavy chain CDR2:
(SEQ ID NO: 36)
YINSGSRTIYYADTVKG

89G9-1 Heavy chain CDR3:
(SEQ ID NO: 37)
YYHAMDY

A nucleic acid sequence encoding the 89G9-1 heavy chain variable region is
(SEQ ID NO: 45)
ATGGACTCCAGGCTCAATTTAGTTTTCCTTGTCCTTATTTTAAAAGGTGTCCAGTGTG

AGGTGCAGCTGGTGGAGTCTGGGGGAGGCCTGGTGAAGCCTGGAGGGTCCCTGAAA

CTCTCCTGTGTAGTCTCTGGATTCACTTTCAATAACTATGAAATGCACTGGGTTCGCC

TGGCTCCAGAGAAGGGACTGGAGTGGATTGCATACATTAACAGCGGCAGTAGGACC

ATCTACTATGCAGATACAGTGAAGGGCCGATTCACCATTTCCAGAGACAATGCCAA

AAACATCCTATTCCTGCAAATGACCAATCTGAGGTCTGAGGACACGGCCATGTATTA

TTGTACAAGATATTACCATGCTATGGACTATTGGGGTCAAGGAACCTCAGTCACCGT

CTCCTCA

2. Anti-OPN Antibodies and Antigen Binding Fragments Thereof

OPN binding molecules, including antibodies and antigen binding fragments thereof, that bind to one or more OPN polypeptides or fusion proteins, or fragments or variants thereof are disclosed. The antibodies disclosed herein are typically monoclonal antibodies, or antigen binding fragments thereof, that bind to an epitope present on an OPN polypeptide, or fragment or fusion thereof. In some embodiments the antibody binds to a conformational epitope. In some embodiments the antibody binds to a linear epitope. A linear epitope can be 4, 5, 6, 7, 8, 9, 10, 11, or more continuous amino acids in length. The epitope can include one or more non-amino acid elements, post-translation modifications, or a combination thereof. Examples of post-translational modifications include, but are not limited to glycosylation, phosphorylation, acetylation, citrullination and ubiquitination. For example, antibodies can bind an epitope that is formed at least in-part by one or more sugar groups.

The antibody or antigen binding fragment thereof can bind to an epitope that is present on an endogenous OPN polypeptide, or a recombinant OPN polypeptide, or a combination thereof. In some embodiments, the antibody or antigen binding fragment thereof binds to the extracellular domain, or a fragment thereof, or an epitope formed therefrom of OPN. In some embodiments, the antibody or antigen binding fragment thereof is a function blocking antibody that reduces or prevents OPN from binding to one or more of its ligands, reduces intracellular signaling modulated by OPN, or a combination thereof.

As discussed above, OPN binds integrins αvβ1, αvβ3, αvβ5, α4β1, α5β1, α8β1, and α9β1, and the hyaluronic acid receptor CD44. Thus, in some embodiments, a function blocking (antagonistic) OPN binding molecule reduces, inhibits, or prevent interaction between OPN and a ligand thereof such as integrins αvβ1, αvβ3, αvβ5, α4β1, α5β1, α8β1, and α9β1, and the hyaluronic acid receptor CD44.

In some embodiments, the OPN binding molecule includes some or all of the light chain CDRs, the entire light chain variable region, some or all of the heavy chain CDRs, the entire heavy chain variable region, or a combination thereof of any of mouse OPN antibody 100G2-2, 100D3-2, 103D6-1, or 89G9-1.

The OPN-binding molecules can include a CDR that is at least 45%, at least 50%, at least 55%, at least 60%, at least 65%, at least 70%, at least 75%, at least 80%, at least 85%, at least 90%, at least 95%, or at least 99% identical to the amino acid sequence of a CDR of the above-listed clones and which exhibit immunospecific binding to OPN.

For example, the disclosed molecules can include one or more of the light chain CDR having the amino acid sequences of any of SEQ ID NO: 14-16, 20-22, 26-28, and 32-34. The molecule can include at least one light chain CDR1, one light chain CDR2, and one light chain CDR3. For example, the molecule can include a light chain CDR1 including an amino acid sequence selected from the group consisting of SEQ ID NO:14, 20, 26, and 32. The molecule can include a light chain CDR2 including an amino acid sequence selected from the group consisting of SEQ ID NO:15, 21, 27, and 33. The molecule can include a light chain CDR3 including an amino acid sequence selected from the group consisting of SEQ ID NO:16, 22, 28, and 34.

The disclosed molecules can include one or more of the heavy chain CDR having the amino acid sequences of any of SEQ ID NO:17-19, 23-25, 29-31, and 35-37. The molecule can include at least one heavy chain CDR1, one heavy chain CDR2, and one heavy chain CDR3. The molecule can include a heavy chain CDR1 including an amino acid sequence selected from the group consisting of SEQ ID NO:17, 23, 29, and 35. The molecule can include a heavy chain CDR2 including an amino acid sequence selected from the group consisting of SEQ ID NO:18, 24, 30, and 36. The molecule can include a heavy chain CDR3 including an amino acid sequence selected from the group consisting of SEQ ID NO:19, 25, 31, and 37.

The OPN-binding molecules can include an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, at least 99%, or 100% identical to the amino acid sequence of the variable heavy chain and/or light chain of the antibody produced by any of the above clones, and which exhibits immunospecific binding to human OPN.

For example, the disclosed OPN-binding molecules can include a light chain variable region having the amino acids sequence of SEQ ID NO:6, 8, 10, and 12, or a variant thereof comprising at least 50%, 60%, 70%, 80%, 85%, 90%, 95%, 99%, or more sequence identity to SEQ ID NO: 6, 8, 10, or 12, and which exhibits immunospecifically binding to OPN.

Additionally or alternatively the disclosed OPN-binding molecules can include a heavy chain variable region having the amino acids sequence of SEQ ID NO:7, 9, 11, and 13, or a variant thereof comprising at least 50%, 60%, 70%, 80%, 85%, 90%, 95%, 99%, or more sequence identity to SEQ ID NO: 7, 9, 11, or 13, and which exhibits immunospecifically binding to OPN.

The OPN-binding molecule can be an immunoglobulin molecule (e.g., an antibody, diabody, fusion protein, etc.) that includes one, two or three light chain CDRs and one, two or three heavy chain CDRs (e.g., in some embodiments, three light chain CDRs and three heavy chain CDRs), wherein the light chain CDRs include:

(1) the light chain CDR1 of murine anti-human OPN antibody, 100G2-2, 100D3-2, 103D6-1, or 89G9-1, or a humanized variant thereof;

(2) the light chain CDR2 of murine anti-human OPN antibody 100G2-2, 100D3-2, 103D6-1, or 89G9-1, or a humanized variant thereof;

(3) the light chain CDR3 of murine anti-human OPN antibody 100G2-2, 100D3-2, 103D6-1, or 89G9-1, or a humanized variant thereof;

(4) the light chain CDR1 and the light chain CDR2 of mouse anti-human OPN antibody 100G2-2, 100D3-2, 103D6-1, or 89G9-1, or a humanized variant thereof;

(5) the light chain CDR1 and the light chain CDR3 of mouse anti-human OPN antibody 100G2-2, 100D3-2, 103D6-1, or 89G9-1, or a humanized variant thereof;

(6) the light chain CDR2 and the light chain CDR3 of mouse anti-human OPN antibody 100G2-2, 100D3-2, 103D6-1, or 89G9-1, or a humanized variant thereof; or (7) the light chain CDR1, the light chain CDR2, and the light chain CDR3 mouse of anti-human OPN antibody 100G2-2, 100D3-2, 103D6-1, or 89G9-1, or humanized variant thereof.

The molecule can be an immunoglobulin molecule includes one, two or three light chain CDRs and one, two or three heavy chain CDRs (e.g., in some embodiments, three light chain CDRs and three heavy chain CDRs), wherein the heavy chain CDRs include:

(1) the heavy chain CDR1 of murine anti-human OPN antibody 100G2-2, 100D3-2, 103D6-1, or 89G9-1, or a humanized variant thereof;

(2) the heavy chain CDR2 of murine anti-human OPN antibody 100G2-2, 100D3-2, 103D6-1, or 89G9-1, or a humanized variant thereof;

(3) the heavy chain CDR3 of murine anti-human OPN antibody 100G2-2, 100D3-2, 103D6-1, or 89G9-1, or a humanized variant thereof;

(4) the heavy chain CDR1 and the heavy chain CDR2 of murine anti-human OPN antibody 100G2-2, 100D3-2, 103D6-1, or 89G9-1, or a humanized variant thereof;

(5) the heavy chain CDR1 and the heavy chain CDR3 of murine anti-human OPN antibody 100G2-2, 100D3-2, 103D6-1, or 89G9-1, or a humanized variant thereof;

(6) the heavy chain CDR2 and the heavy chain CDR3 of murine anti-human OPN antibody 100G2-2, 100D3-2, 103D6-1, or 89G9-1, or a humanized variant thereof; or (7) the heavy chain CDR1, the heavy chain CDR2, and the heavy chain CDR3 murine anti-human OPN antibody 100G2-2, 100D3-2, 103D6-1, or 89G9-1, or a humanized variant thereof.

The molecule can be an immunoglobulin molecule that includes one, two or three light chain CDRs and one, two or three heavy chain CDRs (e.g., in some embodiments, three light chain CDRs and three heavy chain CDRs), wherein the light chain CDRs include:

(1) the light chain CDR1 of murine anti-human OPN antibody 100G2-2, 100D3-2, 103D6-1, or 89G9-1, or a humanized variant thereof;

(2) the light chain CDR2 of murine anti-human OPN antibody 100G2-2, 100D3-2, 103D6-1, or 89G9-1, or a humanized variant thereof;

(3) the light chain CDR3 of murine anti-human OPN antibody 100G2-2, 100D3-2, 103D6-1, or 89G9-1, or a humanized variant thereof;

(4) the light chain CDR1 and the light chain CDR2 of murine anti-human OPN antibody 100G2-2, 100D3-2, 103D6-1, or 89G9-1, or a humanized variant thereof;

(5) the light chain CDR1 and the light chain CDR3 of murine anti-human OPN antibody 100G2-2, 100D3-2, 103D6-1, or 89G9-1, or a humanized variant thereof;

(6) the light chain CDR2 and the light chain CDR3 of murine anti-human OPN antibody 100G2-2, 100D3-2, 103D6-1, or 89G9-1, or a humanized variant thereof; or (7) the light chain CDR1, the light chain CDR2, and the light chain CDR3 of murine anti-human OPN antibody 100G2-2, 100D3-2, 103D6-1, or 89G9-1, or a humanized variant thereof, and wherein the heavy chain CDRs include:

(1) the heavy chain CDR1 of murine anti-human OPN antibody 100G2-2, 100D3-2, 103D6-1, or 89G9-1, or a humanized variant thereof;

(2) the heavy chain CDR2 of murine anti-human OPN antibody 100G2-2, 100D3-2, 103D6-1, or 89G9-1, or a humanized variant thereof;

(3) the heavy chain CDR3 of murine anti-human OPN antibody 100G2-2, 100D3-2, 103D6-1, or 89G9-1, or a humanized variant thereof;

(4) the heavy chain CDR1 and the heavy chain CDR2 of murine anti-human OPN antibody 100G2-2, 100D3-2, 103D6-1, or 89G9-1, or a humanized variant thereof;

(5) the heavy chain CDR1 and the heavy chain CDR3 of murine anti-human OPN antibody 100G2-2, 100D3-2, 103D6-1, or 89G9-1, or a humanized variant thereof;

(6) the heavy chain CDR2 and the heavy chain CDR3 of murine anti-human OPN antibody 100G2-2, 100D3-2, 103D6-1, or 89G9-1, or a humanized variant thereof; or (7) the heavy chain CDR1, the heavy chain CDR2, and the heavy chain CDR3 of murine anti-human OPN antibody 100G2-2, 100D3-2, 103D6-1, or 89G9-1, or a humanized variant thereof.

For example, the antibody can have one or more CDR of murine 100G2-2, 100D3-2, 103D6-1, or 89G9-1, or a chimeric antibody thereof, or a humanized variant having the CDR(s) corresponding to the CDR(s) of murine anti-human OPN antibody 100G2-2, 100D3-2, 103D6-1, or 89G9-1.

One embodiment provides a humanized monoclonal antibody having a variable light chain amino acid sequence that is at least 45%, at least 50%, at least 55%, at least 60%, at least 65%, at least 70%, at least 75%, at least 80%, at least 85%, at least 90%, at least 95%, at least 99%, or 100% identical to the amino acid sequence selected from the group consisting of SEQ ID NO: 6, 8, 10, or 12 and/or a variable heavy chain amino acid sequence that is at least 45%, at least 50%, at least 55%, at least 60%, at least 65%, at least 70%, at least 75%, at least 80%, at least 85%, at least 90%, at least 95%, at least 99%, or 100% identical to the amino acid sequence selected from the group consisting of SEQ ID NO:7, 9, 11, or 13.

3. Antibody Compositions

The disclosed anti-OPN antibodies or antigen binding fragments thereof include whole immunoglobulin (i.e., an intact antibody) of any class, fragments thereof, and synthetic proteins containing at least the antigen binding variable domain of an antibody. In some embodiments, the disclosed antibody contains both an antibody light chain as well as at least the variable domain of an antibody heavy chain. In other embodiments, such molecules can further include one or more of the CH1, hinge, CH2, CH3, and CH4 regions of the heavy chain (especially, the CH1 and hinge regions, or the CH1, hinge and CH2 regions, or the CH1, hinge, CH2 and CH3 regions). The antibody can be selected from any class of immunoglobulins, including IgM, IgG, IgD, IgA and IgE, and any isotype, including $IgG_1$, $IgG_2$, $IgG_3$ and $IgG_4$. In some embodiments, the constant domain is a complement fixing constant domain where it is desired that the antibody exhibit cytotoxic activity, and the class is typically $IgG_1$. In other embodiments, where such cytotoxic activity is not desirable, the constant domain can be of the $IgG_2$ or $IgG_4$ class. The antibody can include sequences from more than one class or isotype, and selecting particular constant domains to optimize desired effector functions is within the ordinary skill in the art.

The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Some embodiments provide fragments of the anti-OPN antibodies which have bioactivity. The fragments, whether attached to other sequences or not, may include insertions, deletions, substitutions, or other selected modifications of particular regions or specific amino acids residues, provided the activity of the fragment is not significantly altered or impaired compared to the non-modified antibody or antibody fragment.

Another embodiment provides a monoclonal antibody specific to OPN that induces an activating signal to immune cells. The monoclonal antibody can be obtained from a substantially homogeneous population of antibodies, i.e., the individual antibodies within the population are identical except for possible naturally occurring mutations that may be present in a small subset of the antibody molecules.

Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

a. Chimeric and Humanized Antibodies

Another embodiment provides chimeric anti-OPN antibodies and antigen binding fragments thereof including one or more of the disclosed sequences and functional variants thereof are also provided that bind to OPN and cause an activating signal to be transmitted in to an immune cell expressing OPN.

Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 6,311,415, 5,807, 715, 4,816,567, and 4,816,397. Chimeric antibodies including one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, Molecular Immunology 28(4/5):489-498; Studnicka et al., 1994, Protein Engineering 7:805; and Roguska et al., 1994, Proc. Natl. Acad. Sci. USA 91:969), and chain shuffling (U.S. Pat. No. 5,565,332).

The disclosed anti-OPN antibodies or antigen binding fragments thereof can be human or humanized antibodies, or antigen binding fragments thereof. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art, see, for example, European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, Molecular Immunology 28(4/5):489-498; Studnicka et al., 1994, Protein Engineering 7(6):805-814; Roguska et al., 1994, PNAS 91:969-973; Tan et al., 2002, J. Immunol. 169:1119-1125; Caldas et al., 2000, Protein Eng. 13:353-360; Morea et al., 2000, Methods 20:267-79; Baca et al., 1997, J. Biol. Chem. 272:10678-10684; Roguska et al., 1996, Protein Eng. 9:895-904; Couto et al., 1995, Cancer Res. 55 (23 Supp):5973s-5977s; Couto et al., 1995, Cancer Res. 55:1717-22; Sandhu, 1994, Gene 150:409-10; Pedersen et al., 1994, J. Mol. Biol. 235:959-973; Jones et al., 1986, Nature 321:522-525; Reichmann et al., 1988, Nature 332:323-329; and Presta, 1992, Curr. Op. Struct. Biol. 2:593-596).

Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a non-human antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies can be very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

A human, humanized or chimeric antibody derivative can include substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Such antibodies can also include at least a portion of an immunoglobulin constant region (Fc), typically that of a human immunoglobulin. The constant domains of such antibodies can be selected with respect to the proposed function of the antibody, in particular the effector function which may be required. In some embodiments, the constant domains of such antibodies are or can include human IgA, IgD, IgE, IgG or IgM domains. In a specific embodiment, human IgG constant domains, especially of the IgG1 and IgG3 isotypes are used, when the humanized antibody derivative is intended for a therapeutic use and antibody effector functions such as antibody-dependent cell-mediated cytotoxicity (ADCC) and complement-dependent cytotoxicity (CDC) activity are needed. In alternative embodiments, IgG2 and IgG4 isotypes are used when the antibody is intended for therapeutic purposes and antibody effector function is not required. Fc constant domains including one or more amino acid modifications which alter antibody effector functions such as those disclosed in U.S. Patent Application Publication Nos. 2005/0037000 and 2005/0064514.

The framework and CDR regions of a humanized antibody need not correspond precisely to the parental sequences, e.g., the donor CDR or the consensus framework can be mutagenized by substitution, insertion or deletion of at least one residue so that the CDR or framework residue at that site does not correspond to either the consensus or the donor antibody. In some embodiments, such mutations are not extensive. Usually, at least 75% of the humanized antibody residues will correspond to those of the parental framework region (FR) and CDR sequences, more often 90%, or greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, *Molecular Immunology* 28(4/5):489-498; Studnicka et al., 1994, *Protein Engineering* 7(6):805-814; and Roguska et al., 1994, *Proc. Natl. Acad. Sci.* 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55 (23 Supp):5973s-5977s, Couto et al., 1995, *Cancer Res.* 55:1717-22, Sandhu, 1994, *Gene* 150:409-10, Pedersen et al., 1994, *J. Mol. Biol.* 235:959-73, Jones et al., 1986, *Nature* 321:522-525, Riechmann et al., 1988, *Nature* 332:323, and Presta, 1992, *Curr. Op. Struct. Biol.* 2:593-596.

Often, framework residues in the framework regions will be substituted with the corresponding residue from the CDR donor antibody to alter, for example improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, *Nature* 332:323).

Human, chimeric or humanized derivatives of the disclosed murine anti-human OPN antibodies can be used for in vivo methods in humans. Murine antibodies or antibodies of other species can be advantageously employed for many uses (for example, in vitro or in situ detection assays, acute in vivo use, etc.). Such a human or humanized antibody can include amino acid residue substitutions, deletions or additions in one or more non-human CDRs. The humanized antibody derivative can have substantially the same binding, stronger binding or weaker binding when compared to a non-derivative humanized antibody. In specific embodiments, one, two, three, four, or five amino acid residues of the CDR have been substituted, deleted or added (i.e., mutated). Completely human antibodies are particularly desirable for therapeutic treatment of human subjects.

Such human antibodies can be made by a variety of methods known in the art including phage display methods using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Such human antibodies can be produced using transgenic mice which are incapable of expressing functional endogenous immunoglobulins, but which can express human immunoglobulin genes.

For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies can be engaged to provide human antibodies directed against a selected antigen using technology similar to that described above.

DNA sequences coding for human acceptor framework sequences include but are not limited to FR segments from the human germline VH segment VH1-18 and JH6 and the human germline VL segment VK-A26 and JK4. In a specific embodiment, one or more of the CDRs are inserted within framework regions using routine recombinant DNA techniques. The framework regions can be naturally occurring or consensus framework regions, and human framework regions (see, e.g., Chothia et al., 1998, *"Structural Determinants In The Sequences Of Immunoglobulin Variable Domain,"* J. Mol. Biol. 278: 457-479 for a listing of human framework regions).

b. Single-Chain Antibodies

Another embodiment provides single-chain antibodies specific to OPN. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

c. Monovalent Antibodies

In vitro methods are also suitable for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the F(ab')$_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')$_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

d. Hybrid Antibodies

The antibody can be a hybrid antibody. In hybrid antibodies, one heavy and light chain pair is homologous to that found in an antibody raised against one epitope, while the other heavy and light chain pair is homologous to a pair found in an antibody raised against another epitope. This results in the property of multi-functional valency, i.e., ability to bind at least two different epitopes simultaneously. Such hybrids can be formed by fusion of hybridomas producing the respective component antibodies, or by recombinant techniques. Such hybrids may, of course, also be formed using chimeric chains.

e. Conjugates or Fusions of Antibody Fragments

The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

Such coupling of the antibody or fragment with the therapeutic agent can be achieved by making an immunoconjugate or by making a fusion protein, or by linking the antibody or fragment to a nucleic acid such as an siRNA, comprising the antibody or antibody fragment and the therapeutic agent.

In some embodiments, the antibody is modified to alter its half-life. In some embodiments, it is desirable to increase the half-life of the antibody so that it is present in the circulation or at the site of treatment for longer periods of time. For example, it may be desirable to maintain titers of the antibody in the circulation or in the location to be treated for extended periods of time. Antibodies can be engineered with Fc variants that extend half-life, e.g., using Xtend™ antibody half-life prolongation technology (Xencor, Monrovia, California). In other embodiments, the half-life of the anti-DNA antibody is decreased to reduce potential side effects. The conjugates disclosed can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

4. Fusion Proteins

In some embodiments, the OPN binding molecule is an OPN fusion protein. Fusion proteins containing OPN polypeptides coupled to other polypeptides to form fusion proteins are provided. OPN fusion polypeptides can have a first fusion partner comprising all or a part of a OPN protein fused (i) directly to a second polypeptide or, (ii) optionally, fused to a linker peptide sequence that is fused to the second polypeptide. The fusion proteins optionally contain a domain that functions to dimerize or multimerize two or more fusion proteins. In some embodiments the fusion protein is not or does not dimerize or multimerize. The peptide/polypeptide linker domain can either be a separate domain, or alternatively can be contained within one of one of the other domains (OPN polypeptide or second polypeptide) of the fusion protein. Similarly, the domain that functions to dimerize or multimerize the fusion proteins can either be a separate domain, or alternatively can be contained within one of one of the other domains (OPN polypeptide, second polypeptide or peptide/polypeptide linker domain) of the fusion protein. In some embodiments, the dimerization/multimerization domain and the peptide/polypeptide linker domain are the same.

Fusion proteins disclosed herein are of formula I:

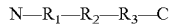

$$N-R_1-R_2-R_3-C$$

wherein "N" represents the N-terminus of the fusion protein, "C" represents the C-terminus of the fusion protein, "$R_1$" is a OPN polypeptide, "$R_2$" is an optional peptide/polypeptide linker domain, and "$R_3$" is a second polypeptide. Alternatively, $R_3$ may be the OPN polypeptide and $R_1$ may be the second polypeptide.

The fusion proteins can be dimerized or multimerized. Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric. As discussed above, in some embodiments the fusion protein is not or does not dimerize or multimerize.

In some embodiments, the second polypeptide contains one or more domains of an immunoglobulin heavy chain constant region, for example an amino acid sequence corresponding to the hinge, $C_H2$ and/or $C_H3$ regions of a human immunoglobulin Cγ1 chain, the hinge, $C_H2$ and/or $C_H3$ regions of a murine immunoglobulin Cγ2a chain, $C_H2$ and/or $C_H3$ regions of a human immunoglobulin Cγ1, etc.

The Fc portion of the fusion protein may be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, et al., *Mol. Immun.*, 34(6):441-452 (1997), Swann, et al., *Cur. Opin. Immun.*, 20:493-499 (2008), and Presta, *Cur. Opin. Immun.* 20:460-470 (2008). In some embodiments the Fc region is the native IgG1, IgG2, or IgG4 Fc region. In some embodiments the Fc region is a hybrid, for example a chimeric consisting of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region may include the entire hinge region, or less than the entire hinge region.

The disclosed fusion proteins optionally contain a peptide or polypeptide linker domain that separates the OPN polypeptide from the second polypeptide. In some embodiments, the linker domain contains the hinge region of an immunoglobulin. In a preferred embodiment, the hinge region is derived from a human immunoglobulin. Suitable human immunoglobulins that the hinge can be derived from include IgG, IgD and IgA. In a preferred embodiment, the hinge region is derived from human IgG. Amino acid sequences of immunoglobulin hinge regions and other domains are well known in the art.

5. Methods of Making

The OPN-binding molecules can be produced by any method known in the art useful for the production of polypeptides, e.g., in vitro synthesis, recombinant DNA production, and the like. The humanized antibodies are typically produced by recombinant DNA technology. The antibodies can be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., *Gene Expression Technology Methods in Enzymology* Vol. 185 Academic Press (1991), and Borreback, *Antibody Engineering*, W. H. Freeman (1992). *Additional information concerning the generation, design and expression of recombinant antibodies can be found in Mayforth, Designing Antibodies*, Academic Press, San Diego (1993).

An exemplary process for the production of the recombinant chimeric antibodies can include the following: a) constructing, by conventional molecular biology methods, an expression vector that encodes and expresses an antibody heavy chain in which the CDRs and variable region of an anti-OPN antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-human OPN monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized antibodies can include the following: a) constructing, by conventional molecular biology methods, an expression vector that encodes and expresses an anti-human OPN heavy chain in which the CDRs and a minimal portion of the variable region framework that are required to retain donor antibody binding specificity are derived from the humanized variants of anti-human OPN antibody(ies), and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as the disclosed murine anti-human OPN antibodies, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells can be co-transfected with such expression vectors, which can contain different selectable markers but, with the exception of the heavy and light chain coding sequences, can be identical. This procedure provides for equal expression of heavy and light chain polypeptides. Alternatively, a single vector can be used which encodes both heavy and light chain polypeptides. The coding sequences for the heavy and light chains can include cDNA or genomic DNA or both. The host cell used to express the recombinant antibody can be either a bacterial cell such as *Escherichia coli*, or a eukaryotic cell (e.g., a Chinese hamster ovary (CHO) cell or a HEK-293 cell). The choice of expression vector is dependent upon the choice of host cell, and can be selected so as to have the desired expression and regulatory characteristics in the selected host cell. Other cell lines that can be used include, but are not limited to, CHO-K1, NSO, and PER.C6 (Crucell, Leiden, Netherlands).

Any of the disclosed antibodies can be used to generate anti-idiotype antibodies using techniques well known to those skilled in the art (see, e.g., Greenspan, N. S. et al. (1989) "*Idiotypes: Structure And Immunogenicity*," FASEB J. 7:437-444; and Nisinoff, A. (1991) "*Idiotypes: Concepts And Applications,*" J. Immunol. 147(8):2429-2438).

C. Pharmaceutical Compositions

Pharmaceutical compositions including the disclosed OPN immunomodulatory agents are provided. Pharmaceutical compositions containing the immunomodulatory agent can be for administration by parenteral (intramuscular, intraperitoneal, intravenous (IV) or subcutaneous injection) routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed immunomodulatory agents, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed immunomodulatory agents, generally dosage levels of 0.001 to 20 mg/kg of body weight daily are administered to mammals. Generally, for intravenous injection or infusion, dosage may be lower.

In certain embodiments, the immunomodulatory agent is administered locally, for example by injection directly into a site to be treated. Typically, the injection causes an increased localized concentration of the immunomodulatory agent composition which is greater than that which can be achieved by systemic administration. The immunomodulatory agent compositions can be combined with a matrix as described above to assist in creating an increased localized concentration of the polypeptide compositions by reducing the passive diffusion of the polypeptides out of the site to be treated.

1. Formulations for Parenteral Administration

In some embodiments, the disclosed antibody and fusion protein compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Controlled Delivery Polymeric Matrices

The antibody and fusion protein compositions disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5:13-22 (1987); Mathiowitz, et al., *Reactive Polymers*, 6:275-283 (1987); and Mathiowitz, et al., *J. Appl. Polymer Sci.*, 35:755-774 (1988).

The devices can be formulated for local release to treat the area of implantation or injection—which will typically deliver a dosage that is much less than the dosage for

III. Methods of Use

The disclosed antibodies and antigen binding fragments thereof can be used to modulate an immune response in a subject in need thereof. One embodiment provides a method of suppressing OPN T cell suppressive signaling to induce T cell signaling in a subject in need thereof. Without being bound to any one theory, it is believed that IRF8 functions as a repressor of OPN expression and loss of IRF8, as is seen in many cancer cells and tumor microenvironments, leads to elevated expression of OPN that acts as a potent T cell suppressor. OPN functions as a repressive ligand that negatively regulates T cell activation.

Methods of inducing or enhancing an immune response in a subject are provided. Typically, the methods include administering a subject an effective amount of one or more of the disclosed antibodies and antigen binding fragments thereof to immunospecifically bind to OPN and reduce or block the immune suppressive signal of OPN, thus promoting an immune response. The immune response can be, for example inducing, promoting or enhancing T cell activation, secretion of cytokines by immune cells, T cell proliferation. The disclosed antibodies or antigen binding fragments thereof can be administered to a subject in need thereof in an effective amount to overcome T cell suppression. Overcoming T cell suppression can be determined by measuring T cell function using known techniques.

The methods can be used in vivo or ex vivo to induce, promote, or enhance a stimulating immune response.

In some embodiments, the antibody or antigen binding fragment thereof, or nucleic acid encoding the antibody or antigen binding fragment thereof, is administered directly to the subject. In some embodiments, antibody or antigen binding fragment thereof is contacted with cells (e.g., immune cells) ex vivo, and the treat cells are administered to the subject (e.g., adoptive transfer). The antibody or antigen binding fragment thereof can enable a more robust immune response to be possible.

A. Subjects to be Treated

1. Treatment of Cancer

The disclosed antibodies, fusion proteins, and compositions thereof can be used to treat cancer. Generally, the compositions are used to stimulate or enhance an immune response to cancer in the subject by administering to the subject an amount of a disclosed antibody or antigen binding fragment thereof that reduces or blocks suppressive OPN signaling. The method can reduce one or more symptoms of the cancer.

The immune cells activated by the disclosed antibodies or fragments thereof can kill cancer cells and reduce tumor burden in a subject. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS 1/4), ovarian carcinoma antigen (CA125), prostate specific antigen (PSA), carcinoembryonic antigen (CEA), CD19, CD20, HER2/neu, etc.).

The methods and antibody and fusion protein compositions disclosed herein are useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xenoderma pegmentosum, keratoactanthoma, seminoma, thyroid follicular cancer and teratocarcinoma.

Cancers caused by aberrations in apoptosis can also be treated by the disclosed methods and compositions. Such cancers may include, but are not limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions in the ovary, bladder, breast, colon, lung, skin, pancreas, or uterus. In other specific embodiments, sarcoma, melanoma, or leukemia is treated or prevented by the methods and compositions.

Specific cancers and related disorders that can be treated or prevented by methods and compositions disclosed herein include, but are not limited to, leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (ALK) positive, large B-cell lymphoma (DLBCL); anaplastic lymphoma kinase (ALK) positive, ALK+ anaplastic large-cell lymphoma (ALCL), acute myeloid lymphoma (AML)); multiple myelomas such as, but not limited to, smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

2. Osteoporosis

Osteoporosis is characterized by progressive loss of bone architecture and mineralization leading to the loss in bone strength and an increased fracture rate. The skeleton is constantly being remodeled by a balance between osteoblasts that lay down new bone and osteoclasts that breakdown, or resorb, bone. In some disease conditions and advancing age the balance between bone formation and resorption is disrupted; bone is removed at a faster rate. Such a prolonged imbalance of resorption over formation leads to weaker bone structure and a higher risk of fractures.

It is well-known that OPN is elevated in the peripheral blood of patients with osteoporosis and is a risk factor for the development of osteoporosis. It is believed that reducing or inhibiting aberrant OPN signaling can halt or prevent the progression of osteoporosis in a subject having or at risk of having osteoporosis. In one embodiment, the disclosed anti-OPN antibodies are used to treat or prevent osteoporosis.

In one embodiment, the subject has osteoporosis caused by a hormonal imbalance. The hormonal imbalance can be due to aging or side effects of a medication. The disclosed anti-OPN antibodies can be administered to aging or elderly subjects as a prophylactic measure against osteoporosis or can be administered to men or women undergoing hormone therapy as a preventative measure against osteoporosis.

In another embodiment, the subject has osteoporosis due to long-term use of certain medications that weaken bone, such as glucocorticoids, barbiturates, gonadotropin-releasing hormone drugs, aluminum-containing antacids, certain cancer treatments, and thyroid hormones. The disclosed anti-OPN antibodies can be administered in combination with drugs known to induce osteoporosis as a preventative measure against the development of osteoporosis.

IV. Combination Therapy

The disclosed antibodies, fusion proteins, and antigen binding fragments thereof and compositions thereof can be administered to a subject in need thereof either alone or in combination with one or more additional therapeutic agents. In some embodiments, the antibodies, fusion proteins, and antigen binding fragments thereof and the additional therapeutic agent are administered separately, but simultaneously. The antibodies, fusion proteins, and antigen binding fragments thereof and the additional therapeutic agent can also be administered as part of the same composition. In other embodiments, the antibodies, fusion proteins, and antigen binding fragments thereof and the second therapeutic agent are administered separately and at different times, but as part of the same treatment regime. The additional therapeutic agents can be administered before, after, or in alternation with the administration of the disclosed antibodies and antigen binding fragments thereof.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6 7, 14, 21, 28, 35, or 48 days prior to a first administration of second agent. The antibodies and antigen binding fragments thereof can be the first or the second therapeutic agent.

The disclosed antibodies, fusion proteins, and antigen binding fragments thereof and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary additional therapeutic agents include, but are not limited to, cytokines, chemotherapeutic agents, radionuclides, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the immunomodulatory agent can be co-administered with one or more additional agents that function to enhance or promote an immune response or reduce or inhibit an immune response.

A. Chemotherapeutic Agents

The disclosed antibodies, fusions proteins, and antigen binding fragments thereof can be combined with one or more chemotherapeutic agents and pro-apoptotic agents. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

B. Checkpoint Inhibitors

1. PD-1 Antagonists

In some embodiments, the disclosed antibodies, fusion proteins, and antigen binding fragments thereof are co-administered with a PD-1 antagonist. PD-1 is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, Proc. Natl. Acad. Sci. U.S.A, 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor. Other PD-1 antagonists contemplated by the methods of this invention include antibodies that bind to PD-1 or ligands of PD-1, and other antibodies.

Suitable anti-PD-1 antibodies include, but are not limited to, those described in the following U.S. Pat. Nos. 7,332,582, 7,488,802, 7,521,051, 7,524,498, 7,563,869, 7,981,416, 8,088,905, 8,287,856, 8,580,247, 8,728,474, 8,779,105, 9,067,999, 9,073,994, 9,084,776, 9,205,148, 9,358,289, 9,387,247, 9,492,539, 9,492,540, all of which are incorporated by reference in their entireties.

See also Berger et al., Clin. Cancer Res., 14:30443051 (2008).

Exemplary anti-PD-L1 antibodies include, but are not limited to, those described in the following U.S. Pat. Nos. 8,383,796, 9,102,725, 9,273,135, 9,393,301, and 9,580,507 all of which are specifically incorporated by reference herein in their entirety.

For anti-B7-DC (also referred to as anti-PD-L2) antibodies see U.S. Pat. Nos. 7,411,051, 7,052,694, 7,390,888, 8,188,238, and 9,255,147.

Other exemplary PD-1 receptor antagonists include, but are not limited to PD-L2 polypeptides, including homologs and variants of these, as well as active fragments of any of the foregoing, and fusion proteins that incorporate any of these. In some embodiments, the fusion protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian PD-L1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as PD-L1 or B7-DC, and prevent binding to the endogenous PD-1 receptor, thereby preventing inhibitory signal transduction. PD-L1 has also been shown to bind the protein B7.1 (Butte et al., *Immunity*, Vol. 27, pp. 111-122, (2007)). Such fragments also include the soluble ECD portion of the PD-1 protein that includes mutations, such as the A99L mutation, that increases binding to the natural ligands (Molnar et al., *PNAS*, 105:10483-10488 (2008)). B7-1 or soluble fragments thereof, which can bind to the PD-L1 ligand and prevent binding to the endogenous PD-1 receptor, thereby preventing inhibitory signal transduction, are also useful.

PD-1 and PD-L1 anti-sense nucleic acids, both DNA and RNA, as well as siRNA molecules can also be PD-1 antagonists. Such anti-sense molecules prevent expression of PD-1 on T cells as well as production of T cell ligands, such as PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

2. CTLA4 Antagonists

Other molecules useful in mediating the effects of T cells in an immune response are also contemplated as additional therapeutic agents. In some embodiments, the molecule is an antagonist of CTLA4, for example an antagonistic anti-CTLA4 antibody. An example of an anti-CTLA4 antibody contemplated for use in the methods of the invention includes an antibody as described in PCT/US2006/043690 (Fischkoff et al., WO/2007/056539).

Dosages for anti-PD-1, anti-B7-H1, and anti-CTLA4 antibody, are known in the art and can be in the range of, for example, 0.1 to 100 mg/kg, or with shorter ranges of 1 to 50 mg/kg, or 10 to 20 mg/kg. An appropriate dose for a human subject can be between 5 and 15 mg/kg, with 10 mg/kg of antibody (for example, human anti-PD-1 antibody) being a specific embodiment.

Specific examples of an anti-CTLA4 antibody useful in the methods of the invention are Ipilimumab, a human anti-CTLA4 antibody, administered at a dose of, for example, about 10 mg/kg, and Tremelimumab a human anti-CTLA4 antibody, administered at a dose of, for example, about 15 mg/kg. See also Sammartino, et al., *Clinical Kidney Journal*, 3(2):135-137 (2010), published online December 2009.

In other embodiments, the antagonist is a small molecule. A series of small organic compounds have been shown to bind to the B7-1 ligand to prevent binding to CTLA4 (see Erbe et al., *J. Biol. Chem.*, 277:7363-7368 (2002). Such small organics could be administered alone or together with an anti-CTLA4 antibody to reduce inhibitory signal transduction of T cells.

3. Potentiating Agents

In some embodiments, additional therapeutic agents include a potentiating agent. The potentiating agent acts to increase efficacy the immune response up-regulator, possibly by more than one mechanism, although the precise mechanism of action is not essential to the broad practice of the present invention.

In some embodiments, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(−)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

While CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

In one embodiment low doses of CTX are used in combination with the disclosed antibodies and antigen binding fragments thereof. Low doses of CTX (<200 mg/kg) can have immune stimulatory effects, including stimulation of anti-tumor immune responses in humans and mouse models of cancer (Brode & Cooke *Crit Rev. Immunol.* 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr-1+ MDSC. These primary effects have numerous secondary effects; for example following Treg depletion macrophages produce more IFN-γ and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB1-HA tumor model, CTX treatment at Day 9 gives a 75% cure rate. Transfer of purified Treg at Day 12 almost completely inhibited the CTX response (van der Most et al. *Cancer Immunol. Immunother.* 58:1219-1228 (2009). A similar result was observed in the HHD2 tumor model: adoptive transfer of CD4+CD25+ Treg after CTX pretreatment eliminated therapeutic response to vaccine (Taieb, J. *J. Immunol.* 176:2722-2729 (2006)).

Numerous human clinical trials have demonstrated that low dose CTX is a safe, well-tolerated, and effective agent for promoting anti-tumor immune responses (Bas, & Mastrangelo *Cancer Immunol. Immunother.* 47:1-12 (1998)).

In one embodiment, the optimal dose for CTX to potentiate an anti-tumor immune response, is one that lowers overall T cell counts by lowering Treg levels below the normal range but is subtherapeutic (see Machiels et al. Cancer Res. 61:3689-3697 (2001)).

In some embodiments, CTX is used as an immunopotentiating agent at a dose of 300 mg/m$^2$. In another embodiment, for an average male (6 ft, 170 pound (78 kg) with a body surface area of 1.98 m$^2$), 300 mg/m$^2$, the dose of CTX is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al. *Cancer Res.* 61:3689-3697 (2001), Hengst et al *Cancer Res.* 41:2163-2167 (1981), Hengst *Cancer Res.* 40:2135-2141 (1980)).

For larger mammals, such as a primate, such as a human, patient, such mg/m$^2$ doses may be used but unit doses administered over a finite time interval may also be used. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

In other embodiments, the potentiating agent is an agent that reduces activity and/or number of regulatory T lymphocytes (T-regs), such as Sunitinib (SUTENT®), anti-TGFβ or Imatinib (GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g. Avastin, VEGF-Trap) (see, for example, Li et al., Vascular endothelial growth factor blockade reduces intratumoral regulatory T cells and enhances the efficacy of a GM-CSF-secreting cancer immunotherapy. Clin Cancer Res. 2006 Nov. 15; 12(22):6808-16.), anthracyclines, oxaliplatin, doxorubicin, TLR4 antagonists, and IL-18 antagonists.

EXAMPLES

Example 1: IRF8 is Essential for Tumor Rejection and Antigen-Specific CD8+ T Cell Activation Materials and Methods Mice. IRF8-KO mice were generated as previously described (32). Mice with the loxp-flanked Irf8 gene B6(Cg)-Irf8tm1.1Hm/J were generated as previously described (44). B6.Cg-Tg(Lck-cre)548Jxm/J, SJL (B6.SJL-Ptprca Pepcb/BoyJ), and C57BL/6 mice were obtained from the Jackson Laboratory. BALB/c mice were obtained from the Charles River Frederick Facility. IRF8-TKO mice were created by crossing the B6(Cg)-Irf8tm1.1Hm/J mouse with the B6.Cg-Tg(Lck-cre)548Jxm/J mouse. The IRF8-GFP reporter mice (B6(Cg)-Irf8tm2.1Hm/J) were generated as previously described (30). WT and IRF8-KO chimera mice were created by transferring 5×10$^6$ to 10×10$^6$ BM cells from C57BL/6 and IRF8-KO mice to lethally (8.5 Gy) radiated C57BL/6 recipient mice, respectively. To create mixed BM chimera mice, C57BL/6 and SJL mice were crossed to generate F1 hybrid mice. BM cells from SJL and IRF8-KO mice were then mixed (at 1:2 or 1:5 ratio of SJL/IRF8-KO) and adoptively transferred to the lethally radiated F1 hybrid mice to generate mixed chimera mice (Supplemental FIG. 3).

Statistics. Except where indicated, all statistical analyses were performed using a 2-tailed Student's t test. P value for survival analysis was calculated using a log-rank test on a Cox hazard-proportional model. Significance for activation marker kinetics was calculated using a 2-way ANOVA with Tukey's test. Significance for IFN-γ production and division index was calculated using a 1-way ANOVA with Dunnett's correction. Tumor volume was calculated as (length× width2)/2. P less than 0.05 was considered statistically significant. All data are mean±SD.

Study approval. Use of mice was performed according to protocol 2008-0162 approved by the Augusta University institutional animal use and care committee. All studies with human specimens were reviewed and determined as "not human subject research" by the Augusta University Institutional Review Board.

Activation of CD8+ T cells by vaccination in vivo. Mice were given immunizations with the OVA peptide (SIINFEKL (SEQ ID NO:48)) using the reported procedures (69). The vaccine consists of a prime followed by a boost 14 days later, and is administered by injecting a mixture of the OVA peptide (100 µg, Genscript), CD40 mAb (prime 100 µg, boost 25 µg; BioXcell), and poly-IC (50 µg, Invivogen). Seven days after each vaccination, blood cells were collected and stained with MHCII-, CD45.1-, CD45.2-, and CD8-specific mAbs (BioLegend) and OVA tetramer (BML Intern Corp). An Fc receptor blocker (BioLegend) was used jointly with the OVA tetramer. Stained cells were analyzed on a LSR II flow cytometer (BD Biosciences).

Cell surface marker analysis. Cells were stained with antibodies and analyzed by flow cytometry. The following antibodies and dye were obtained from BioLegend: CD4 (clone RM4-5), CD8 (clone 53-6.7), CD25 (clone PC61), CD11b (clone M1/70), Gr1 (clone RB6-8C5), Ly6G (clone 1A8), Ly6C (clone HK1.4), CD45.1 (clone A20), CD45.2 (clone 104), CD44 (clone IM7), CD62L (clone MEL-14), and Zombie Violet. Stained cells were analyzed on an Accuri C6, LSRII, or LSR Fortessa (BD Biosciences).

Results

IRF8 null mice tolerate allograft tumor. 4T1 tumor cells, a mouse tumor cell line of BALB/c origin, were orthotopically injected into the mammary gland of WT C57BL/6 mice and IRF8 knockout (IRF8-KO) mice of C57BL/6 origin. 4T1 tumors grew initially in the WT C57BL/6 mice, but were quickly rejected within 2 weeks after tumor transplant (FIGS. 1A-1C). Surprisingly, 4T1 tumors continued growing and formed relatively large tumors in all IRF8-KO mice (FIGS. 1A-1C).

IRF8-deficient mice are deficient in generation of antigen-specific CD8+ T cells. Allograft rejection is mediated by host T cells (Harper, S. J., et al., *Proc Natl Acad Sci U.S.A.,* 112(41):12788-12793 (2015)). The above observations thus suggest that IRF8 deficiency might lead to T cell functional deficiency in the IRF8-KO mice (Sun, L., et al., *PLoS One,* 11(5):e0155420 (2016)). To test this hypothesis, the ovalbumin (OVA) peptide vaccination system was used to determine IRF8 function in T cell response to antigen in vivo. WT and IRF8-KO mice were vaccinated with OVA peptide to activate CD8+ T cells. As expected, WT mice responded to the OVA peptide robustly to generate OVA-specific CD8+ T cells (FIGS. 1F-1K). In contrast, IRF8-KO mice exhibited a significantly decreased response to generate OVA-specific CD8+ T cells (FIGS. 1I-1K). A complementary approach was then taken to validate this finding. IRF8-KO chimera mice with IRF8 deficiency only in hematopoietic cells, and control WT chimera mice were vaccinated with the OVA vaccine. The WT chimera mice responded efficiently as determined by generation of OVA-specific CD8+ T cells (FIG. 1L-1M). Consistent with what was observed in IRF8-KO mice, the IRF8-KO chimera mice also generated significantly fewer OVA-specific CD8+ T cells (FIGS. 1L-1N). This data indicates that global deletion of Irf8 in mice leads to deficiency in the generation of antigen-specific CD8+ T cells in vivo.

Example 2: IRF8 Deficiency Increases $CD44^{hi}CD8^+$ Memory T Cells

Results

Figure 2G:
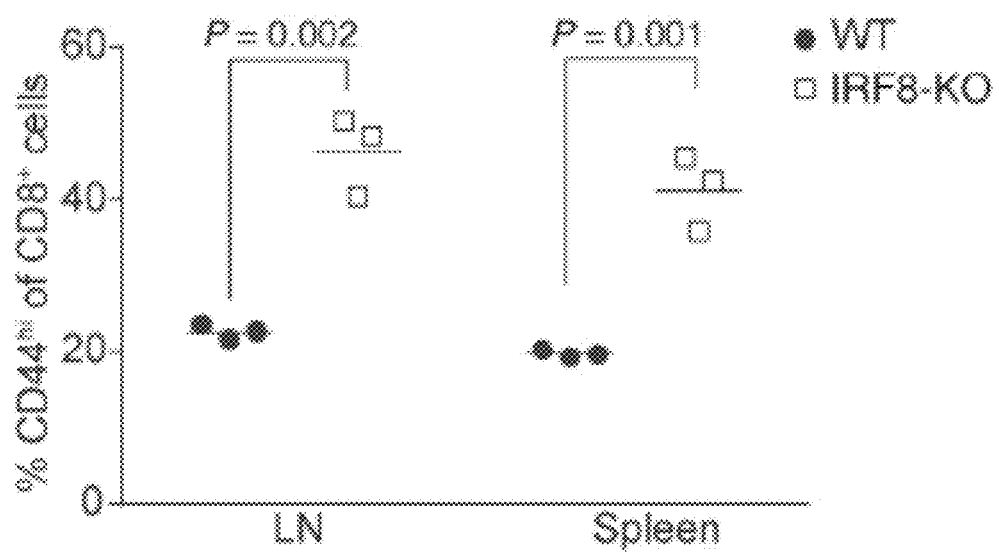
FIG. 2G is a dot plot showing the percentage of $CD8^+CD44^{hi}$ cells as shown in FIG. 2B.

IRF8-deficient CD8+ T cells have a $CD44^{hi}$ memory T cell phenotype. To identify the cellular mechanisms underlying why IRF8-deficient CD8+ T cells fail to be activated in response to antigen in vivo, flow cytometric analysis of cell surface markers on CD8+ T cells was performed comparing those from WT to IRF8-KO mice. The CD44 level is markedly different between the 2 populations (FIGS. 2A-2F). The percentage of the subset of $CD44^{hi}$ cells is significantly higher on $CD8^+$ T cells in lymphoid organs of IRF8-KO mice compared with WT mice (FIG. 2G).

Example 3: IFR8 Represses the Expression of OPN Expression in Myeloid Cells

Materials and Methods

GFP fluorescence visualization. GFP fluorescence was visualized as previously described (30). The tissues were then examined under a LSM780 Meta confocal laser microscope (Carl Zeiss). The captured images were viewed and analyzed using Zeiss Zen Meta imaging 2012 software.

Intracellular staining and flow cytometry. Cells were stained with anti-CD11b and anti-Gr1 mAbs, fixed with IC Fixation Buffer (BD Biosciences), incubated with permeabilization buffer, and stained with PE-anti-mouse OPN (catalog IC808P, R&D Systems).

IFN-γ and OPN protein analysis by ELISA. Serum and cell culture medium were analyzed for IFN-γ and OPN protein level using the mouse IFN-γ ELISA kit (catalog 430805, BioLegend), human IFN-γ ELISA kit (catalog 430105, BioLegend), mouse OPN ELISA kit (catalog MOST00, R&D Systems), and the human OPN ELISA kit (catalog DOST00, R&D Systems).

Gene expression analysis. Total RNA was isolated from cells using GenElute Direct mRNA Miniprep Kits (Sigma-Aldrich) according to the manufacturer's instructions. cDNA was synthesized using the MMLV reverse transcriptase (Promega), and used for qPCR using the StepOne Real-Time PCR system (Applied Biosystems).

Results

IRF8 regulates OPN expression in myeloid cells. CD44 is known to interact with various ligands, which are crucial for its cellular function (Baaten, B J. et al., Immunity, 32(1): 104-115 (2010); Curtsinger, J. M., et al., J Immunol, 160 (7):3236-3243 (1998)). The above observation that IRF8 deficiency leads to significantly increased $CD44^{hi}$ $CD8^+$ T cells in mice suggests that CD44 may contribute to the deficiency of CD8+ T cell activation. To test this hypothesis, the expression level of major CD44 ligands in spleen cells was analyzed. Hyaluronic acid is considered the major ligand for CD44 (Lesley, J., et al., J Exp Med, 175(1):257-266 (1992)). Quantitative polymerase chain reaction (qPCR) analysis of total spleen cells indicated that the expression levels of the major genes encoding enzymes of the hyaluronic acid metabolism pathways, including Has1, Has2, Has3, Hyal1, Hyal2, Hyal3, and Hyal5, are not significantly different between WT and IRF8-KO mice (Date not shown). OPN is a secreted matricellular protein that also acts as the physiological ligand for CD44 (Lin, Y. H., et al., J Biol Chem, 276(49):46024-46030 (2001)). qPCR analysis revealed that total spleen cells from IRF8-KO mice expressed a more than 10-fold higher level of OPN than WT spleen cells (FIG. 3A). To determine what types of cells express OPN, spleen cells were intracellularly stained for OPN concomitantly with surface staining for B cells (CD19), T cells (CD3), and myeloid cells (CD11b and Gr1). Gating OPN+ cells revealed that about 95% of OPN+ cells are CD11b+Gr1+ in IRF8-KO mice. Therefore, it was determined that these OPN+ cells are primarily CD11b+ Gr1+ myeloid cells (FIGS. 3B-3C). IRF8-KO mice have a significantly higher level of OPN+ myeloid cells than WT mice (FIG. 3D).

A complementary approach was used to further determine the relationship between IRF8 and OPN. Myeloid cells in the IRF8-GFP reporter mice (Wang, H., et al., J Immunol, 193(4):1766-1777 (2014)) were analyzed for GFP intensity (a surrogate marker for IRF8 protein level) and OPN expression level. $CD11b^+Ly6C^{lo}Ly6G^+$ myeloid cells are GFP- myeloid cells (FIGS. 3E-3F) that have a significantly higher percentage and level of OPN+ cells than the GFP+ $CD11b^+$ $Ly6C^{hi}Ly6G^-$ myeloid cells (FIGS. 3E-3H). Thus, IRF8 expression level is inversely correlated with OPN expression level under physiological conditions.

Example 4: OPN Inhibits T Cell Activation In Vitro

Results

The observations that IRF8-KO mice have a significantly higher percentage of $CD44^{hi}$ $CD8^+$ T cells than WT mice, and that the OPN expression level is significantly higher in the $CD11b^+Gr1^+$ myeloid cells in IRF8-KO mice than those in WT mice, suggest that the CD44-OPN axis may suppress $CD8^+$ T cell activation. To test this hypothesis, T cells were cultured in the presence of recombinant OPN protein and T cell proliferation was analyzed. Indeed, OPN protein reproducibly inhibited $CD8^+$ T cell activation and proliferation in a dose dependent manner (FIGS. 4A-4F). Consistent with the inhibited T cell proliferation, OPN inhibited IFN-γ production by T cells in vitro (FIG. 4G). To determine whether OPN inhibits T cell activation, T cell activation markers were analyzed. OPN decreased $CD69^+CD8^+$ T cells as early as 2 hours after stimulation (FIGS. 4H-4J). Similarly, the levels of $CD25^-$ and PD-1-expressing $CD8^+$ T cells were also decreased by OPN (FIG. 4H-4J). Taken together, these data indicate that OPN is highly expressed in $CD11b^+$ $Ly6C^{lo}Ly6G^+$ myeloid cells and acts as a potent suppressor for CD8+ T cell activation.

Example 5: IRF8 Regulates Antigen-Specific CD8+ T Cell Differentiation and Activation in a Cell-Extrinsic Manner Results The above observations that IRF8-KO mice are deficient in response to vaccine to generate antigen-specific CD8+ T cells and that OPN expression level is elevated in $CD11b^+$ Ly6C$^{lo}$Ly6G$^+$ myeloid cells in IRF8-KO mice suggest that IRF8 might regulate CD8+ T cell response to antigen in a cell-extrinsic manner. To test this hypothesis, antigen-specific CD8+ T cell response was analyzed in competitive mixed bone marrow (BM) chimeras. Chimeric mice were generated by transplanting a mixture of Irf8$^{-/-}$ (CD45.2+) BM cells and BM cells from WT SJL (B6. SJL-Ptprca Pepcb/BoyJ) congenic donors (CD45.1+) into irradiated F1 congenic recipients (CD45.1+CD45.2+). Because BM in IRF8-KO mice contains a higher level of CD11b$^+$Gr1$^+$ myeloid cells than WT mice, the number of BM cells injected from Irf8 and WT animals was mixed at adjusted ratios (2:1 of Irf8$^{-/-}$/WT) (Becker, A. M., et al., *Blood*, 119(9):2003-2012)). The development of mature T cells 8 weeks after transplantation was analyzed. Although it has been reported that the total numbers of CD4$^+$ and CD8$^+$ T cells are not markedly different between IRF8-KO and WT mice in the lymphoid organs (Holtschke, T., et al., *Cell*, 87(2):307-317 (1996)), the Irf8$^{-/-}$ BM cells exhibit a competitive disadvantage over the WT BM cells in both CD4$^+$ and CD8$^+$ T cell maturation. The levels of Irf8$^{-/-}$ CD4+ and CD8+ T cells are significantly lower than the WT CD4+ and CD8+ T cells in the mixed BM chimeras (FIGS. 5A-5C). The competitive mixed BM chimera experiment was repeated at a ratio of 5:1 of Irf8$^{-/-}$/WT, and still observed that the levels of Irf8$^{-/-}$ CD4$^+$ and CD8$^+$ T cells are significantly lower than the WT CD4$^+$ and CD8$^+$ T cells in the mixed BM chimeras. Furthermore, unlike the WT and IRF8-KO mice, there is no significant difference in CD44 expression level between WT and Irf8$^{-/-}$ CD8$^+$ T cells in the mixed BM chimeras 8 weeks after BM cell transplantation (FIGS. 5D-5G). Next, the mixed BM chimeras were vaccinated with the OVA peptide regimen. Using the same analysis strategy as in the WT and IRF8-KO mice, CD8$^+$ T cells in the MHC class II-cell population were further gated into CD45.1$^+$ (WT) and CD45.2$^+$ (Irf8$^{-/-}$) cells (FIGS. 5H-5J). Analysis of OVA$^+$ cells indicates that, although Irf8$^{-/-}$ CD8$^+$ T cells are at a lower level, these Irf8$^{-/-}$ CD8$^+$ T cells responded to the vaccine as efficiently as the WT CD8$^+$ T cells in the same host (FIGS. 5H-5J). There was no significant difference in the percentage of OVA-specific WT and Irf8$^{-/-}$ CD8$^+$ T cells (FIG. 5K).

Example 6: Mice with IRF8 Deficiency Only in T Cells Exhibit No Deficiency in Generation of Antigen-Specific CD8+ T Cells and Reject Allograft Tumor Results A complementary approach was then used to strengthen the above finding that the deficiency in generation of antigen-specific CD8$^+$ T cells in IRF8-KO mice is not due to intrinsic IRF8 function. A mouse model with IRF8 deficiency only in T cells (IRF8-TKO) was developed. Unlike the IRF8-KO mice, IRF8-TKO mice have a similar CD44$^{hi}$CD8$^+$ T cell phenotype as the WT (Lck-cre$^{+/-}$Irf8$^{+/+}$) mice (FIG. 6A). Furthermore, there are no significant differences in the percentage of OPN$^+$CD11b$^+$Gr1$^+$ myeloid cells. OPN protein levels of CD11b$^+$Gr1$^+$ myeloid cells are also not significantly different between IRF8-TKO and WT mice (FIGS. 6B-6C). Consistent with the normal CD44 and OPN expression patterns, IRF8-TKO mice responded to OVA peptide vaccination in a similar degree as the WT mice in the generation of OVA-specific CD8+ T cells (FIGS. 6D-6F).

Figure 6J:
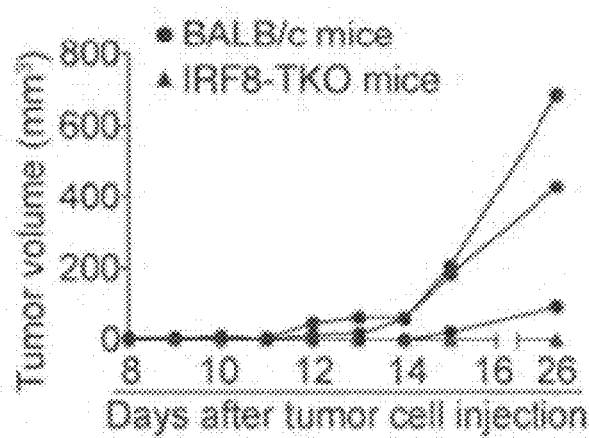
FIG. 6J is a line graph showing tumor growth over time in 4T1 tumor-bearing BALB/c and 4T1 tumor-challenged IRF8-TKO mice.
Figure 6K:
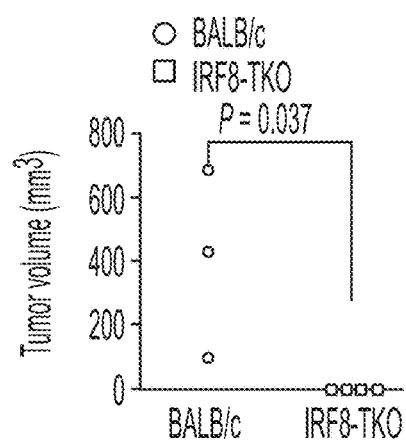
FIG. 6K is a graph of tumor volume (mm$^3$) for BALB/C and IRF8-TKO treated mice.

To determine whether IRF8-TKO mice tolerate an allograft tumor, 4T1 tumor cells were injected into IRF8-TKO mice. 4T1 tumor cells were also injected into WT BALB/c mice as an autograft tumor control. As expected, the 4T1 tumor grew aggressively in syngeneic BALB/c mice (FIGS. 6G-6I). However, unlike what was observed in IRF8-KO mice that tolerate the allograft 4T1 tumor (FIG. 1B), IRF8-TKO mice rejected the allograft 4T1 tumor completely (FIG. 6J-6K). Taken together, these data demonstrate that IRF8 regulates antigen-specific CD8$^+$ T cell activation and allograft tumor tolerance in a cell-extrinsic manner, and myeloid cell-expressed OPN may suppress CD8$^+$ T cell activation in vivo.

Example 7: IRF8 Functions as a Transcriptional Repressor of OPN in Colon Epithelial Cells Materials and Methods Mouse tumor model. Mice were injected with AOM (Sigma-Aldrich, 10 mg/kg body weight) intraperitoneally once and treated with 2.5% DSS (MP Biomedicals, 35,000-50,000 mol wt) 1 day after AOM injection for 1 week, followed by 2 weeks with sterile, untreated water. The AOM-DSS cycle was repeated 2 more times. Mice were maintained with regular drinking water after the third AOM-DSS cycle and sacrificed for analysis. 4T1 mammary carcinoma cells were obtained from American Type Culture collection (ATCC). 4T1 cells were tested for mycoplasma and were mycoplasma-free at the time of the study. 4T1 tumor cells (1×10$^4$ cells/mouse) were injected into the no. 3 mammary gland of female BALB/c mice.

SMSA of protein-DNA interactions. CD3+ T cells were purified from spleen and lymph nodes using the MojoSort CD3+ T Cell Isolation Kits as described above. T cells were activated in anti-CD3 and anti-CD28 mAb-coated plates for 3 days and used to prepare nuclear extract as previously described (70). Colon tissues were collected from mice and homogenized in a glass homogenizer for nuclear extract preparation as described (70). Complementary oligonucleotides containing the ISRE consensus sequence of the mouse Spp1 promoter (Supplemental Table 1) were synthesized and annealed to make double-stranded DNA probes. Complementary oligonucleotides containing ISRE consequence sequence of the mouse Pdcd1 promoter (Supplemental Table 1) were also synthesized and annealed to make double-stranded DNA probes. The DNA probes were end-labeled with 32P and incubated with nuclear extracts in the presence of IgG, anti-IRF8 antibody (C-19, Santa Cruz Biotechnology), or cold probes as indicated. The DNAprotein complexes were analyzed by polyacrylamide gel electrophoresis and detected by a phosphoImager.

ChIP assay. ChIP assays were carried out using the anti-IRF8 antibody (C-19, Santa Cruz Biotechnology) and protein A-agarose beads (Millipore). The mouse Spp1 promoter DNA was detected by qPCR and semiquantitative PCR using gene-specific primers.

Results

Figure 7A:
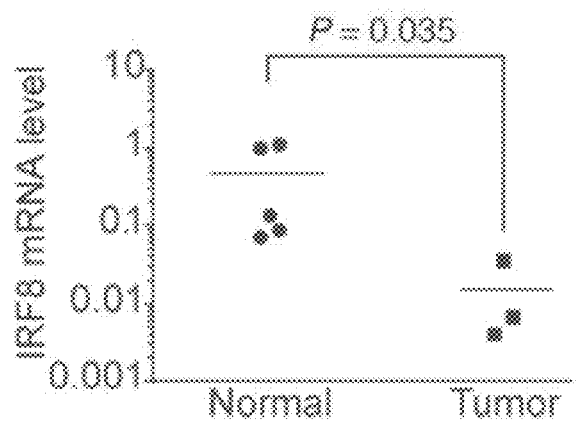
FIGS. 7A-7B are graphs showing IRF8 (FIG. 7A) and OPN (FIG. 7B) mRNA expression levels in total RNA isolated from mouse colon (n=5) and AOM-DSS-induced colon carcinoma (n=3) tissues analyzed by qPCR. Each dot represents data from one mouse. Significance was determined using the nonparametric Mann-Whitney U test.
Figure 7B:
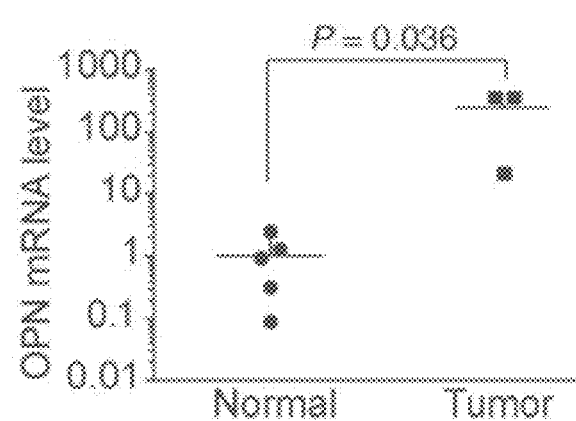
Figure 7C:
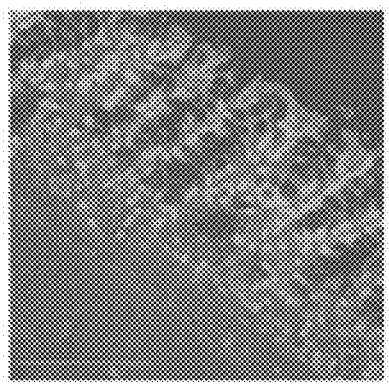
FIGS. 7C-7E are representative microscopy images of colon tissues from tumor-free IRF8-GFP reporter mice (FIG. 7C-7D; n=3) and tumor tissues from AOM-DSS-induced colon tumor mice (FIG. 7E; n=3). Scale bars: 100 µM (FIGS. 7C and 7E) and 20 µM (FIG. 7D).
Figure 7D:
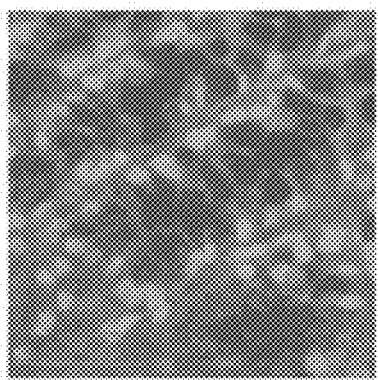
Figure 7E:
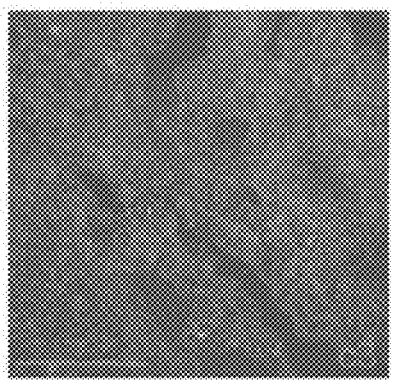
Figure 7F:
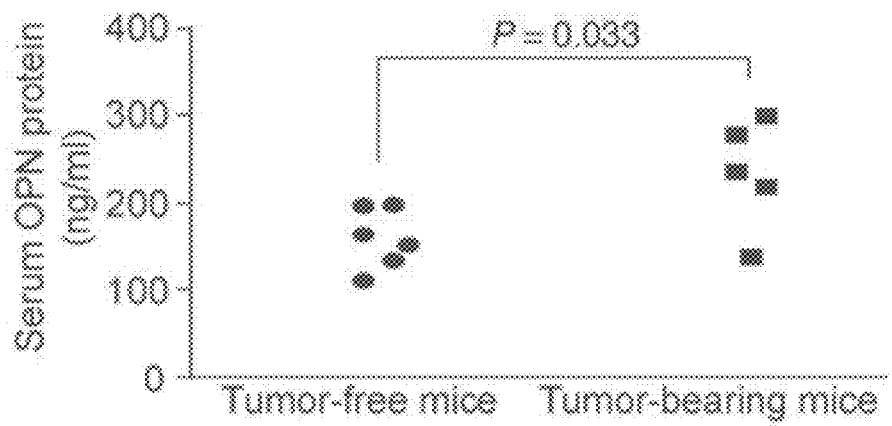
FIG. 7F is a graph showing serum OPN protein levels in serum collected from tumor-free (n=6) and AOM-DSS-induced colon tumor-bearing (n=5) mice.

The above findings determined that OPN is a potent suppressor of T cells and IRF8 functions as a repressor of OPN expression in CD11b$^+$Ly-6C$^{lo}$Ly6G$^+$ myeloid cells. In addition to being silenced in myeloid cells such as the CD11b$^+$Ly6C$^{lo}$Ly6G$^+$ myeloid cells (FIGS. 3E-3H), IRF8 is often silenced in colon carcinoma cells by DNA methylation (McGough, J. M., et al., *Mol Cancer Res*, 6(12):1841-1851 (2008)), which raises the possibility that tumor cells may also use silencing IRF8 expression as a mechanism to upregulate OPN to CTL activation in the tumor microenvironment. To test this hypothesis, a spontaneous azoxymethane-dextran sodium sulphate (AOM-DSS) colon cancer mouse model was used. Normal colon tissues and colon tumors were collected and analyzed by qPCR. As expected, IRF8 was significantly downregulated in colon tumor tissues as compared with normal colon (FIG. 7A). Consistent with what was observed in the CD11b+Ly6C$^{lo}$Ly6G+ myeloid cells, OPN expression is significantly upregulated in the tumor tissues as compared with the normal colon in vivo (FIG. 7B). Normal colon epithelial cells have a high level of IRF8 protein, but IRF8 protein is undetectable in the colon tumor cells (FIGS. 7C-7E). Consistent with the elevated OPN mRNA level in the colon tumor tissue (FIG. 7B), the OPN protein level is significantly higher in serum of the AOMDSS-induced colon tumor-bearing mice as compared with tumor free mice (FIG. 7F).

Figure 7G:
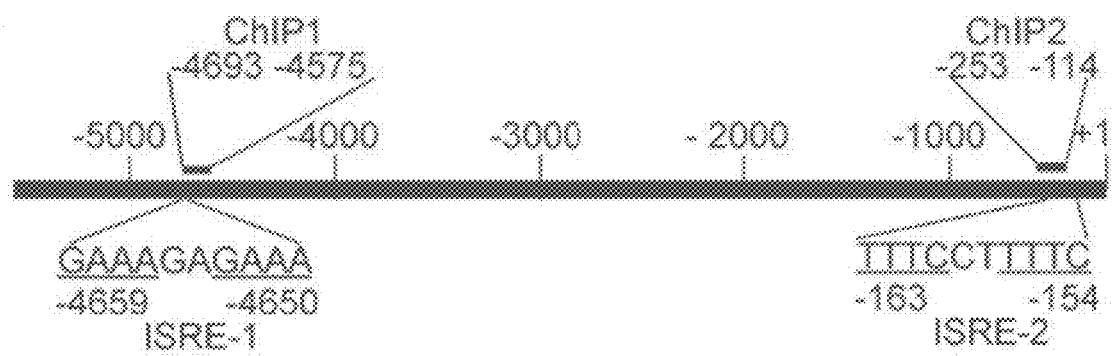
FIG. 7G is a schematic showing the Spp1 promoter structure including the 2 putative ISRE consensus sequence elements, ISRE-1 (GAAAGAGAAA (SEQ ID NO:49)) and ISRE-2 (TTTCCTTTTC (SEQ ID NO:50)). The ChIP PCR-amplified regions are also indicated. +1 indicates Spp1 gene transcription initiation site.
Figure 7H:
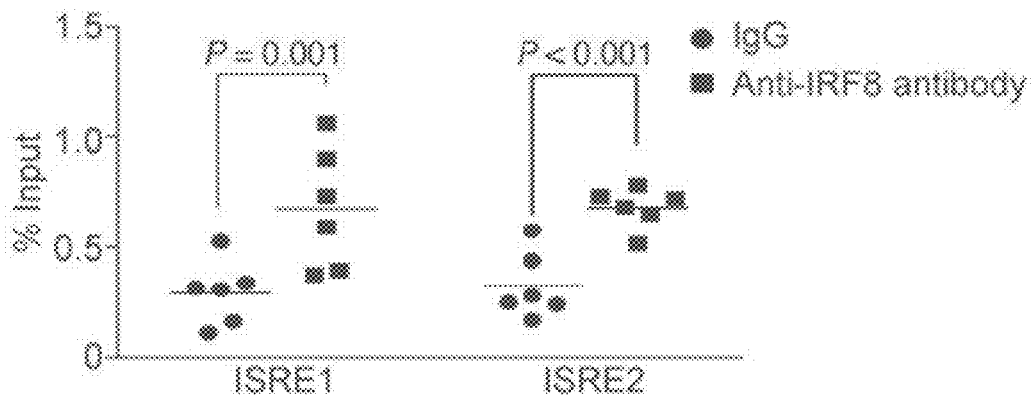
FIG. 7H is a graph showing the results of ChIP analysis of normal mouse colon tissues analyzed by ChIP using IgG (negative control) and anti-IRF8 antibody. The ChIP qPCR were normalized to input DNA.

IRF8 functions as either a transcriptional activator or repressor depending on its associated protein factors and the target gene promoter consensus sequence (Tamura, T., et al., *Blood*, 106(6):1938-1947 (2005)). The mouse Spp1 gene promoter was analyzed and 2 putative IRF8 consensus interferon-stimulated response elements (ISRE1 and ISRE2) were identified (FIG. 7G). Analysis of normal colon tissues by chromatin immunoprecipitation (ChIP) detected IRF8 association with the ISRE consensus sequence chromatin at the Spp1 promoter region (FIG. 7H). As a complementary approach, electrophoretic mobility shift assay (EMSA) was then used to determine IRF8 binding to the 2 putative ISRE elements of the Spp1 promoter. IRF8-specific antibody did not supershift the IRF8-DNA complexes when nuclear extracts from the colon were used. To determine the specific colon epithelial cell IRF8 protein complex-DNA interaction, a cold DNA probe competition approach was used. A DNA probe containing the ISRE consequence sequence element of the mouse Pdcd1 promoter was incubated with nuclear extracts from activated CD3+ T cells. Two protein-DNA complexes were detected and anti-IRF8 antibody displaced them (FIG. 7I), indicating IRF8 binding to this DNA probe. The Pdcd1 promoter ISRE-containing DNA probe was used to compete the Spp1 promoter ISRE probes. Two major protein-DNA complexes were detected when colon nuclear extract was incubated with Spp1 ISRE1 and ISRE2 DNA probes (FIG. 7I) and cold Pdcd1 ISRE DNA probe competed away the 2 protein-DNA complexes (FIGS. 7J-7K). These observations determined that IRF8 protein binds to the ISRE elements at the Spp1 promoter to repress OPN expression in colon epithelial cells.

Example 8: OPN is Elevated in Human Colon Carcinoma and Inversely Correlated with Patient Survival Materials and Methods Human colon carcinoma data set and peripheral blood specimens: The gene expression data set was extracted from the TCGA Colon and Rectal Cancer (COADREAD) data set using the Xena Functional Genomics Explorer (UCSD). Human colon cancer patient serum was obtained from the Georgia Cancer Center Biorepository (Augusta, Georgia). Human blood specimens were obtained with written informed consent from healthy donors enrolled in the Shepeard Community Blood Bank (Augusta, Georgia).

Results

Figure 8D:
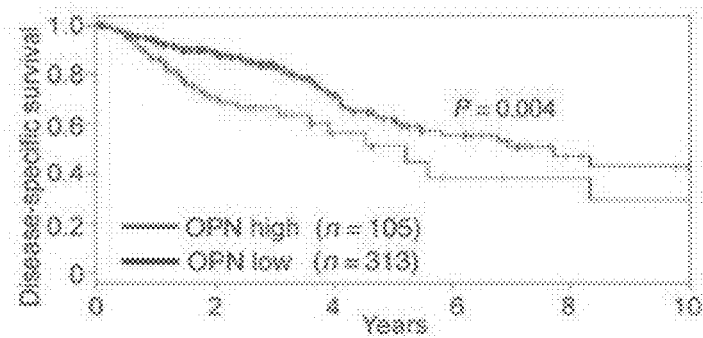
FIG. 8D is a Kaplan-Meier survival curve for human patients with colon cancer having high OPN mRNA expression levels (bottom trace) and low OPN mRNA expression levels (top trace).
Figures 8E, 8F, 8G, 8H, 8I:
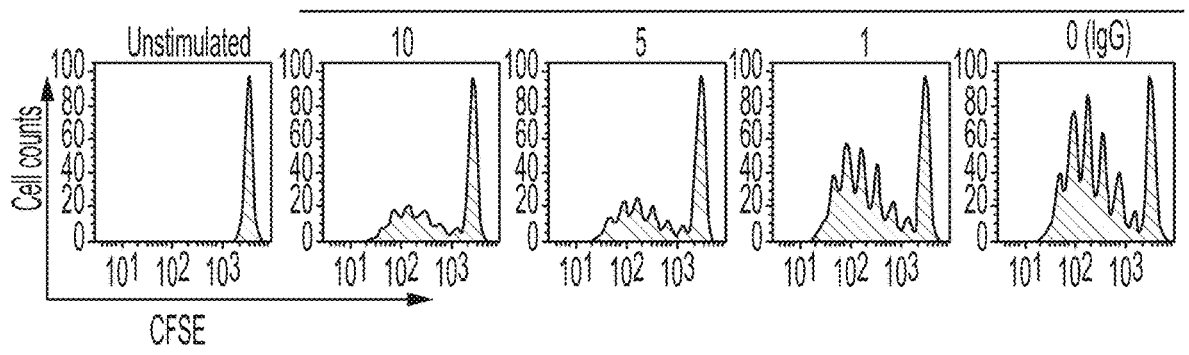
FIGS. 8E-8I are plots showing CFSE cell counts for CD3$^+$ human T cells purified from healthy donors, labeled with CFSE, and cultured in plates coated with anti-CD3 (1 µg/ml) mAb and OPN at the indicated concentrations for 3 days. The CFSE-labeled and unstimulated cells were used as control. Representative data of cells from 1 of 5 donors are shown.
Figure 8J:
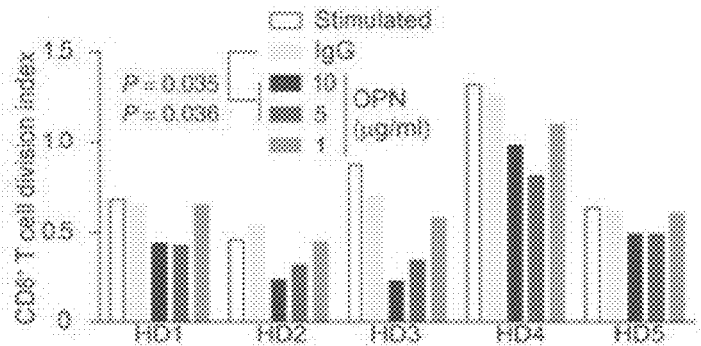
FIG. 8J is a bar graph showing CFSE intensity from FIGS. 8E-8I quantified as division index. Data from 5 healthy donors (HD1-HD5) are shown.
Figure 8K:
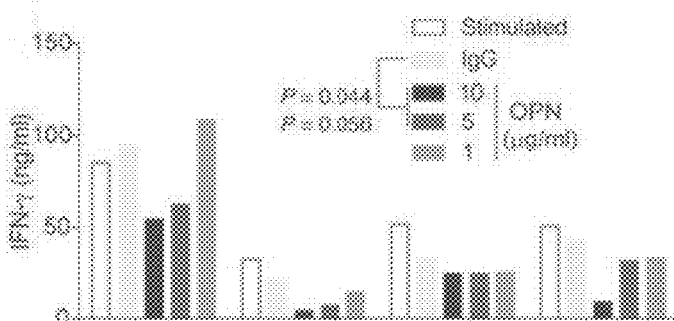
FIG. 8K is a bar graph showing IFN-γ protein level s in human CD3⁺ T cells cultured in plates coated with anti-CD3 (1 μg/ml) mAb and OPN at the indicated concentrations for 3 days. Data from 4 healthy donors are shown. Statistical significance for each treatment in FIGS. 8J and 8K was determined by ANOVA, using Dunett's test for multiple comparisons.

To determine whether the above findings can be translated to human colon cancer patients, mRNA expression data sets of colon cancer and matched normal tissues were extracted from The Cancer Genome Atlas (TCGA) data sets. IRF8 expression level is significantly downregulated in human colon carcinoma as compared with normal colon, whereas OPN expression is significantly upregulated in human colon carcinoma as compared with the normal colon (FIG. 8A-8B). As OPN is a secreted protein, it is therefore possible that OPN protein level may be elevated in patient periphery. To test this hypothesis, serum specimens from healthy donors and patients with colon cancer were analyzed. As expected, OPN protein level is significantly higher in serum from patients with colon cancer as compared with healthy donors (FIG. 8C). It was determined that OPN is a potent suppressor of CD8+ T cells (FIGS. 4A-4F) and CD8+ T cells are the primary adaptive immune cells of the host cancer immunosurveillance. It is thus likely that elevated OPN will decrease host cancer immunosurveillance to promote tumor progression. To test this hypothesis, OPN expression level and colon cancer patient clinical outcomes were analyzed. Indeed, Kaplan-Meier survival analysis revealed that OPN expression level is inversely correlated with survival time of patients with colon cancer (FIG. 8D). To determine whether OPN inhibits human CD8+ T cell activation, human T cells were activated with anti-CD3 mAb in the absence or presence of recombinant human OPN protein. Analysis of cellular proliferation indicated that OPN significantly inhibited human CD8+ T cell proliferation at a concentration of 5 µg/ml (FIGS. 8E-8J). Consistent with the decreased proliferation, OPN also significantly inhibited IFN-γ secretion by human CD8+ T cells (FIG. 8G). Taken together, the data indicates that OPN is an inhibitor of human CD8+ T cells and OPN expression is elevated in human colon cancer and secreted into the periphery. OPN promotes human colon cancer progression.

Example 9. Loss of OPN Renders Susceptibility to T-Cell Mediated Killing

Methods

OPN Expression in human cancer: Serum samples were collected from human healthy donors (Control, n=5) and human colorectal cancer patients (COAD, n=29) and levels of OPN were quantified by ELISA. Serum samples were collected from human healthy donors (healthy donor, n=20) and pancreatic cancer patients (Pancreatic Cancer, n=20) and levels of OPN were quantified by ELISA.

OPN Knockout in murine colorectal cancer cell lines: OPN was deleted in the murine colorectal cancer cell line CT26 by Crispr/Cas9 technology. Supernatant was harvested from control (CT26.ck) and osteopontin-deficient (CT26.OPKO) cell lines and OPN levels were determined by ELISA. Cell lines were co-cultured with the 2/20 T cell line overnight at indicated ratios in the presence of tumor-conditioned media, and CTL-mediated lysis was analyzed by flow cytometry. Apoptosis was determined by analyzing the % CD8a−AV+PI+ cells. N=4 for all groups tested. 2/20 cell activation at a 1:2 2/20:CT26 ratio was assessed by flow cytometry for CD25 expression on CD8a+ cells. N=4 for both groups. 1*10^6 CT26.CK or CT26.OPN.KO cells were injected i.v. into Balb/c mice. After fourteen days, lungs were harvested and fixed.

Generation of knockout cell lines. Crispr/Cas9 knockouts were generated using the lentiCRISPRv2 vector approach. SgRNAs specific to Spp1 (5'-AAGGTGAAAGTGACT-GATTC-3' (SEQ ID NO:46)) or a control sequence not present in the mouse genome (5'-CTCGTATCTTTTCC-CACGGC-3' (SEQ ID NO:47)) were purchased in the lentiCRISPRv2-Puro vector (Genscript, Piscataway). HEK293FT cells at 60-70% confluency were co-transfected with indicated lentiCRISPRv2 vectors, psPAX2 (Addgene: 12259) packaging plasmid, and pCMV-VSVg (Addgene:

8454) envelope plasmid to generate lentiviral particles. CT26 cells (ATCC, Manassas) were then transduced with these particles for forty-eight hours, then selected with 5 μg/mL of puromycin for three days.

Results

Figure 9A:
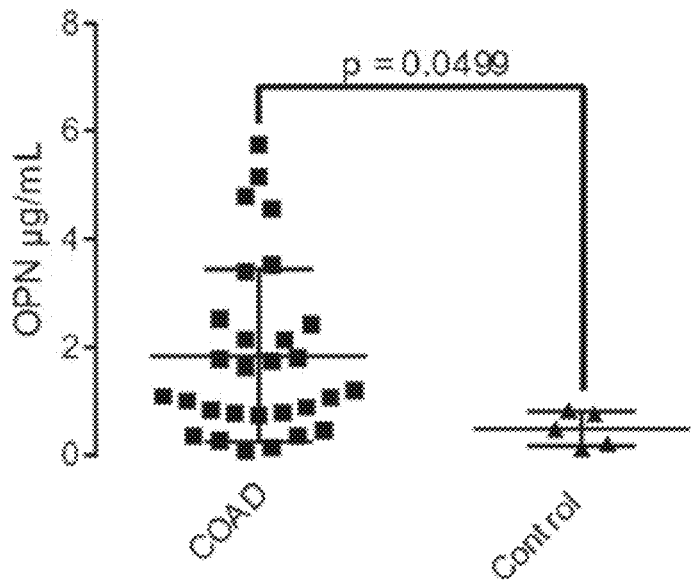
FIG. 9A is a graph showing OPN (OPN) concentration in serum from healthy donors and colorectal cancer patients.
Figure 9B:
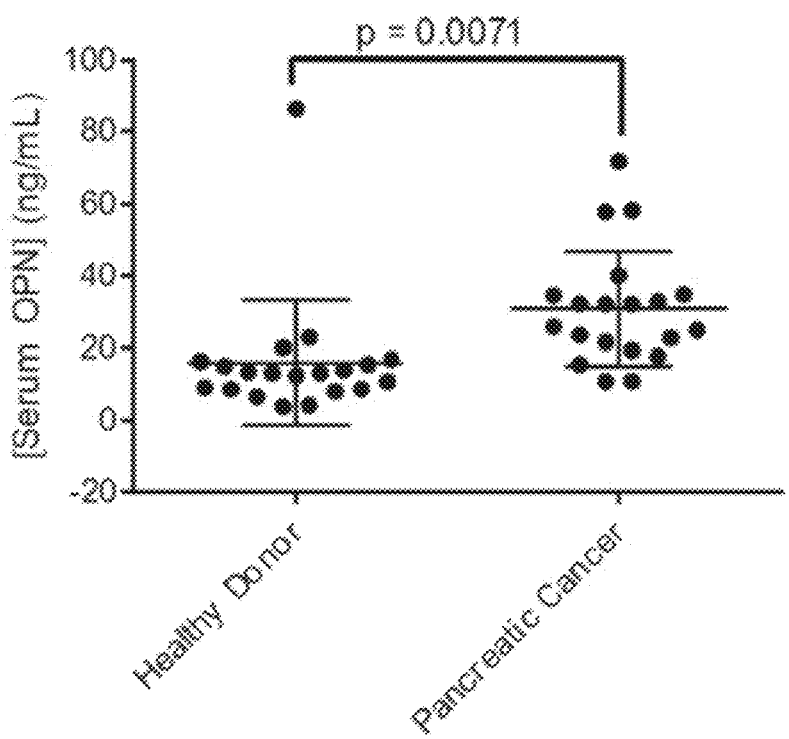
FIG. 9B is a graph showing OPN (OPN) concentration in serum from healthy donors and pancreatic cancer patients.
Figure 10:
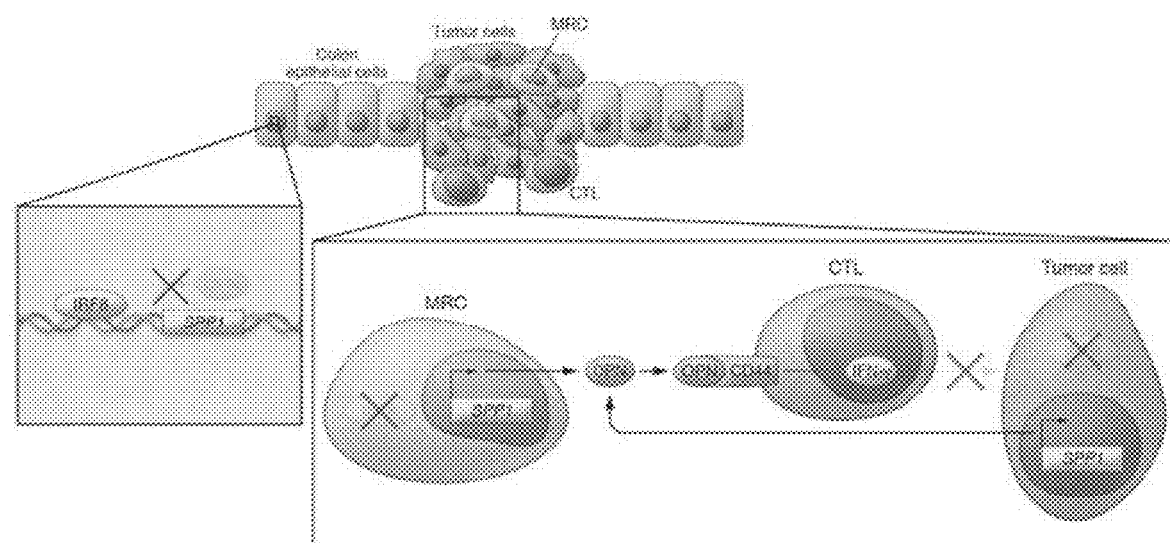
FIG. 10 is a schematic model outlining the proposed mechanism for OPN-mediated inhibition of anti-tumor immunity. It was adapted from Shurin, M R. J Clin Invest (2018). Briefly, IRF8 functions as a transcriptional repressor of OPN expression both within immunoinhibitory myeloid regulatory cells (MRCs, also known as myeloid-derived suppressor cells, or MDSCs) and colorectal cancer cells. Loss of IRF8 expression in the tumor microenvironment leads to upregulation of OPN, which can inhibit T cell functions, such as suppression of IFNγ release.
Figure 11A:
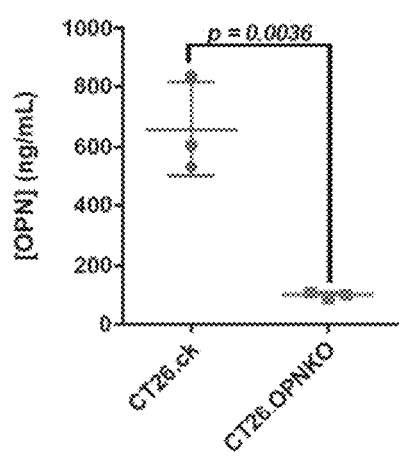
FIG. 11A is a graph showing OPN (OPN) concentration in CT26.ck and CT26.OPNKO cells.
Figure 11B:
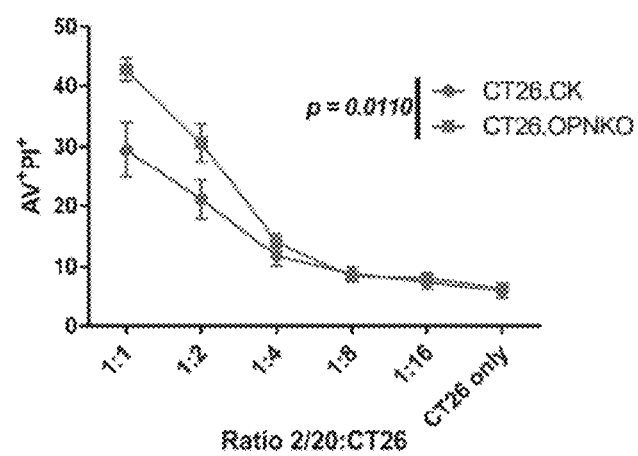
FIG. 11B is a graph showing cell viability in CT26.CK and CT26.OPNKO cells as measured by Annexin V (AV) and propidium iodide (PI) staining.
Figures 12A, 12B:
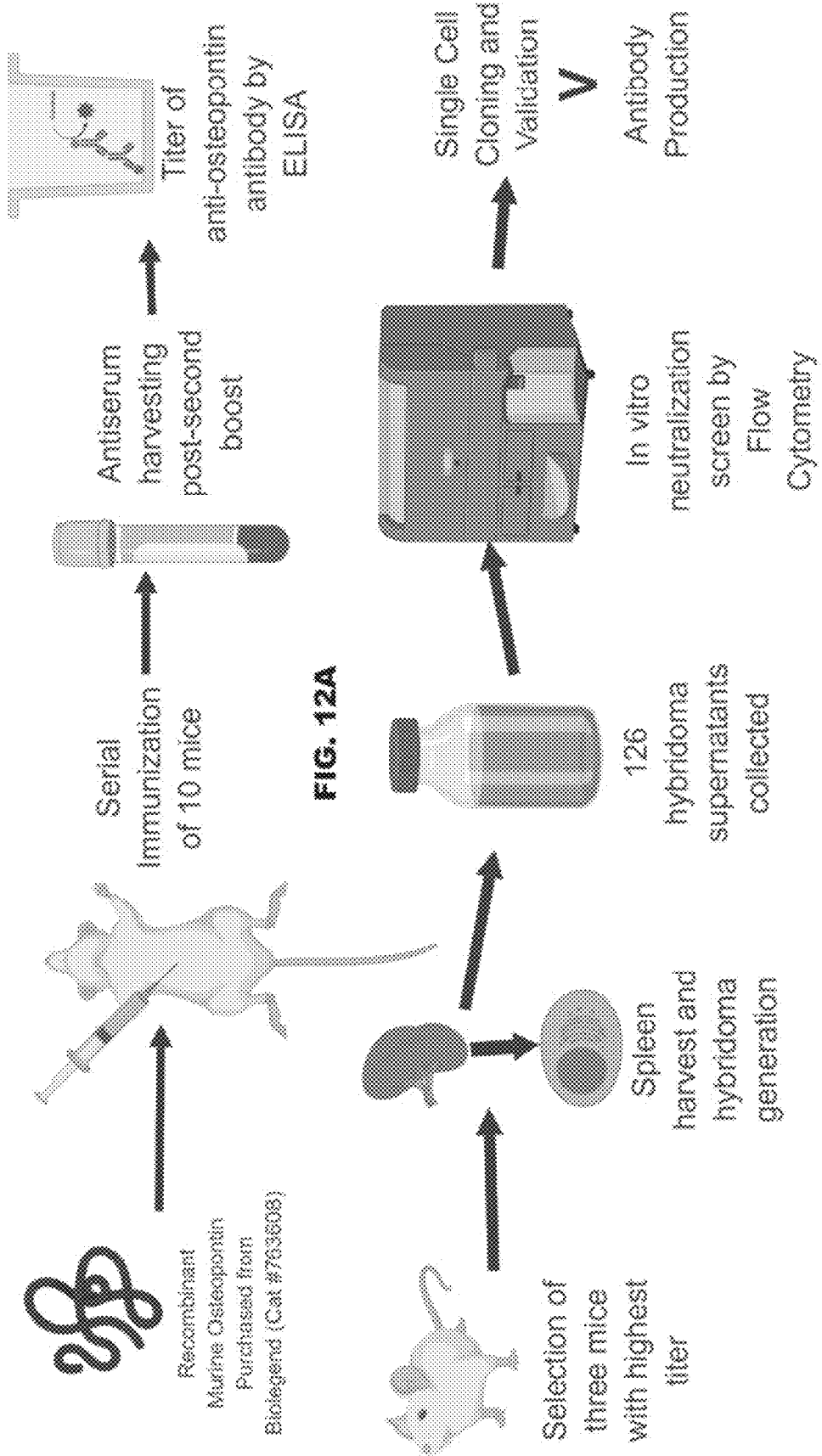
FIGS. 12A-12B are schematic illustrations showing the antibody generation scheme.
Figure 14D:
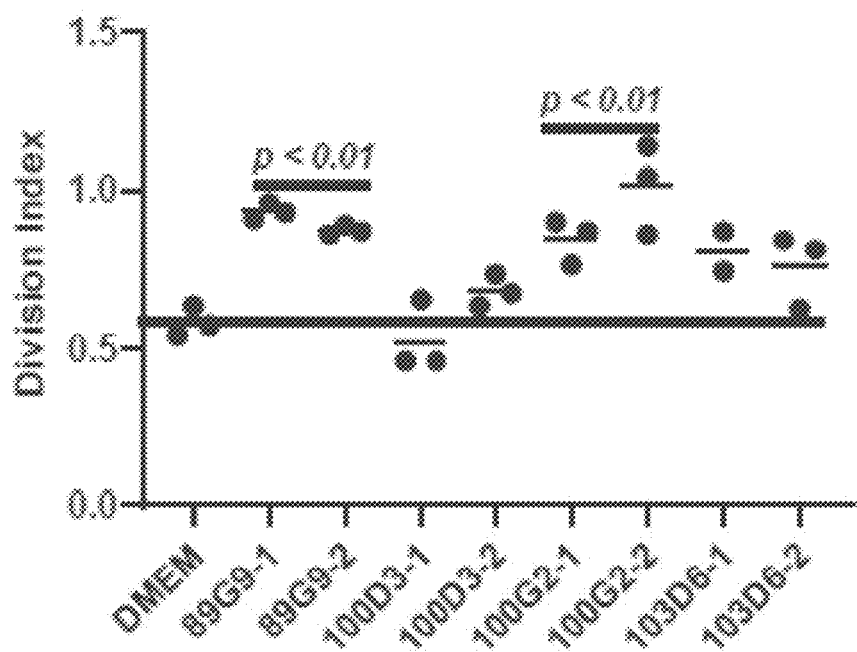
FIG. 14D is a graph showing cell division index in cells treated with the indicated anti-OPN mAbs.
Figures 14E, 14F:
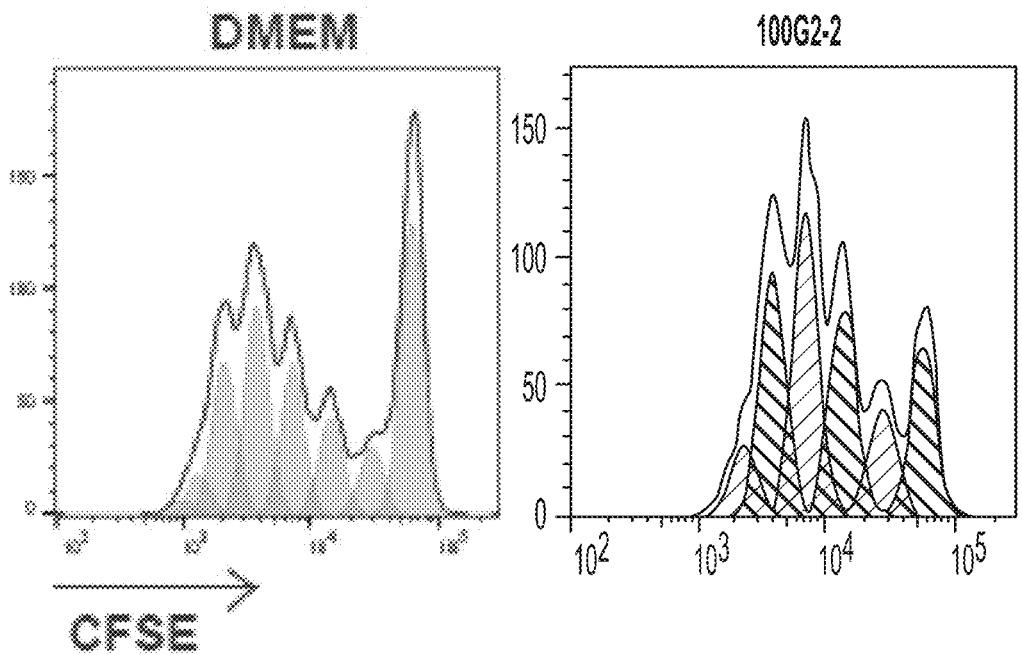
FIG. 14E-14F are flow cytometry histograms showing CSFE staining in cells treated with DMEM or mAb 100G2-2.
Figure 14G:
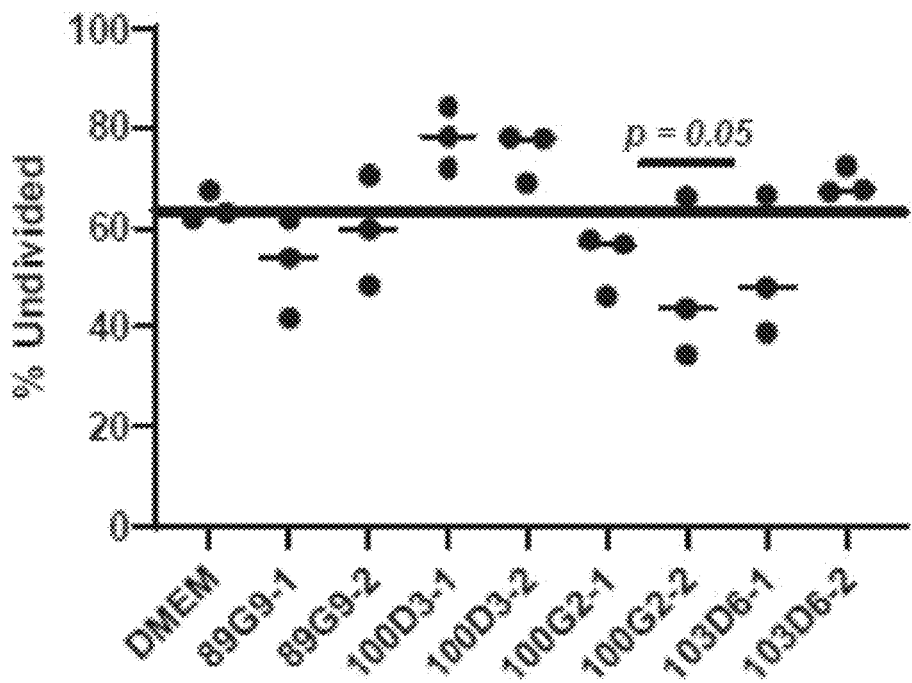
FIGS. 14G-14H are graphs showing percent undivided cells (FIG. 14G) and the division index (FIG. 14H) in cells treated with the indicated anti-OPN mAbs.
Figure 14H:
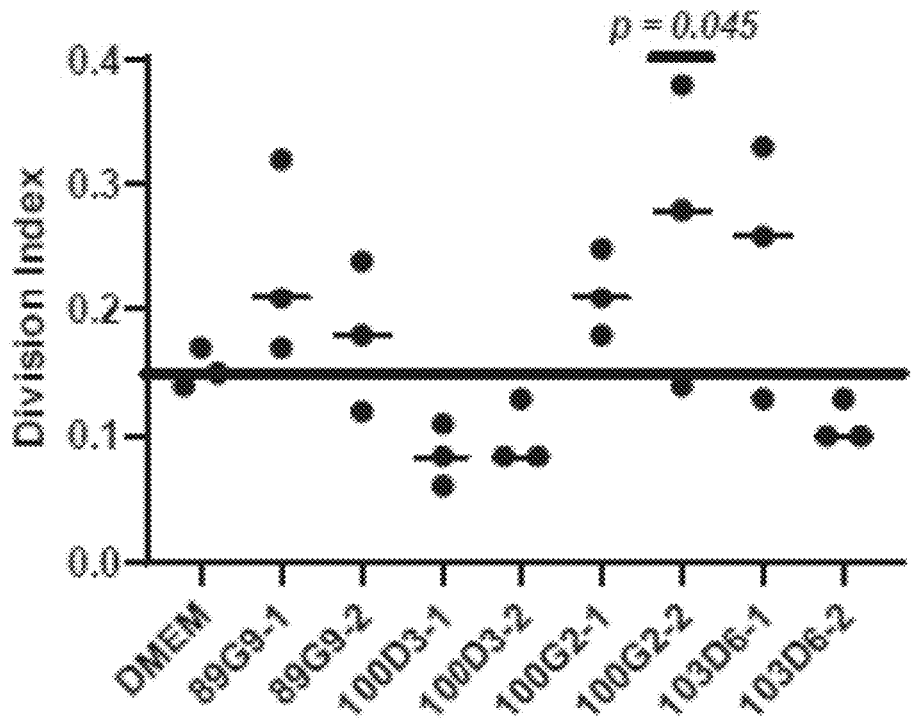
Figure 14I:
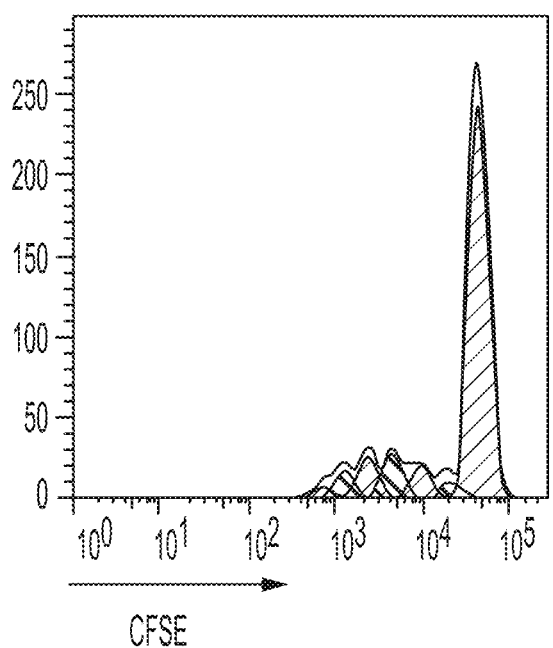
Figure 14J:
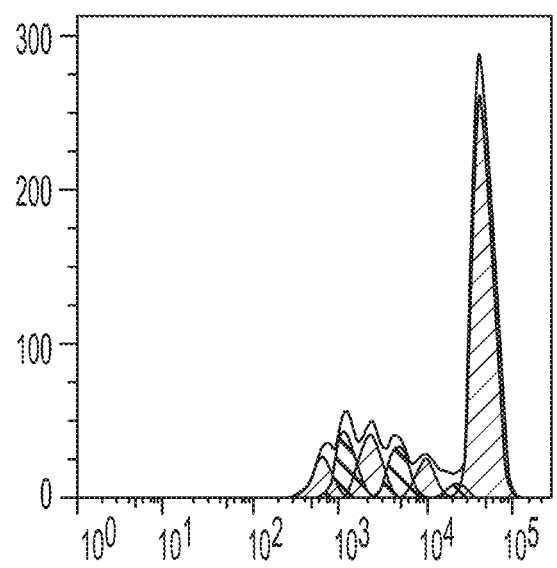

FIGS. 9A-9B show that OPN levels are elevated in human colorectal cancer and human pancreatic cancer when compared to healthy donors. FIGS. 11A-11D show that cells deficient in OPN show higher levels of apoptosis due to T cell induced killing.

OPN decreases metastatic potential as shown in FIG. 11E. Significantly reduced tumor nodule formation was observed in OPN-deficient cells.

Example 10. OPN Monoclonal Antibodies

Methods

OPN Binding Assay. Recombinant mOPN was coated at 4 C overnight on flat-bottom 96-well plates at a concentration of 5 μg/mL. Plates were washed 4× with ELISA wash Buffer (PBS+0.05% Tween-20) then blocked with 1× Assay Buffer (Biolegend Cat #:421203) and incubated at room temperature for 1 hour. Plates were then washed 4× with ELISA wash buffer, then incubated with 100ul of indicated hybridoma supernatants for 2 hours at room temperature. After being washed 4× with ELISA wash buffer, wells were incubated with 500 ng/mL of biotinylated anti-mouse IgG (Biolegend, clone poly4053) for 2 hours at room temperature. After being washed 4× with wash buffer, wells were incubated with a 1:1000 dilution of streptavidin-conjugated HRP (Biolegend, Cat #: 405210) for 30 minutes at RT. Following 5× washing with wash buffer, wells were developed by the addition of TMB substrate (Biolegend Cat #:421101) for 20 min at RT in the dark. The reaction was quenched by the addition of 1N H2SO4 and absorbance at 450 and 570 nm was calculated by a Cytation5 (Biotek, Winooski). Normalized OD was calculated by subtracting absorbance at 570 from absorbance at 450.

OPN Neutralization Assay. Recombinant mouse or human OPN was coated at 4 C overnight on flat-bottom 96 well plates ([mouse]: 2.5 μg/mL; [human]: 10 μg/mL). Plates were washed 4× with PBS, then incubated in the presence of 100 μl of indicated anti-OPN mAb supernatants or control supernatant for 4 hours at room temperature. Plates were then washed 4× with PBS, then 1*10^5 CFSE-labeled mouse or human CD3+ T cells were plated and allowed to culture for 72 hours. Cells were then harvested, stained with anti-CD4, CD25 and CD8a antibodies and CFSE dilution was assayed by flow cytometry.

Results

FIGS. 14A-14J demonstrate the in vitro neutralizing capacities of the disclosed OPN mAb subclones in both mouse and human models.

We claim:

1. A monoclonal antibody or antigen-binding fragment thereof that binds specifically to OPN, wherein the antibody comprises the heavy chain variable region (HCVR) sequences of SEQ ID NO:7, and the light chain variable region (LCVR) of SEQ ID NO:6.

2. The monoclonal antibody of claim 1, wherein the HCVR comprises HCDR1 according to SEQ ID NO:17, HCDR2 according to SEQ ID NO:18, HCDR3 according to SEQ ID NO:19; and the LCVR comprises LCDR1 according to SEQ ID NO:14, LCDR2 according to SEQ ID NO:15, and LCDR3 according to SEQ ID NO:16.

3. A monoclonal antibody or antigen-binding fragment thereof that binds specifically to OPN, wherein the antibody comprises the heavy chain variable region (HCVR) sequences of SEQ ID NO:9; and the light chain variable region (LCVR) of SEQ ID NO:8.

4. The monoclonal antibody of claim 3, wherein the HCVR comprises HCDR1 according to SEQ ID NO:23, HCDR2 according to SEQ ID NO:24, HCDR3 according to SEQ ID NO:25, and the LCVR comprises LCDR1 according to SEQ ID NO:20, LCDR2 according to SEQ ID NO:21, and LCDR3 according to SEQ ID NO:22.

5. A monoclonal antibody or antigen-binding fragment thereof that binds specifically to OPN, wherein the antibody comprises the heavy chain variable region (HCVR) sequences of SEQ ID NO:11, and the light chain variable region (LCVR) of SEQ ID NO:10.

6. The monoclonal antibody of claim 5, wherein the HCVR comprises HCDR1 according to SEQ ID NO:29, HCDR2 according to SEQ ID NO:30, HCDR3 according to SEQ ID NO:31, and the LCVR comprises LCDR1 according to SEQ ID NO:26, LCDR2 according to SEQ ID NO:27, and LCDR3 according to SEQ ID NO:28.

7. A monoclonal antibody or antigen-binding fragment thereof that binds specifically to OPN, wherein the antibody comprises the heavy chain variable region (HCVR) sequences of SEQ ID NO:13, and the light chain variable region (LCVR) of SEQ ID NO:12.

8. The monoclonal antibody of claim 7, wherein the HCVR comprises HCDR1 according to SEQ ID NO:35, HCDR2 according to SEQ ID NO:36, HCDR3 according to SEQ ID NO:37, and the LCVR comprises LCDR1 according to SEQ ID NO:32, LCDR2 according to SEQ ID NO:33, and LCDR3 according to SEQ ID NO:34.

* * * * *